US010143455B2

(12) United States Patent
Lichty, II et al.

(10) Patent No.: US 10,143,455 B2
(45) Date of Patent: Dec. 4, 2018

(54) ENHANCED ULTRASOUND VISUALIZATION OF INTRAVASCULAR DEVICES

(75) Inventors: Robert C. Lichty, II, Santa Rosa, CA (US); Jan R. Lau, Windsor, CA (US); Rodney D. Raabe, Spokane, WA (US); Monte Madsen, Spokane, WA (US)

(73) Assignee: Covidien LLP, Mansfield, MA (US)

( * ) Notice: Subject to any disclaimer, the term of this patent is extended or adjusted under 35 U.S.C. 154(b) by 0 days.

(21) Appl. No.: 13/553,542

(22) Filed: Jul. 19, 2012

(65) Prior Publication Data

US 2013/0072907 A1 Mar. 21, 2013

Related U.S. Application Data

(60) Provisional application No. 61/510,001, filed on Jul. 20, 2011.

(51) Int. Cl.
*A61B 17/00* (2006.01)
*A61B 17/12* (2006.01)
(Continued)

(52) U.S. Cl.
CPC ........ *A61B 17/00491* (2013.01); *A61B 5/061* (2013.01); *A61B 17/12* (2013.01); *A61B 17/12186* (2013.01); *A61M 25/0043* (2013.01); *A61M 25/0108* (2013.01); *A61B 5/02007* (2013.01); *A61B 8/0841* (2013.01); *A61B 2017/00778* (2013.01); *A61B 2090/061* (2016.02); *A61B 2090/3925* (2016.02);
(Continued)

(58) Field of Classification Search
CPC ... A61B 17/00491; A61B 5/061; A61B 17/12; A61B 17/12186; A61B 5/02007; A61B 8/0841; A61B 2017/00778; A61B 2019/461; A61B 2019/5425; A61M 25/0043; A61M 25/0108; A61M 25/0026; A61M 25/005; A61M 25/04; A61M 29/00; A61M 2025/0004; A61M 2025/0681; A61M 2025/1052
USPC .................... 604/264, 97.03, 529
See application file for complete search history.

(56) References Cited

U.S. PATENT DOCUMENTS 3,699,127 A 10/1972 O'Sullivan et al.
3,834,394 A 9/1974 Hunter et al.
(Continued)

FOREIGN PATENT DOCUMENTS

CN 2735942 Y 10/2005
CN 201101549 Y 8/2008
(Continued)

OTHER PUBLICATIONS

U.S. Appl. No. 13/470,200, filed May 11, 2012, Chu et al.
(Continued)

*Primary Examiner* — Lauren P Farrar
(74) *Attorney, Agent, or Firm* — Shumaker & Sieffert, P.A.

(57) ABSTRACT

Methods and devices for providing improved ultrasound visibility of medical devices intended for intravascular use are described. The inclusion of gas/solid boundary regions within a medical devices improves the resolution of the device under ultrasound visualization. Gas/solid boundary regions may be provided through the use of embedded gas-filled microlumens, microwells, or enclosed pockets within the medical device.

19 Claims, 51 Drawing Sheets

(51) Int. Cl.
*A61B 5/06* (2006.01)
*A61M 25/01* (2006.01)
*A61M 25/00* (2006.01)
*A61B 90/00* (2016.01)
*A61B 8/08* (2006.01)
*A61M 25/10* (2013.01)
*A61M 25/06* (2006.01)
*A61M 29/00* (2006.01)
*A61M 25/04* (2006.01)
*A61B 5/02* (2006.01)

(52) U.S. Cl.
CPC ....... *A61M 25/005* (2013.01); *A61M 25/0026* (2013.01); *A61M 25/04* (2013.01); *A61M 29/00* (2013.01); *A61M 2025/0004* (2013.01); *A61M 2025/0681* (2013.01); *A61M 2025/1052* (2013.01)

(56) References Cited

U.S. PATENT DOCUMENTS

| | | |
|---|---|---|
| 4,038,345 A | 7/1977 | O'Sullivan et al. |
| 4,039,665 A | 8/1977 | Foley |
| 4,085,757 A | 4/1978 | Pevsner |
| 4,102,945 A | 7/1978 | Gleave |
| 4,125,494 A | 11/1978 | Schoenberg et al. |
| 4,213,461 A | 7/1980 | Pevsner |
| 4,268,495 A | 5/1981 | Muxfeldt et al. |
| 4,582,061 A | 4/1986 | Fry |
| RE32,348 E | 2/1987 | Pevsner |
| 4,705,517 A | 11/1987 | DiPisa, Jr. |
| 4,805,628 A | 2/1989 | Fry et al. |
| 4,994,069 A | 2/1991 | Ritchart et al. |
| 4,997,861 A | 3/1991 | Hechenberger et al. |
| 5,022,399 A | 6/1991 | Biegeleisen |
| 5,034,456 A | 7/1991 | Katsumura et al. |
| 5,092,390 A | 3/1992 | Witt |
| 5,269,762 A | 12/1993 | Armbruster et al. |
| 5,327,891 A | 7/1994 | Rammler |
| 5,382,261 A | 1/1995 | Palmaz |
| 5,383,466 A | 1/1995 | Partika |
| 5,456,693 A | 10/1995 | Conston et al. |
| 5,480,935 A | 1/1996 | Greff et al. |
| 5,520,653 A | 5/1996 | Reilly et al. |
| 5,536,490 A | 7/1996 | Klaveness et al. |
| 5,656,036 A | 8/1997 | Palmaz |
| 5,665,817 A | 9/1997 | Greff et al. |
| 5,667,767 A | 9/1997 | Greff et al. |
| 5,676,962 A | 10/1997 | Gamido et al. |
| 5,733,294 A | 3/1998 | Forber et al. |
| 5,814,016 A | 9/1998 | Valley et al. |
| 5,830,178 A | 11/1998 | Greff et al. |
| 5,830,222 A | 11/1998 | Makower |
| 5,851,508 A | 12/1998 | Greff et al. |
| 5,868,703 A | 2/1999 | Bertolero et al. |
| 5,874,044 A | 2/1999 | Kotzev |
| 5,981,621 A | 11/1999 | Clark et al. |
| 6,013,053 A | 1/2000 | Bower et al. |
| 6,053,870 A * | 4/2000 | Fulton, III ......... A61B 17/3421 600/458 |
| 6,106,806 A | 8/2000 | Klaveness et al. |
| 6,121,341 A | 9/2000 | Sawhney et al. |
| 6,136,326 A | 10/2000 | Kotzev |
| 6,143,352 A | 11/2000 | Clark et al. |
| 6,143,805 A | 11/2000 | Hickey et al. |
| 6,190,353 B1 | 2/2001 | Makower et al. |
| 6,191,202 B1 | 2/2001 | Greff et al. |
| 6,260,737 B1 | 7/2001 | Gruendeman et al. |
| 6,322,548 B1 | 11/2001 | Payne et al. |
| 6,323,275 B2 | 11/2001 | Takahashi et al. |
| 6,412,639 B1 | 7/2002 | Hickey |
| 6,433,096 B1 | 8/2002 | Hickey et al. |
| 6,443,941 B1 | 8/2002 | Slepian et al. |
| 6,565,840 B1 | 5/2003 | Clark et al. |
| 6,572,873 B1 | 6/2003 | Osman et al. |
| 6,579,311 B1 | 6/2003 | Makower |
| 6,579,916 B1 | 6/2003 | Askill et al. |
| 6,602,241 B2 | 8/2003 | Makower et al. |
| 6,607,512 B2 | 8/2003 | Oliver et al. |
| 6,616,675 B1 | 9/2003 | Evard et al. |
| 6,638,293 B1 | 10/2003 | Makower et al. |
| 6,655,386 B1 | 12/2003 | Makower et al. |
| 6,695,787 B2 | 2/2004 | Hogendijk et al. |
| 6,699,261 B1 | 3/2004 | Cates et al. |
| 6,699,928 B2 | 3/2004 | Cobbley et al. |
| 6,723,052 B2 | 4/2004 | Mills |
| 6,726,674 B2 | 4/2004 | Leu |
| 6,743,858 B2 | 6/2004 | Hickey et al. |
| 7,077,836 B2 | 7/2006 | Lary et al. |
| 7,083,634 B2 | 8/2006 | Shalaby |
| 7,094,216 B2 | 8/2006 | Trombley, III et al. |
| 7,134,438 B2 | 11/2006 | Makower et al. |
| 7,166,570 B2 | 1/2007 | Hunter et al. |
| 7,201,758 B2 | 4/2007 | Farmache |
| 7,229,413 B2 | 6/2007 | Violante et al. |
| 7,235,052 B2 | 6/2007 | Kellar et al. |
| 7,258,669 B2 | 8/2007 | Russell |
| 7,303,571 B2 | 12/2007 | Makower et al. |
| 7,314,466 B2 | 1/2008 | Lary et al. |
| 7,351,426 B2 | 4/2008 | Shalaby et al. |
| 7,371,345 B2 | 5/2008 | Stewart et al. |
| 7,402,320 B2 | 7/2008 | Mirizzi et al. |
| 7,648,527 B2 | 1/2010 | Agnew et al. |
| 7,687,053 B2 | 3/2010 | Porter |
| 7,772,306 B2 | 8/2010 | Blacklock et al. |
| 7,875,017 B2 | 1/2011 | Sabbah |
| 7,932,305 B2 | 4/2011 | Badejo et al. |
| 8,029,560 B2 | 10/2011 | Bates et al. |
| 8,092,390 B2 | 1/2012 | Field |
| 8,110,144 B2 | 2/2012 | Morales |
| 8,173,722 B2 | 5/2012 | Baiker et al. |
| 8,192,731 B2 | 6/2012 | Misiak et al. |
| 8,198,344 B2 | 6/2012 | Zhang et al. |
| 8,287,687 B1 | 10/2012 | Schueneman et al. |
| 8,293,838 B2 | 10/2012 | Zhang et al. |
| 8,313,533 B2 | 11/2012 | Goldmann |
| 8,398,596 B2 | 3/2013 | Field |
| 8,419,711 B2 | 4/2013 | Sabbah |
| 8,475,492 B2 | 7/2013 | Raabe et al. |
| 8,491,881 B2 | 7/2013 | Salamone et al. |
| 8,518,104 B2 | 8/2013 | Bates et al. |
| 8,541,495 B2 | 9/2013 | Ishizaki et al. |
| 8,617,079 B2 * | 12/2013 | Mitchell .............. A61B 8/0833 600/437 |
| 8,808,620 B1 | 8/2014 | Chu et al. |
| 8,845,614 B2 | 9/2014 | Raabe et al. |
| 8,852,178 B2 | 10/2014 | Thompson et al. |
| 9,011,486 B2 | 4/2015 | Raabe et al. |
| 9,084,835 B2 | 7/2015 | Crawford et al. |
| 9,561,023 B2 | 2/2017 | Raabe et al. |
| 9,592,037 B2 | 3/2017 | Raabe et al. |
| 2002/0177772 A1 | 11/2002 | Altman et al. |
| 2002/0188195 A1 | 12/2002 | Mills |
| 2003/0012735 A1 | 1/2003 | Unger et al. |
| 2003/0050531 A1 * | 3/2003 | Field ................... A61B 17/435 600/34 |
| 2003/0065266 A1 * | 4/2003 | Russell .................. A61B 90/39 600/462 |
| 2003/0186005 A1 | 10/2003 | Rivera et al. |
| 2003/0202956 A1 | 10/2003 | Clark et al. |
| 2003/0206864 A1 | 11/2003 | Mangin |
| 2004/0068190 A1 | 4/2004 | Cespedes |
| 2004/0073238 A1 | 4/2004 | Makower |
| 2004/0098030 A1 | 5/2004 | Makower et al. |
| 2004/0143212 A1 | 7/2004 | Trombley et al. |
| 2004/0172060 A1 | 9/2004 | Cates et al. |
| 2004/0193055 A1 | 9/2004 | Field et al. |
| 2004/0230119 A1 | 11/2004 | Brustad et al. |
| 2005/0113798 A1 * | 5/2005 | Slater ................... A61M 25/01 604/508 |
| 2005/0137575 A1 | 6/2005 | Thompson et al. |
| 2005/0273074 A1 * | 12/2005 | Lewis ........................ 604/508 |
| 2006/0030808 A1 | 2/2006 | Kennedy |

(56) References Cited

U.S. PATENT DOCUMENTS

| | | |
|---|---|---|
| 2006/0052822 A1 | 3/2006 | Mirizzi et al. |
| 2006/0052823 A1 | 3/2006 | Mirizzi et al. |
| 2006/0062687 A1 | 3/2006 | Morales |
| 2006/0149218 A1 | 7/2006 | Slater et al. |
| 2006/0195134 A1 | 8/2006 | Crittenden |
| 2006/0276743 A1 | 12/2006 | MacMahon et al. |
| 2007/0021730 A1 | 1/2007 | Flaherty et al. |
| 2007/0078207 A1 | 4/2007 | Jonn et al. |
| 2007/0100405 A1 | 5/2007 | Thompson |
| 2007/0208417 A1 | 9/2007 | Agnew |
| 2007/0248486 A1 | 10/2007 | Morales |
| 2007/0255140 A1 | 11/2007 | Violante et al. |
| 2007/0265370 A1 | 11/2007 | Anitua Aldecoa |
| 2007/0292472 A1 | 12/2007 | Paul et al. |
| 2008/0021139 A1 | 2/2008 | Blacklock et al. |
| 2008/0039548 A1 | 2/2008 | Zavatsky et al. |
| 2008/0045996 A1 | 2/2008 | Makower et al. |
| 2008/0103456 A1* | 5/2008 | Johnson ............... A61B 5/6864 604/264 |
| 2008/0103564 A1 | 5/2008 | Burkinshaw et al. |
| 2008/0154136 A1 | 6/2008 | Webler |
| 2008/0213463 A1* | 9/2008 | Cook ..................... A61L 31/10 427/2.24 |
| 2008/0241249 A1 | 10/2008 | Quintero et al. |
| 2008/0269720 A1 | 10/2008 | Sabbah |
| 2008/0311323 A1 | 12/2008 | Morales |
| 2009/0054773 A1* | 2/2009 | Shizuka ............... A61B 8/0841 600/439 |
| 2009/0131938 A1 | 5/2009 | Khatri et al. |
| 2009/0257976 A1 | 10/2009 | Kerber et al. |
| 2009/0264769 A1 | 10/2009 | Sadaka |
| 2009/0317353 A1 | 12/2009 | Zhang et al. |
| 2010/0114130 A1* | 5/2010 | Meade ............... A61B 17/0401 606/155 |
| 2010/0144895 A1 | 6/2010 | Porter |
| 2010/0174370 A1* | 7/2010 | Shalon .................. A61F 5/0003 623/16.11 |
| 2010/0213096 A1 | 8/2010 | Morales |
| 2010/0217306 A1 | 8/2010 | Raabe et al. |
| 2010/0217313 A1 | 8/2010 | Raabe et al. |
| 2010/0239505 A1 | 9/2010 | Reichl et al. |
| 2011/0060277 A1 | 3/2011 | Lilley |
| 2011/0098564 A1 | 4/2011 | Larson et al. |
| 2011/0172488 A1 | 7/2011 | Field |
| 2011/0178399 A1 | 7/2011 | Del Corso |
| 2011/0224538 A1* | 9/2011 | Linares ................ A61B 8/0841 600/424 |
| 2011/0224723 A1 | 9/2011 | Lee et al. |
| 2011/0251318 A1 | 10/2011 | Ishizaki et al. |
| 2011/0269870 A1 | 11/2011 | Cohn et al. |
| 2012/0027821 A1 | 2/2012 | Shirotake et al. |
| 2012/0064027 A1 | 3/2012 | Shalaby |
| 2012/0109191 A1 | 5/2012 | Marano et al. |
| 2012/0128903 A1 | 5/2012 | Morales |
| 2013/0011589 A1 | 1/2013 | Morales |
| 2013/0052152 A1 | 2/2013 | Keplinger |
| 2013/0072907 A1 | 3/2013 | Lichty, II et al. |
| 2013/0085384 A1 | 4/2013 | Field |
| 2013/0095262 A2 | 4/2013 | Morales |
| 2013/0116633 A1 | 5/2013 | Lichty, II et al. |
| 2013/0144159 A1 | 6/2013 | Field et al. |
| 2013/0150712 A1 | 6/2013 | Field |
| 2013/0156824 A1 | 6/2013 | Keplinger |
| 2013/0204232 A1 | 8/2013 | Wieser et al. |
| 2013/0211182 A1 | 8/2013 | Sabbah et al. |
| 2013/0225640 A1 | 8/2013 | Kim |
| 2013/0267942 A1 | 10/2013 | Fulton et al. |
| 2013/0281835 A1 | 10/2013 | Field et al. |
| 2013/0303654 A1 | 11/2013 | Salamone et al. |
| 2015/0018867 A1 | 1/2015 | Raabe et al. |
| 2015/0037200 A1 | 2/2015 | Crawford et al. |
| 2015/0044091 A1 | 2/2015 | Morales |
| 2015/0265264 A1 | 9/2015 | Raabe et al. |

FOREIGN PATENT DOCUMENTS

| | | |
|---|---|---|
| EP | 0 567 186 A1 | 1/1999 |
| EP | 1 230 313 A1 | 8/2002 |
| EP | 1 206 291 B1 | 10/2005 |
| EP | 2 162 139 A1 | 3/2010 |
| EP | 2 303 342 A2 | 4/2011 |
| EP | 2 303 343 A2 | 4/2011 |
| JP | H06-7440 | 1/1994 |
| JP | 2000-290600 | 10/2000 |
| JP | 2006-523471 | 10/2006 |
| WO | WO 86/06738 | 11/1986 |
| WO | 9421324 A1 | 9/1994 |
| WO | 9640327 A1 | 12/1996 |
| WO | WO 96/40347 | 12/1996 |
| WO | 9748337 A1 | 12/1997 |
| WO | 0108727 A1 | 2/2001 |
| WO | 0132795 A1 | 5/2001 |
| WO | WO 2004/071612 A2 | 8/2004 |
| WO | 2009003017 A1 | 12/2008 |
| WO | 2009155589 A2 | 12/2009 |
| WO | WO 2010/033406 A1 | 3/2010 |
| WO | WO 2013/013080 | 1/2013 |

OTHER PUBLICATIONS

U.S. Appl. No. 13/842,722, filed Mar. 15, 2013, Choi et al.
U.S. Appl. No. 14/323,926, filed Jul. 3, 2014, Crawford et al.
U.S. Appl. No. 14/453,493, filed Aug. 6, 2014, Morales.
U.S. Appl. No. 14/473,596, filed Aug. 29, 2014, Raabe et al.
"Bacillus Atrophaeus Spores", Autoclave Testing Service, Inc. www.autoclavesporetesting.com-Bacillus_Atrophaeus_Spores.htm, Jul. 6, 2010, webpage copy from Internet Archive Wayback Machine: https:--archive.org-web-.
"Biological Indicators and Inoculated Carriers", NAMSA—Medical Device Testing Laboratory and Contract Research Organization, www.namsa.com-products-biological.com, Jul. 30, 2010, webpage copy from Internet Archive Wayback Machine: https:--archive.org-web-.
"Dry Heat Sterilizers", Autoclave Testing Service, Inc., www.autoclavesporetesting.com-dry_heat_sterilization.com, Jul. 4, 2010, webpage copy from Internet Archive Wayback Machine: https:--archive.org-web-.
"Monitoring the Effectiveness of the Sterilization Process", Sterile Processing University 2007, www.spdceus.com-monitoring_sterilization_process.com, Nov. 28, 2010, webpage copy from Internet Archive Wayback Machine: https:--archive.org-web-.
"Process Validation: Moist Heat Sterilization for Pharmaceuticals", Health Canada, Health Products and Food Branch, www.hc-sc.gc.ca-dhp-mps-compli-conform-gmp-bpf-validation-mhsp-schpp_tc-tm-eng.php, Mar. 1, 2001.
"Steps of Dry-Heat Sterilization", Engender Health www.engenderhealth.org-ip-instrum-inm11.com, Aug. 13, 2010, webpage copy from Internet Archive Wayback Machine: https:--archive.org-web-.
"Sterility Assurance for Industry & Healthcare", Raven Labs Products and services, Mesa Laboratories, Inc., www.mesalabs.com-products-services-raven-labs.com, Jul. 30, 2010, webpage copy from Internet Archive Wayback Machine: https:--archive.org-web-.
"Sterilization—An Overview", Pacific BioLabs, 2004 PowerPoint presentation, www.pacificbiolabs.com-tech_downloads.asp, Sep. 26, 2010, copy from Internet Archive Wayback Machine: https:--archive.org-web-.
"Validating Heat Sterilization", Pacific BioLabs, 2007 PowerPoint presentation, www.pacificbiolabs.com-tech_downloads.asp, Sep. 26, 2010, copy from Internet Archive Wayback Machine: https:--archive.org-web-.
Case et al., "Dry Heat Sterilization and Depyrogenation Validation and Monitoring", Agalloco et al. ed., *Validation of Pharmaceutical Processes*, Informa Healthcare USA, Inc., pp. 223-240 (2008).
Chieppo et al., "Sterilization: Dry Heat", Swarbrick, ed., *Encyclopedia of Pharmaceutical Technology*, 3rd Ed., vol. 6, Informa Healthcare USA, Inc., Chapter 252, pp. 3512-3518 (2007).

(56) References Cited

OTHER PUBLICATIONS

Darmady et al., "Sterilization by Dry Heat", J. Clin. Path. 14, pp. 38-44 (1961), lecture given on Feb. 2, 1960.
Gillis et al., "Understanding Biological Indicator Grow-Out Times", Pharmaceutical Technology, vol. 34, No. 1, Jan. 2010.
International Search Report and Written Opinion in PCT Application No. PCT/US12/047460, dated Dec. 21, 2012.
Joslyn, "Sterilization by Heat", Block, ed., *Disinfection, Sterilization, and Preservation*, 5th Ed. Lippincott Williams & Wilkins, Chapter 36, pp. 695-728 (2001).
Merritt, "Sterilization Process for a Medical Adhesive", Senior Project submitted in partial fulfillment for Bachelor of Science in Manufacturing Engineering, California Polytechnic State University, San Luis Obispo, pp. 1-45 (Jul. 11, 2011).
Pistolesi, "Sterilization: Moist Heat", Swarbrick, ed., *Encyclopedia of Pharmaceutical Technology*, 3rd Ed., vol. 6, Informa Healthcare USA, Inc., Chapter 252, pp. 3529-3539 (2007).
Sasaki et al., "Evaluation of High-Temperature and Short-Time Sterilization of Injection Ampules by Microwave Heating", *PDA Journal of Pharmaceutical Science and Technology*, Jan./Feb. 1998, 52(1):5-12: Abstract.
Sasaki et al., "Microwave Continuous Sterilization of Injection Ampoules", *PDA Journal of Pharmaceutical Science and Technology*, May-Jun. 1996, 50(3):172-9: Abstract.
Sasaki et al., "Validation of a Microwave Sterilizer for Injection Ampules", *PDA Journal of Pharmaceutical Science and Technology*, 1999, 53:60-69.
Solanki et al., "Microwave Technology—A Potential Tool in Pharmaceutical Science", International Journal of PharmTech Research, Jul.-Sep. 2010, 2(3):1754-1761.
Tietjen et al., "Sterilization", Infection Prevention Guidelines for Healthcare Facilities with Limited Resources, Chapter 11, 1992, JHPIEGO Corporation, 2003, www.reproline.jhu.edu-english-4morerh-4ip-IP_manual-11_Sterilization.pdf.
Office Action from U.S. Appl. No. 14/473,596, dated Feb. 11, 2015, 8 pp.
International Preliminary Report on Patentability from International Patent Application No. PCT/US2012/047460, dated Jan. 21, 2014, 7 pp.
International Search Report from International Patent Application No. PCT/US2010/024820, dated May 11, 2010, 2 pp.
Written Opinion from International Patent Application No. PCT/US2010/024820, dated May 11, 2010, 5 pp.
Prosecution History from U.S. Pat. No. 8,475,492, dated Aug. 13, 2012 through Mar. 15, 2013, 41 pp.
Prosecution History from U.S. Pat. No. 8,845,614, dated Apr. 23, 2013 through Apr. 25, 2014, 79 pp.
Prosecution History from U.S. Appl. No. 14/473,596, dated Feb. 11, 2015 through Jan. 21, 2016, 79 pp.
Final Office Action from U.S. Appl. No. 14/473,596, dated Aug. 25, 2015, 9 pp.
Final Office Action from U.S. Appl. No. 14/473,596, dated Jul. 22, 2016, 8 pp.
Response to Final Office Action dated Jul. 22, 2016, from U.S. Appl. No. 14/473,596, filed Sep. 19, 2016, 9 pp.
Notice of Allowance from U.S. Appl. No. 14/473,596, dated Sep. 30, 2016, 8 pp.

\* cited by examiner

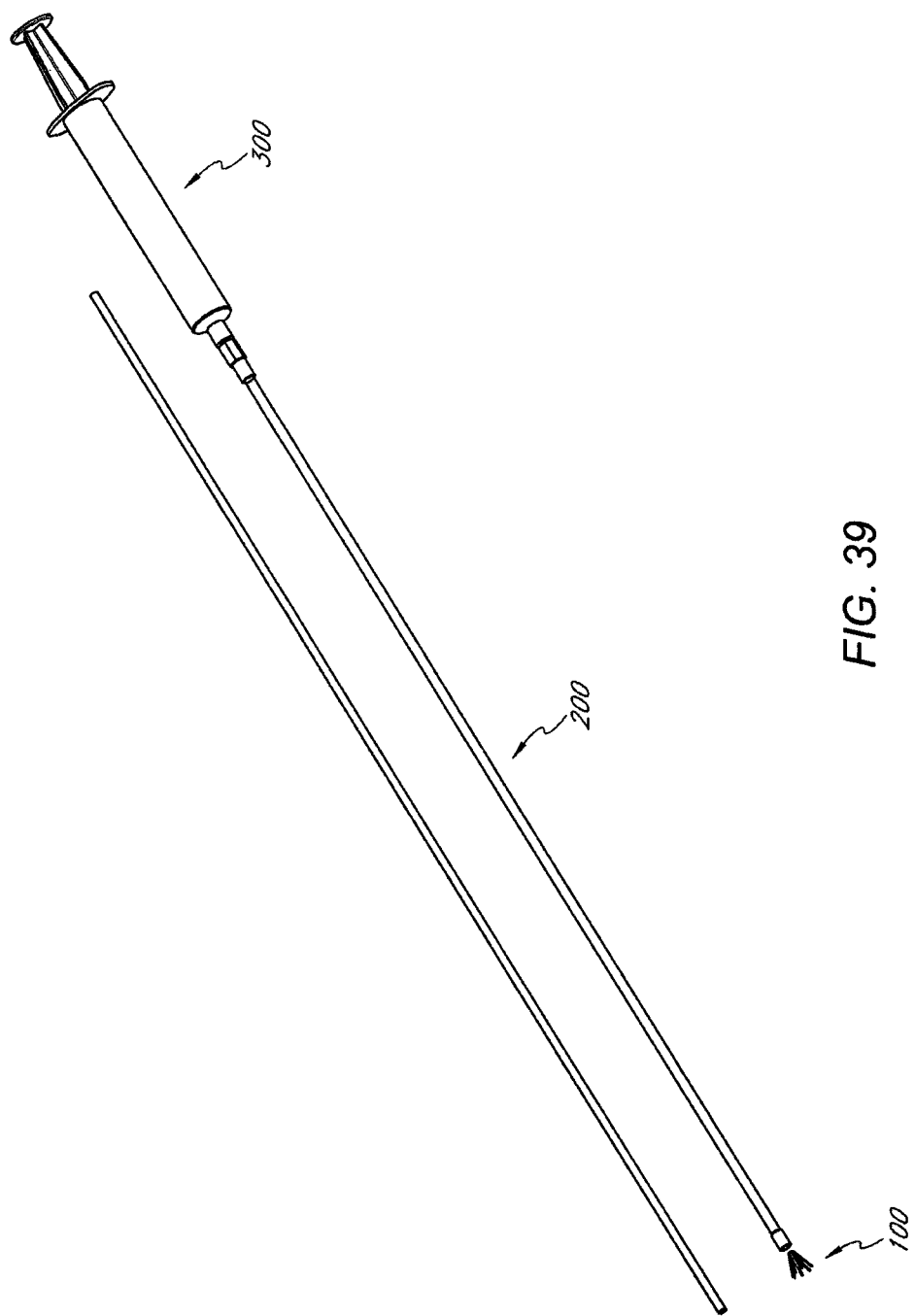

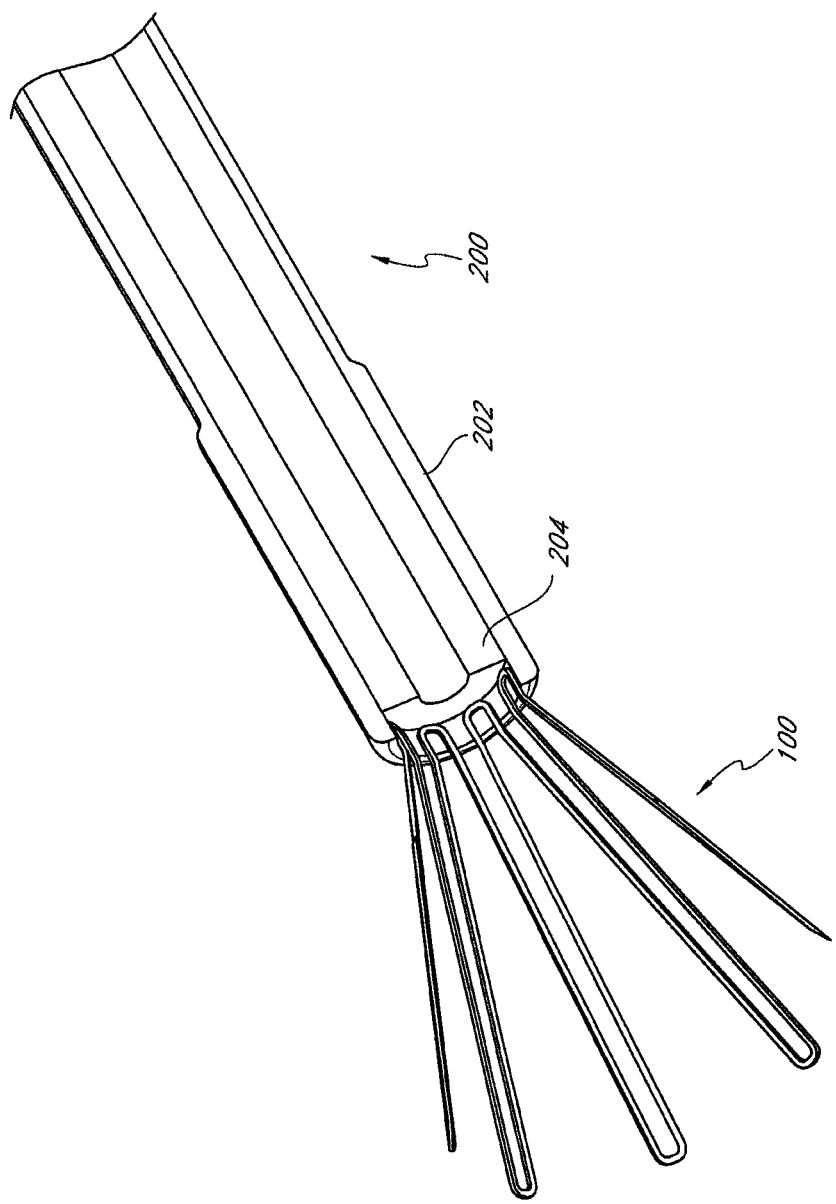

ENHANCED ULTRASOUND VISUALIZATION OF INTRAVASCULAR DEVICES

PRIORITY CLAIM

This application claims priority under 35 U.S.C. § 119(e) to U.S. Provisional App. No. 61/510,001 filed on Jul. 20, 2011, which is hereby incorporated by reference in its entirety. This application hereby incorporates by reference in its entirety U.S. patent application Ser. No. 12/710,318 filed on Feb. 22, 2010 and published as U.S. Pat. Pub. No. 2010/0217306 A1 on Aug. 26, 2010.

BACKGROUND OF THE INVENTION

Healthy leg veins contain valves that allow blood to move in one direction from the lower limbs toward the heart. These valves open when blood is flowing toward the heart, and close to prevent venous reflux, or the backward flow of blood. When veins weaken and become enlarged, their valves cannot close properly, which leads to venous reflux and impaired drainage of venous blood from the legs. Venous reflux is most common in the superficial veins. The largest superficial vein is the great saphenous vein, which runs from the top of the foot to the groin, where it originates at a deep vein.

Factors that contribute to venous reflux disease include female gender, heredity, obesity, lack of physical activity, multiple pregnancies, age, past history of blood clots in the legs and professions that involve long periods of standing. According to population studies, the prevalence of visible tortuous varicose veins, a common indicator of venous reflux disease, is up to 15% for adult men and 25% for adult women. A clinical registry of over 1,000 patients shows that the average age of patients treated for venous reflux is 48 and over 75% of the patients are women.

In men, the testicular blood vessels originate in the abdomen and course down through the inguinal canal as part of the spermatic cord on their way to the testis, where they form a network of small veins known as the pampiniform plexus. Upward flow of blood in the veins is ensured by small one-way valves that prevent backflow. Defective valves or venous compression by nearby structures can cause dilation and tortuosity of the pampiniform plexus. This may result in a varicocele, or abnormal enlargement of the veins in the scrotum. Like varicose veins, the presence of a varicocele is a common indicator of venous reflux.

Venous reflux can be classified as either asymptomatic or symptomatic, depending on the degree of severity. Symptomatic venous reflux disease is a more advanced stage of the disease and can have a profound impact on the patient's quality of life. People with symptomatic venous reflux disease may seek treatment due to a combination of symptoms and signs, which may include leg pain and swelling; painful varicose veins; skin changes such as discoloration or inflammation; the presence of a palpable, abnormal mass along the spermatic cord; and open skin ulcers.

A primary goal of treating symptomatic venous reflux is to eliminate the reflux at its source, such as, for example, the great saphenous vein. If a diseased vein is either closed or removed, blood can automatically reroute into other veins without any known negative consequences to the patient.

The current non-invasive methods for treatment of reflux in the greater saphenous vein include radiofrequency (RF) ablation, laser endothermal ablation, and sclerotherapy, including foam sclerotherapy. Radiofrequency ablation and laser ablation require tumescent anesthesia which produce both bruising and pain along the inner thigh and upper inner calf for several weeks, and both can have side effects of burns and nerve damage. Radiofrequency ablation and laser ablation also require capital purchases of a radiofrequency device or laser box, often at costs of more than $50,000, in addition to expensive disposal mechanisms. While foam sclerotherapy is relatively non-invasive, it has a high rate of recurrence and potential side effects. All of the methods require wearing compression stockings for 2-4 weeks.

For those treatments which involve careful placement of a catheter at a particular intravenous tratement site, a reliable means for visualizing the instruments is needed. Ultrasound is a common method for device visualization in the medical device industry. Ultrasound works by emitting sound waves and analyzing the waves that are reflected and returned to the ultrasound sensing device. Despite its popularity, ultrasound visualization often provides inadequate resolution for careful intravenous placement of a catheter for the treatment of venous reflux disease, and improved echogenic catheters and methods of use are needed.

SUMMARY OF THE INVENTION

Disclosed herein is a medical device for use under ultrasound visualization. In one embodiment, the device comprises an elongate shaft comprising an outer surface and an inner surface defining an inner lumen, the inner lumen having an open proximal end and an open distal end, a plurality of microlumens having proximal ends and distal ends, embedded within the elongate shaft. The microlumens are arranged between the inner surface and outer surface of the elongate shaft, and they each have closed proximal and distal ends and are configured to contain a gas within to increase the visibility of the device under ultrasound imaging.

According to another embodiment, the device comprises an elongate shaft comprising an outer surface and an inner surface defining an inner lumen, and one or more microwells within the elongate shaft, each microwell having a cross-sectional dimension configured such that gas enters the microwell but surface tension prevents liquid from entering the microwell. The microwells are configured to contain gas within them to increase the visibility of the device under ultrasound imaging.

In yet another embodiment, the medical device comprises an elongate shaft comprising an outer surface and an inner surface defining an inner lumen, wherein the elongate shaft comprises expanded polytetrafluoroethylene containing enclosed gas pockets to increase the visibility of the device under ultrasound imaging.

BRIEF DESCRIPTION OF THE DRAWINGS

FIG. 39 illustrates schematically major components of a vascular occlusion system, according to one embodiment of the invention.

FIGS. 45-47 illustrate perspective, cross-sectional views of an occlusion device in varying stages of deployment out of a delivery catheter, according to one embodiment of the invention.

DETAILED DESCRIPTION OF THE PREFERRED EMBODIMENT

Figure 1:
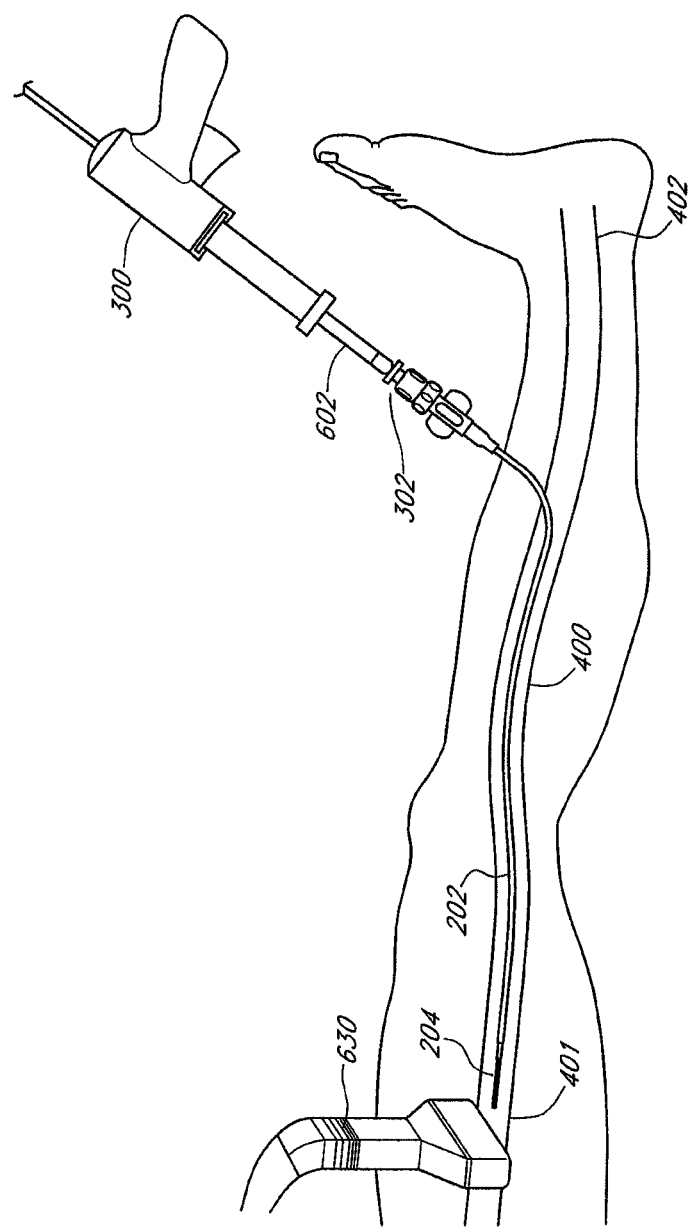
FIGS. 1-11 schematically illustrate a method for occluding a vein, such as the great saphenous vein, using a vein-occluding substance and an imaging tool, according to one embodiment of the invention.

Disclosed herein are systems, methods and devices for the minimally invasive treatment of varicose veins and other medical conditions. When used herein with respect to the device, proximal can refer to toward the access insertion site into a blood vessel, while distal refers to away from the access insertion site and in the direction of the patient. In the treatment as applied to the greater saphenous vein, proximal may mean cephalad, or towards the head, while distal refers to the caudal direction. In some embodiments an occlusive device is deployed to block the saphenous vein just distal to the Superficial Femoral Vein Junction (SFJ) and create a flattened shape so the vein can be treated further using either a substance to alter the vein such that blood flow is prevented therein, such as sclerosing solution or medical adhesive. In some embodiments, complete vein closure is the desired clinical result of all treatments to mitigate the effects of venous hypertension caused by retrograde venous flow. The occlusion device and medical adhesive can be delivered through a catheter utilizing a "single stick" method. This approach is designed to produce less pain and fewer skin injections than used in current treatment approaches, as well as to mitigate or eliminate the need for patients to wear uncomfortable compression stockings after treatment.

Vein-Collapsing Methods

Methods to treat venous insufficiency are now described, in which the vein is compressed at least partially along the treatment zone. Doing so can better ensure that the vein is partially or fully collapsed as opposed to merely occluded, depending on the desired clinical result. Not to be limited by theory, collapsing the vein may place two or more luminal surfaces of endothelial cells into opposing contact with each other, stimulating fibrous tissue proliferation and resulting in improved long-term closure of the vein with a lower risk of recanalization and vein re-opening. In some embodiments, a deployment catheter is percutaneously introduced into a vein at an access site, and translumenally distally advanced across a treatment zone within a vein. External compression is applied to collapse the vein distally of the deployment catheter. Then the distal end of the catheter advances to the very beginning of the occluded vein at the proximal side of the occlusion to minimize the "trapped" blood between the catheter and the occluded vein. After a bolus of plug forming media is expressed from the distal end of the catheter, the occlusion at the end of the catheter forces the vein-occluding substance to flow retrograde (proximally) toward the catheter insertion point into the vein and reduce the distal flow force and mixing with blood within the vessel. This method also allows the vein-occluding media to replace any existing blood "trapped" between the catheter and the occluded vein and forms an occlusive plug within the vein while minimizing mixing with the blood. This reduction in mixing can be advantageous in certain embodiments because it can increase the bonding strength between the vein-occluding media and the vein. External compression distally to the treatment zone optionally may be removed, or may remain throughout all or a portion of the procedure. External compression can also occur around the area of the vein where the plug forming media is expressed in order to collapse the vein as noted above. The catheter is thereafter proximally retracted while dispensing a vein occluding substance, either continuously or via discrete boluses spaced apart from the initial bolus at regular or irregular intervals across the treatment zone. External compression can continue proximally where the vein occluding substance is being dispensed in order to ensure collapse of the vein as noted above. The catheter is thereafter withdrawn, and the access site closed using conventional techniques. The method is described in greater detail below.

The vein closure system can enter the vein such as the greater saphenous or lesser saphenous vein or other vessel using fluoroscopy, ultrasound, or other guidance means. A micro-catheter system can be placed over a wire for introduction of an outer catheter or introduction sheath into the vein. In some embodiments, the vein is entered as distal as possible or as clinically relevant in the abnormal vein. In some embodiments, the closure method comprises advancement of an introducing sheath and/or dilator over a guide wire to the sapheno-femoral junction below the anterior-inferior epigastric vein, which in some embodiments, can be approximately 1.5 to 2.5 cm from the sapheno-femoral junction. Following placement of the sheath to this level and optional verification with ultrasound, an inner catheter is introduced through the sheath and is luer-locked or otherwise secured to the sheath to maintain a fixed position with the tip extending approximately 5 cm from the end of the sheath.

In accordance with FIG. 1, the occlusion method comprises providing an injector such as a glue gun 300 that assists in injecting a vein-occluding substance to occlude vessel 400. In some embodiments, the distal end 302 of the glue gun 300 includes a syringe that is operably connected to an inner catheter 204 by a luer lock 602. A sheath or outer catheter 202 surrounds the inner catheter 204, and assists in providing access to a target site within the vessel 400 interior. In some embodiments, the outer catheter 202 is introduced first followed by the inner catheter 204, while in other embodiments, the outer catheter 202 and inner catheter 204 are introduced simultaneously. As shown in FIG. 1, the outer catheter 202 and inner catheter 204 are introduced near the proximal end 402 of the vessel 400 and are directed towards the distal end 401 of the vessel, where the vein-occluding substance will be released. In one embodiment, at the site of release of the vein-occluding substance, the inner catheter 204 will extend beyond the distal end of the outer catheter 202, such as by between about 3 cm and 7 cm, to prevent any vein-occluding substance from contacting the outer catheter 202.

As shown in FIG. 1, an imaging tool such as an ultrasound transducer 630 can also be provided that could be multi-functional, including guiding one or more catheters, serving as a compression element, and/or identifying areas in the interior of the vessel that may need further occlusion or closure. In some embodiments, the ultrasound transducer 630 can be placed into contact with an external surface of a patient's skin prior to placing the outer catheter 202 and/or inner catheter 204 through the vessel 400. The ultrasound transducer 630 can assist in generating images to help guide one or more catheters to a site where a vein-occluding substance will be introduced. In some embodiments, the ultrasound transducer 630 can also serve as a compression element prior to, during or after introducing a vein-occluding substance to assist in closure of the vessel 400. By serving as a compression element, the ultrasound transducer can help to flatten and/or reduce the size of the vessel 400. In some embodiments, the ultrasound transducer 630 can include a Doppler flow detection capability, and help to identify areas in the interior of the vessel 400 that may need further closure or occlusion and thus, further application of a vein-occluding substance.

When the inner catheter is in position and verified with ultrasound to be in the appropriate position below the sapheno-femoral junction, compression at the sapheno-femoral junction is performed and small amounts of vein occluding substances, including liquid adhesives such as glues including cyanoacrylates, or any substances described elsewhere herein or known in the art, are injected into the vein. The vein can then be collapsed using compression, such as external compression to assist in coapting the vein and adhering the internal walls of the vein to the vein-occluding substance in a solid, permanent bond. In some embodiments, an additional compression device can be provided in addition to the ultrasound transducer or probe (either proximally or distally) to assist in collapsing the vein. In some embodiments, the compression device can be a sequential compression device configured to apply compressive pressure from a compressor against the patient's limb through a flexible pressurized sleeve. The compression can be configured to deliver uniform compression along its length, distal-to-proximal compression in a peristaltic wave or other modes depending on the desired clinical result. In some embodiments, the compressive device could be configured to deliver a pressure of at least about 30, 40, 50, 60, 70, 80, 90, 100, 125, 150, or more mm Hg, or between about 30-150 or 50-100 mm Hg in some embodiments. In some embodiments, an external device delivering energy to create a controlled vasospasm of the vein is used. The energy could be, for example, electrical stimulation, cryotherapy, infrared, visible, or UV light, microwave, RF energy, ultrasound energy, magnetic energy, thermal energy, or a combination of the energy sources.

Figure 2:
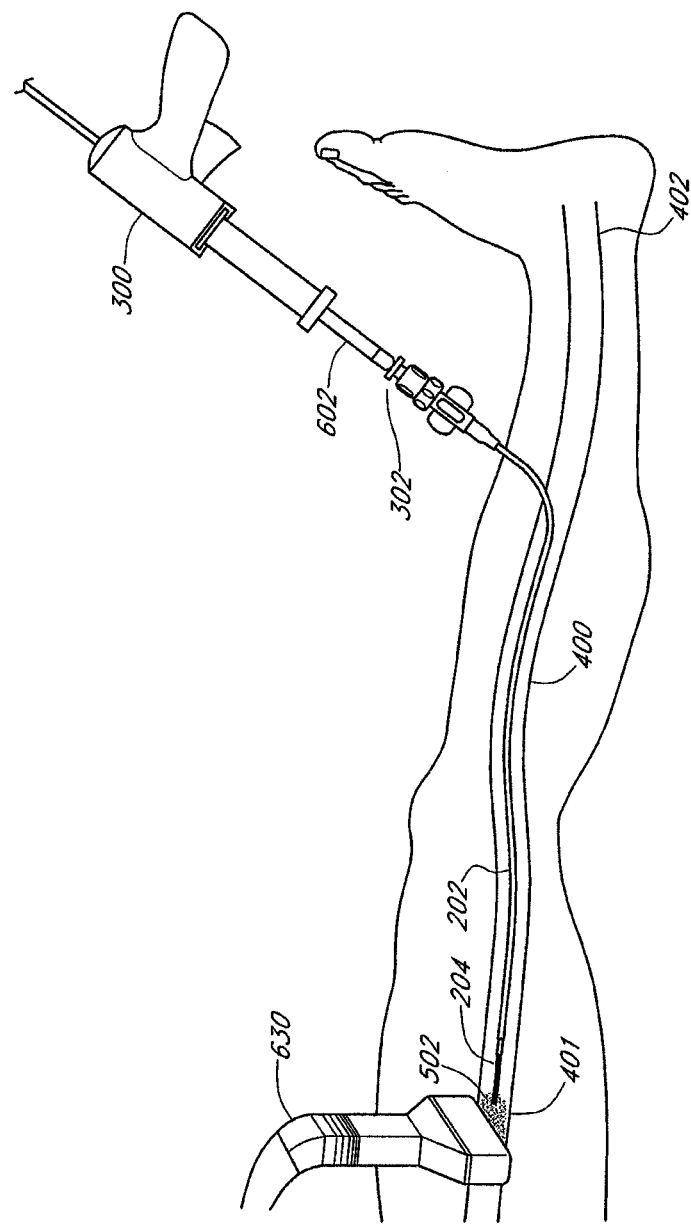

In accordance with FIG. 2, the tip of the inner catheter 204 is placed at a site adjacent to the blocked or distal end 401 of the vessel 400 with a minimum distance between them. Once the outer catheter 202 and inner catheter are in place, the glue gun 300 can inject a vein-occluding substance 502 that is released from the inner catheter 204. In some embodiments, the inner catheter 204 can release at least 1, 2, 3, 4, 5, 7, 10, 12, 15, 20, or more boluses of vein-occluding media along a treatment site within a vein. For example, in some embodiments, a single continuous flow of vein-occluding media can be introduced across a treatment site, while in other embodiments, multiple spaced-apart boluses of vein-occluding media can be introduced at regular or irregular intervals across a treatment site. In some embodiments, the treatment site can be a total length of between 2 cm and 50 cm, or between about 5 cm and 40 cm in some embodiments. Along the treatment site, one or more boluses of vein-occluding media can be introduced at spaced-apart intervals, such as between every 1 cm and 7 cm, more preferably between every 3 cm and 5 cm. The intervals need not be evenly spaced. Each bolus of media can occlude and treat at least a portion of the treatment site. In some embodiments, a single bolus of media can occlude and treat a length of the vein that is between 0.5 cm to 5 cm, such that at least about 0.5 cm, 1 cm, 2 cm, 3 cm, 4 cm, or 5 cm of the vein can be treated. In other embodiments, the length of the treatment site within the vein will be greater than 5 cm by a single bolus of media. Providing one or more boluses of vein-occluding media, particularly in selected intervals, as described herein advantageously provides a treatment that can be performed with greater control and ease over conventional vein-occluding processes and which can be tailored to specific patients (e.g., having different lengths of treatment zones).

In some embodiments, each bolus of media can have a volume of between 0.01 to 3 cc of a vein-occluding substance (e.g., cyanoacrylate compound), such as between 0.01 cc to 1 cc of a vein-occluding substance. The rate of injection can be controlled manually, or by a mechanical and/or electronic controller configured to release a predetermined volume of vein-occluding substance at a specified flow rate. While in some embodiments the injection rate can be relatively constant throughout the procedure in some embodiments, in other embodiments, the injection rate can be variable, releasing periodic boluses of vein-occluding substance at specified time and/or distance intervals. In some embodiments, the injection rate is between 0.002 cc/sec and 6 cc/sec, such as between about 0.02 cc/sec and 0.2 cc/sec. Controlling the volume and flow rate of the bolus of media to levels described herein advantageously prevents unnecessary overflow or undertreatment of the media within the vein. In some embodiments, an injector is provided that is configured to precisely deliver a predetermined volume of media, such as between about 0.05 mL and 0.5 mL, or between about 0.1 mL and 0.2 mL, into the vein when a physician actuates a control, such as a button, switch, dial, or foot pedal, for example. In some embodiments, the injector includes a safety feature, such as an electronic lockout that prevents unintended multiple bolus injections of glue within a specified period of time, such as, for example, requires that bolus injections be spaced apart by at least about 0.5, 1, 2, 3, 4, 5 seconds, or more.

Figure 3:
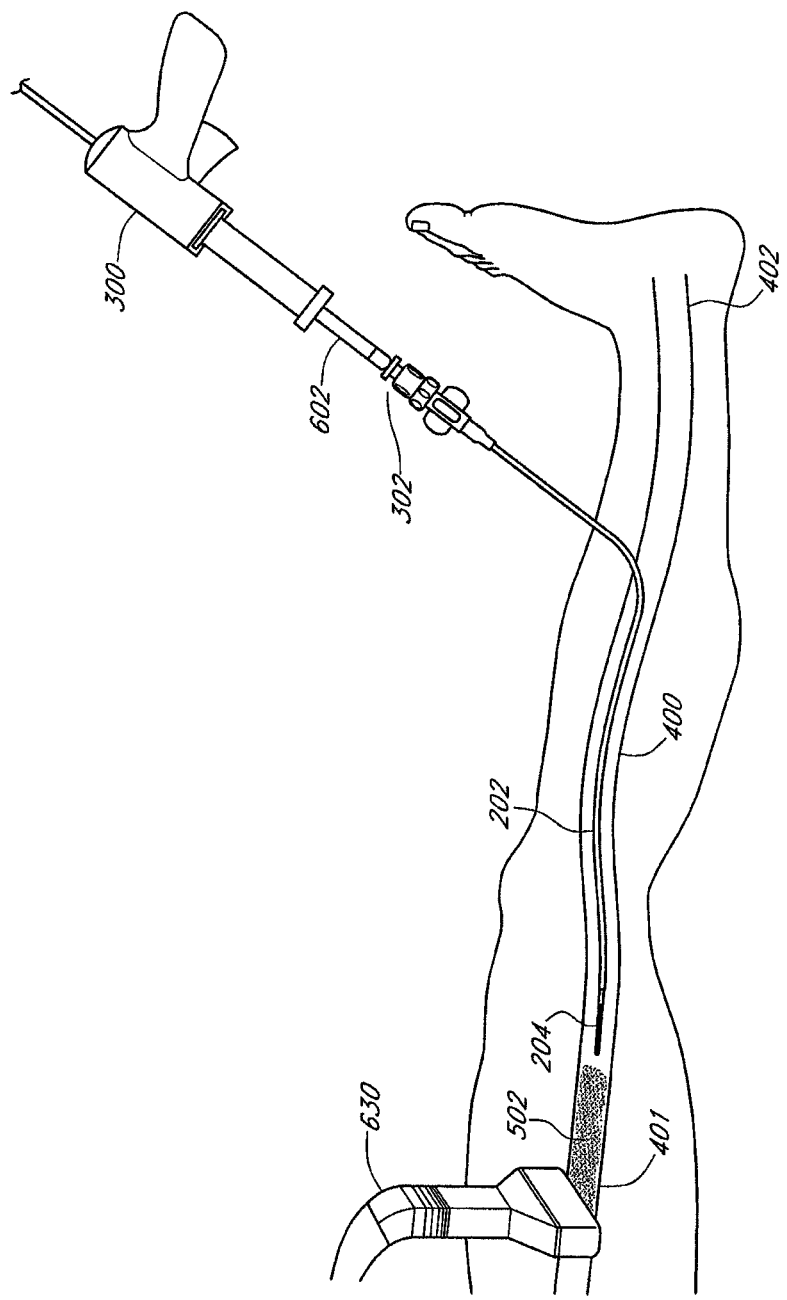

In accordance with FIG. 3, once the vein-occluding substance 502 is injected out of the tip of the inner catheter 204, the vein-occluding substance 502 flows against the distal end of the proximal side of the occluded vessel 400 and then reverses flow proximally traveling along the outside of the catheter track while displacing the blood content along the target area of the vessel 400. Then, the outer catheter 202 and inner catheter 204 can be pulled back or withdrawn to target a different site along the vessel 400. For example, the outer catheter 202 and inner catheter 204 can be moved in a direction towards the proximal end 402 of the vessel 400 prior to injecting additional vein-occluding substance 502 into the vessel 400.

Figure 4:
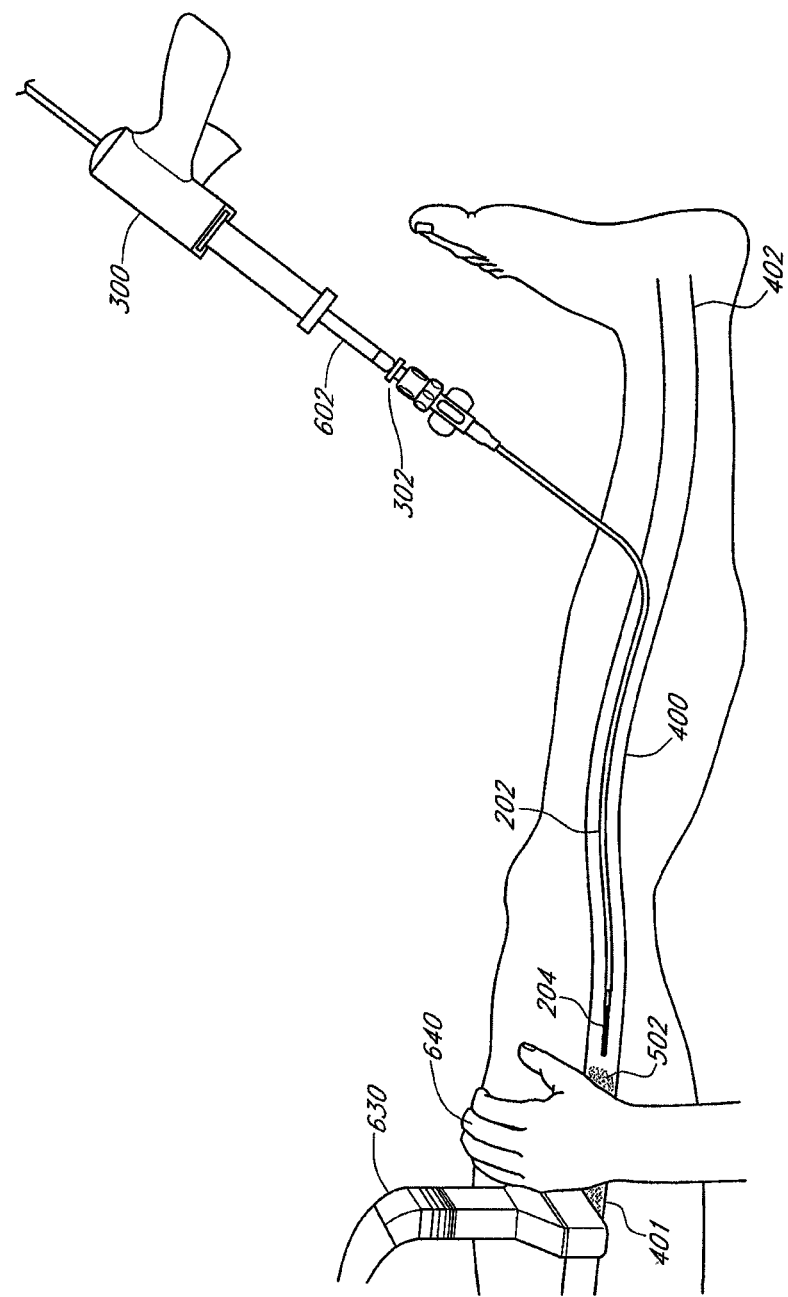

In accordance with FIG. 4, an optional compression element, e.g., an operator's hand 640, a sequential compression device, or the ultrasound transducer 630 can be used to apply pressure on the external surface of the patient's body and compress the interior walls of the vessel 400. The optional compression element can be used to compress portions of the vessel prior to, during or after the introduction of the vein-occluding substance. When the compression element compresses portions of the vessel during or after the introduction of the vein-occluding substance, the vessel is compressed against the vein-occluding substance 502, as shown in FIG. 4. This compression assists in occlusion as well as collapse of the vessel. In some embodiments, as additional portions of the vessel are treated with the vein-occluding substance, the target regions can be compressed immediately following, or no more than about 5 minutes, 4 minutes, 3 minutes, 2 minutes, 1 minute, 30 seconds, 15 seconds, or less following injection of the vein-occluding substance in some embodiments.

Figure 5:
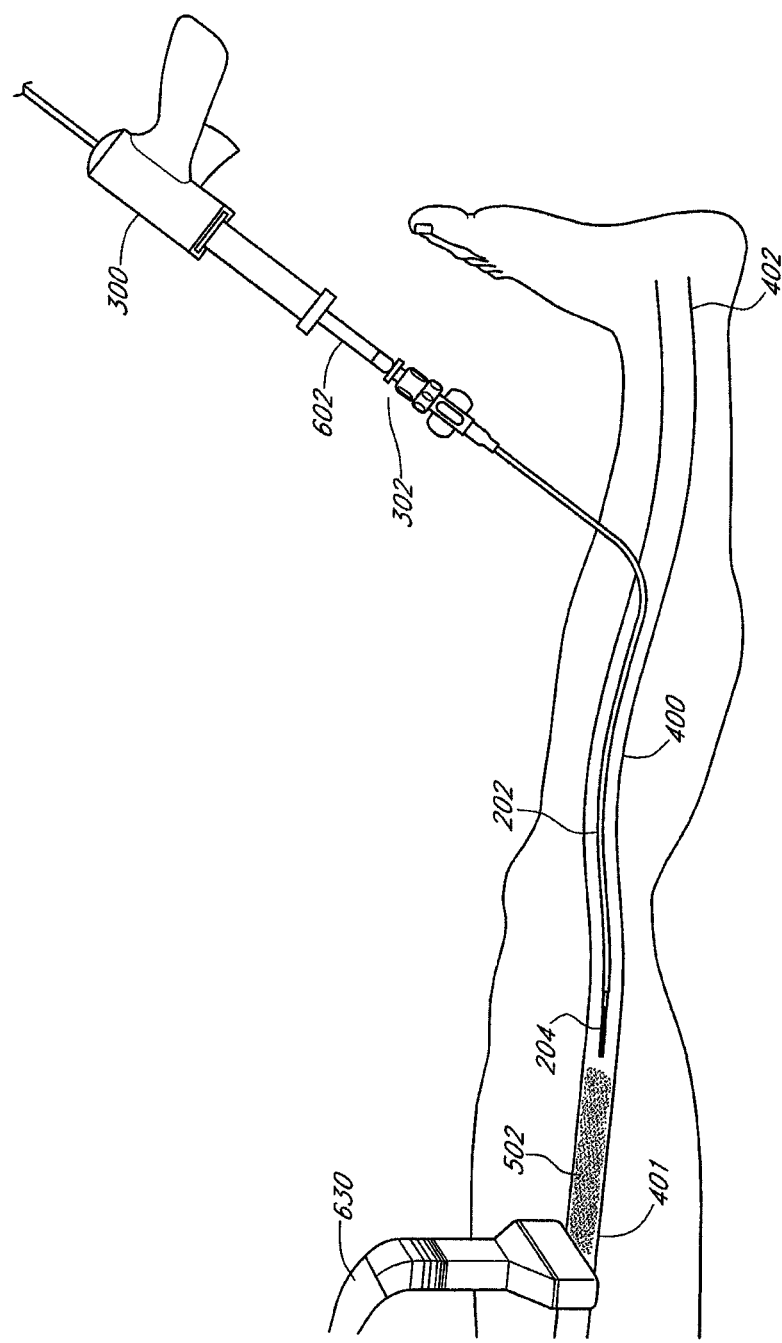
Figure 6:
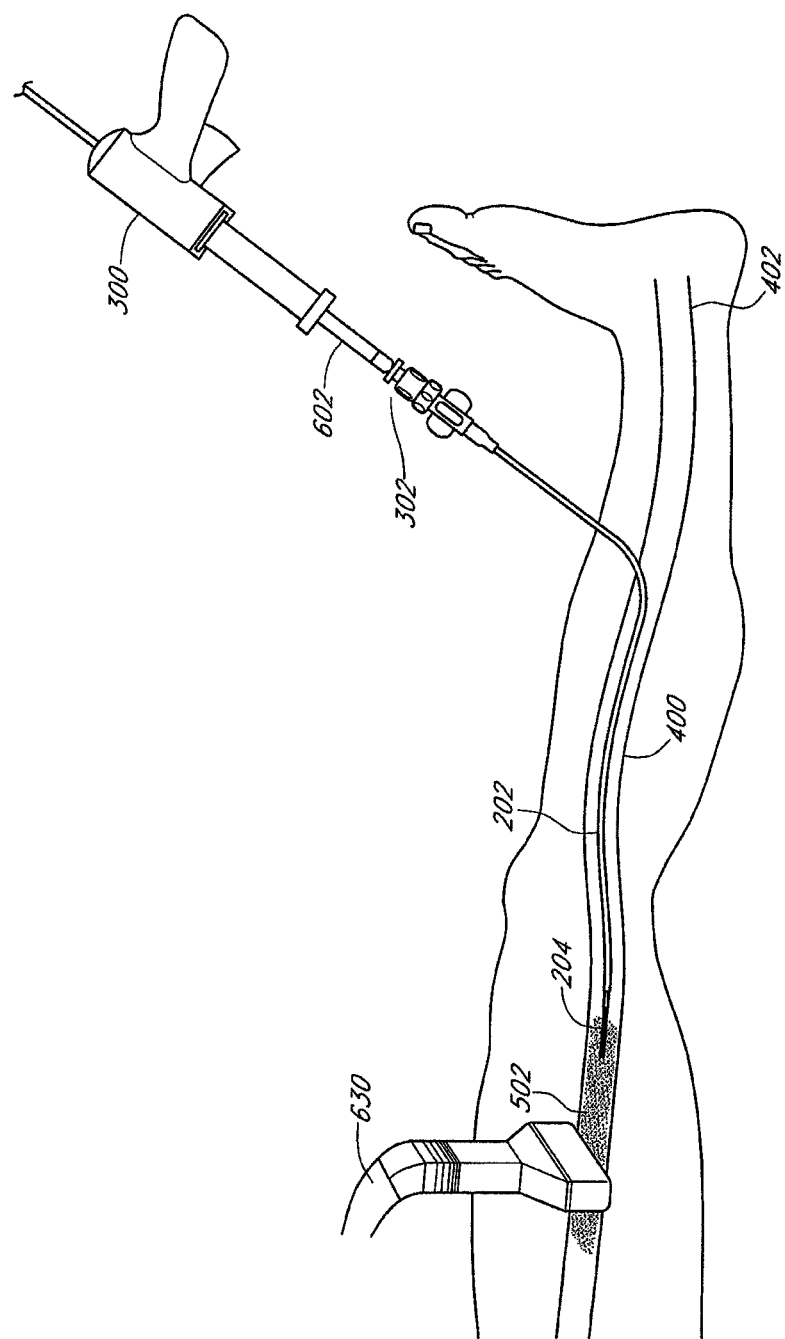
Figure 7:
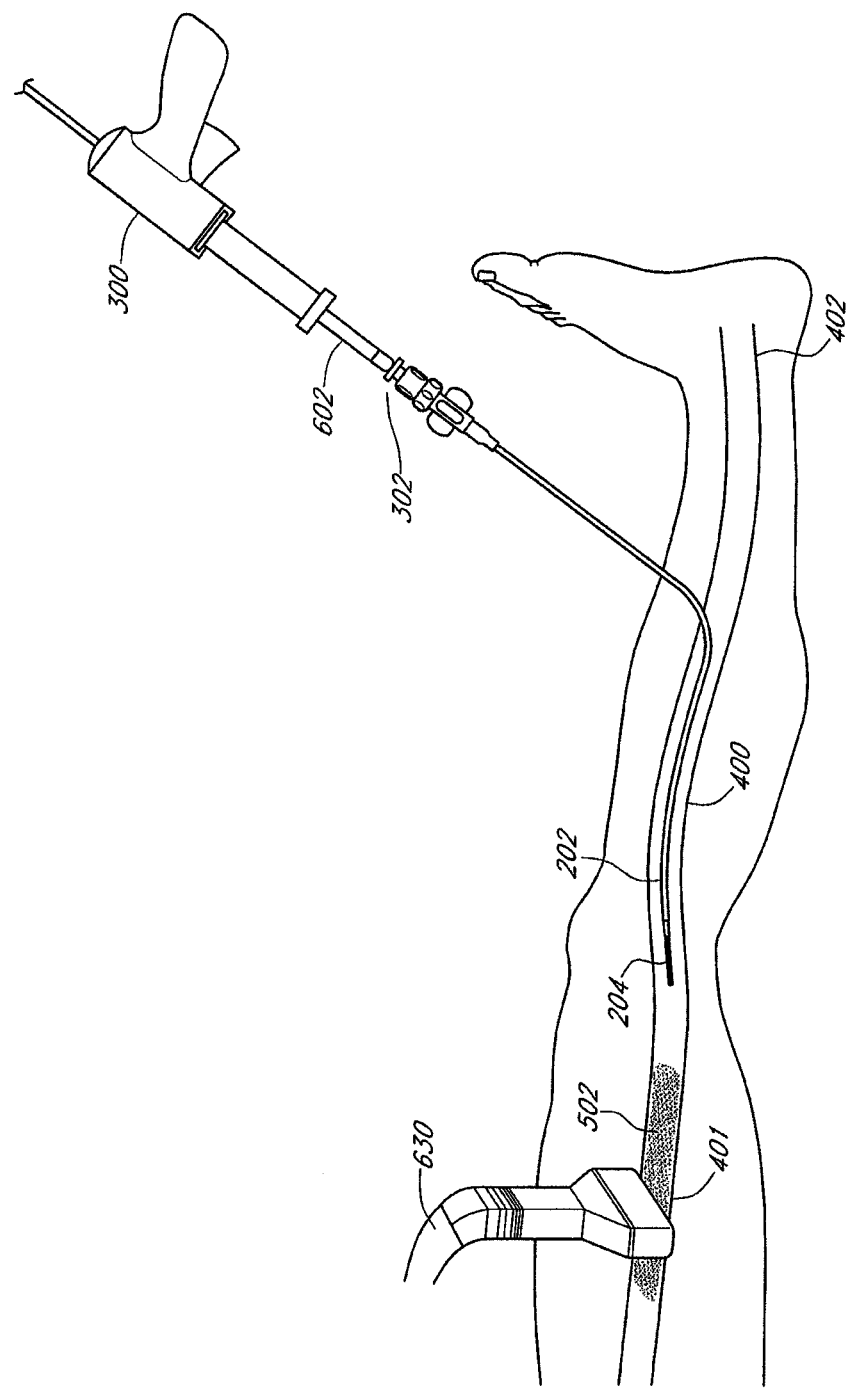

FIGS. 5-6 illustrate the ultrasound transducer 630 guided or moved from a first location to a second location following injection of the vein-occluding substance 502 at the first site. Once the vein-occluding substance 502 is injected to a targeted site and preferably, once the vein is completely occluded and/or collapsed at that site, the ultrasound transducer 630 can be moved to a second location, e.g., a location closer towards the proximal end 402 of the vessel 400, to assist in collapse of the vessel 400 at a different site. In some embodiments, by moving the ultrasound transducer 630 along the length of the vessel 400 in a proximal direction, the ultrasound transducer can serve as a compression element that provides a compression that follows the length of the vessel 400 in a proximal direction to better ensure collapse of the vessel. In some embodiments, the ultrasound transducer or other external compression element can be moved a distance between the first location to a second location spaced apart between 0.5 cm to 5 cm with respect to the first location. In other embodiments, the ultrasound transducer can be moved a distance between the first location to a second location that is between 3% and 50%, such as between 3% and 20% of the total length of the treatment site. Guiding the ultrasound transducer over a discrete distance advantageously helps to ensure that portions of the treatment site are effectively occluded before guiding the ultrasound transducer over different portions of the treatment site. After moving the ultrasound transducer 630, the glue gun 300 can inject a vein-occluding substance 502 at the different site of the vessel 400, as shown in FIG. 6.

Figure 8:
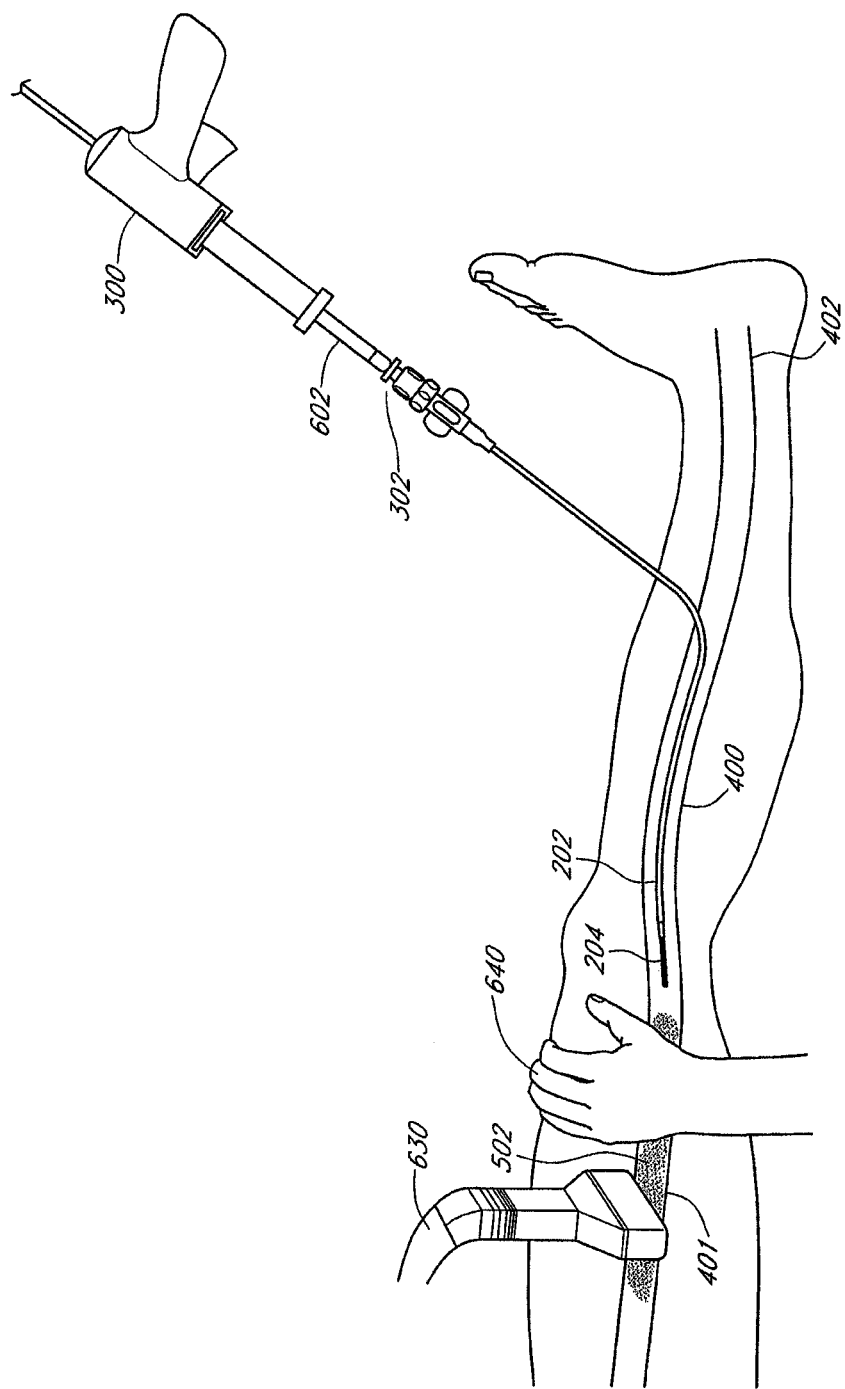
Figure 9:
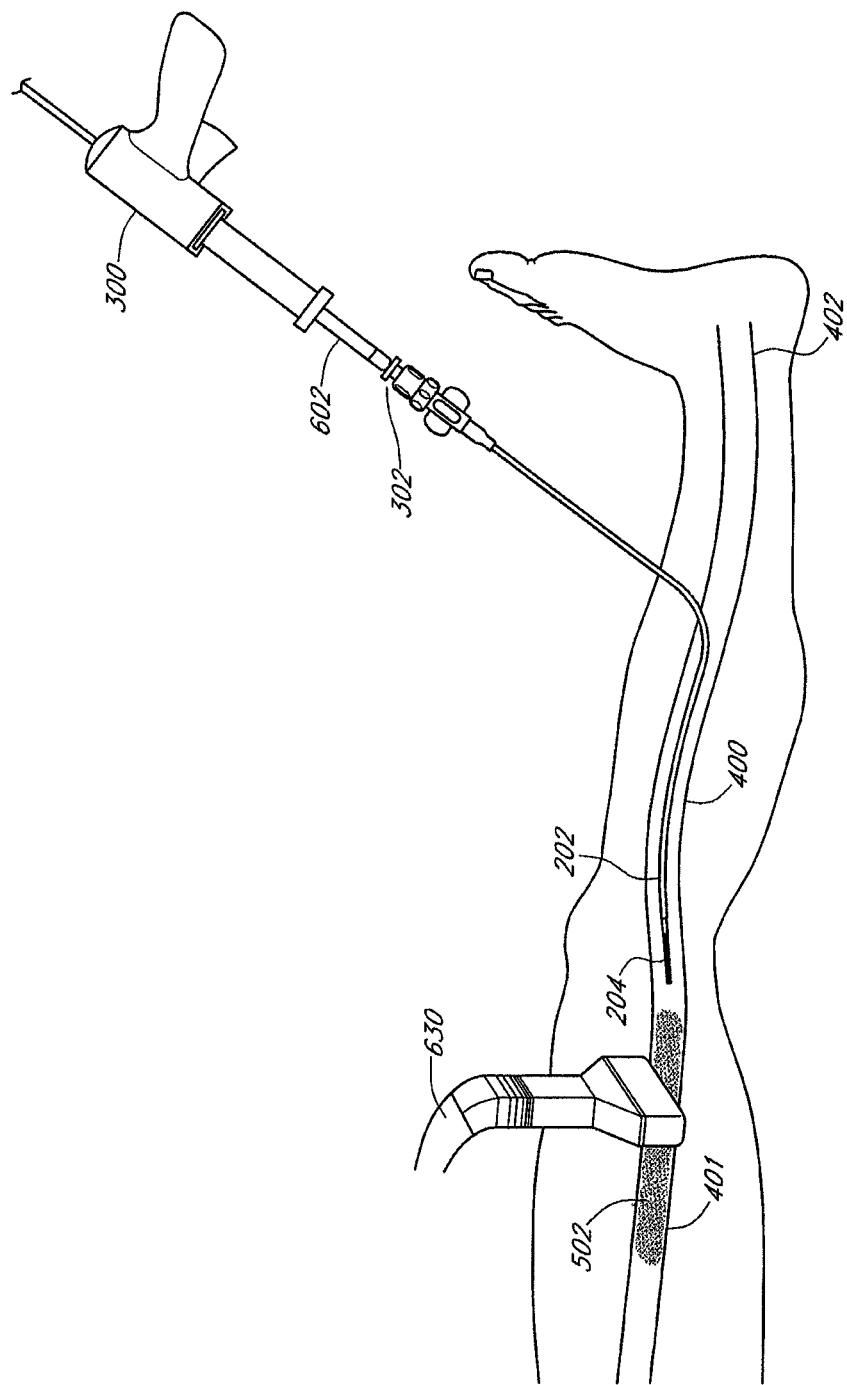

Once the vein-occluding substance 502 is injected into the second site of the vessel 400, a compression element e.g., the hand 640, can once again be used to assist in collapse of the portion of the vessel 400, as shown in FIG. 8. After achieving partial or complete closure of a portion of the vessel 400, the ultrasound transducer 630 can once again be guided or moved along the vessel 400 to different locations to assist in closure or occlusion of the vessel 400, providing a moveable compression element in some instances. With the assistance of the ultrasound transducer 630 and/or additional compression element as described above, which can move along the length of the vessel 400 and serve as a compression element and/or image generator, it is possible to collapse the vessel 400 along the entire treatment length. As shown in FIG. 9, the ultrasound transducer 630 is guided to the second location along the vein 400 to assist in collapse of the vessel 400 at the different location.

Figure 10:
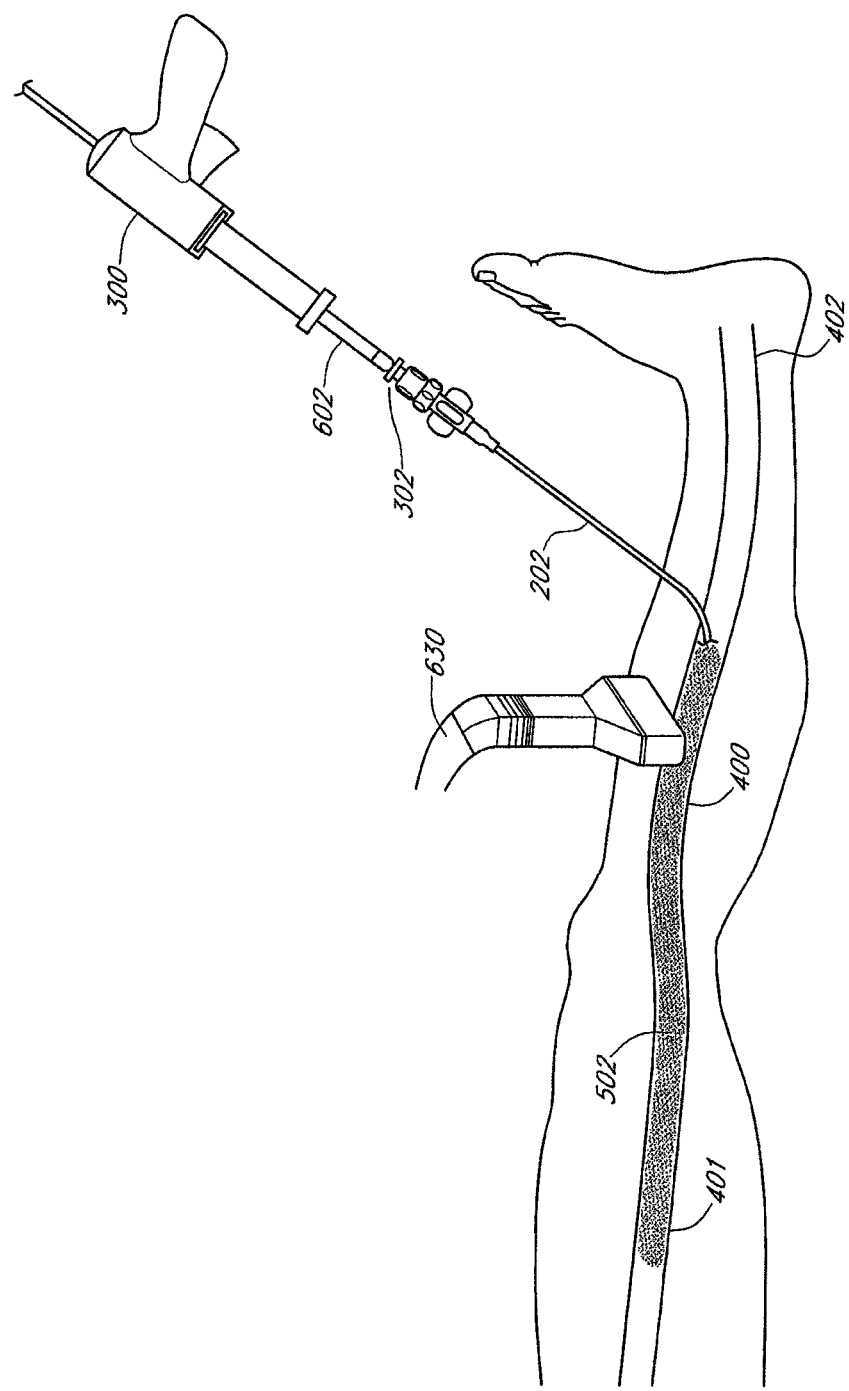
Figure 11:
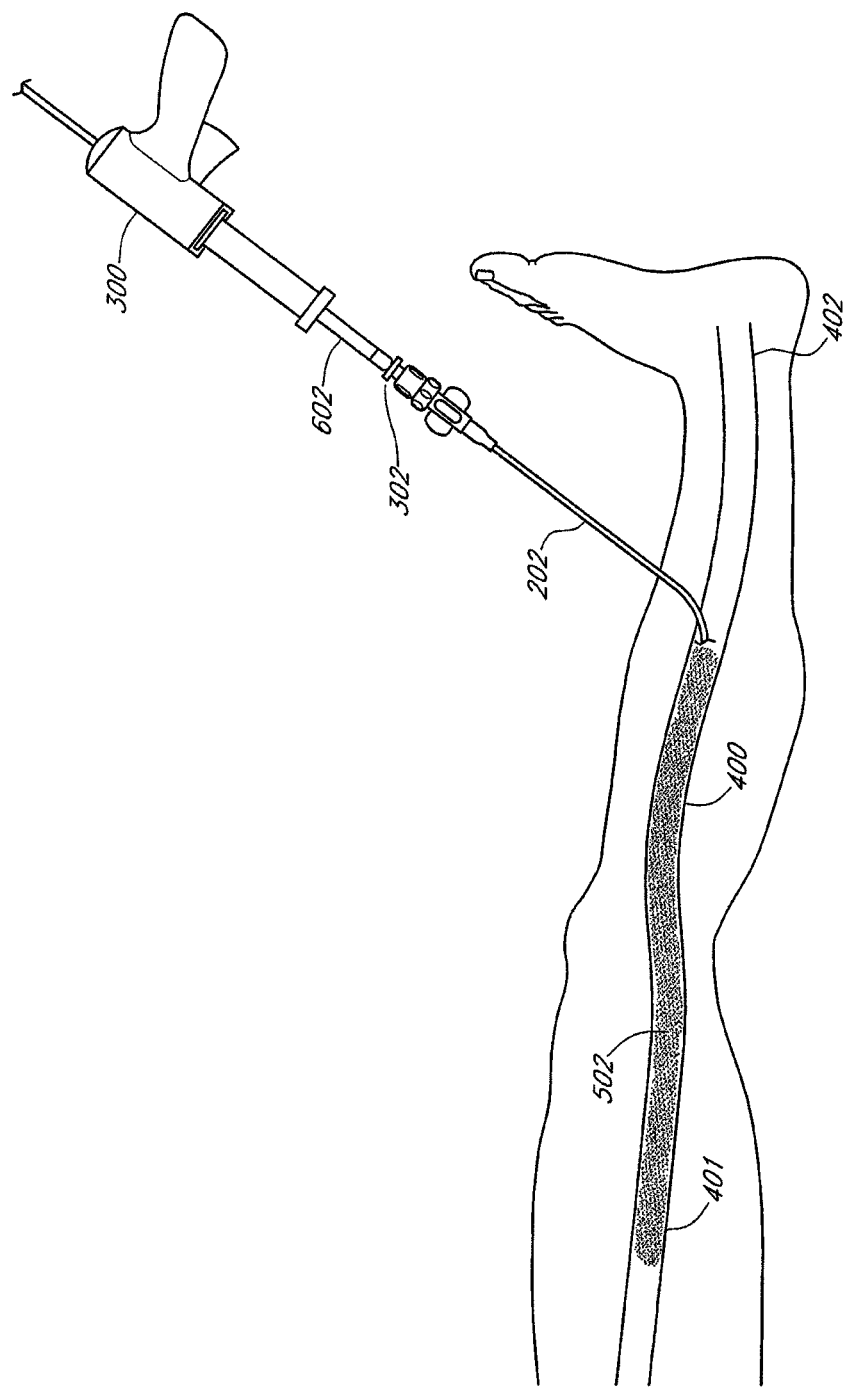

The application of the ultrasound probe and/or additional compression device can be repeated at multiple locations along the greater saphenous vein, as shown in FIGS. 10-11, until the vein is partially or entirely co-apted and closed in a flattened state. The inner catheter can then be removed, and a band-aid or other dressing can be placed over the entrance site. In some embodiments, the ultrasound probe can generate images that reconfirm the closure or co-apting of the flattened vein. Once the flattened vein is closed partially or completely, the injector is removed from the access site, and the procedure then is completed. In one embodiment, only a small amount of local anesthesia at the entrance site is used. No tumescent anesthesia is required. No general or conscious sedation is required as the procedure produces no significant heat or other types of damage to surrounding tissues.

While the methods above have been described with the intention of occluding the great saphenous vein, a wide variety of other veins, arteries, lymphatics, or other body lumens, natural or artificial can be occluded as well using systems and devices as disclosed herein. Furthermore, a variety of conditions can be treated with the systems, devices, and methods disclosed herein, for example, venous insufficiency/varicose veins of the upper and/or lower extremities, esophageal varices, gastric varices, hemorrhoidal varices, venous lakes, Klippel-Trenanay syndrome, telangiectasias, aneurysms, arterio-venous malformations, embolization of tumors or bleeding vessels, lymphedema, vascular and non-vascular fistulas, closure of fallopian tubes for sterilization, etc.

In some embodiments, the vein-occluding substance can be injected into the vein using an automated process in order to minimize undesired over-injection or under-injection of the vein-occluding substance, injection at undesired intervals or injection of undesired bolus sizes. For example, the outer catheter member of the catheter can be made easily compressible (e.g., with a thin wall). The column strength needed for catheter placement can thus be supplied predominantly with the inner tube. Once the inner catheter has been withdrawn from the vein, the remaining outer catheter is filled with the vein-occluding substance. The proximal end of the outer catheter just distally of the luer lock, manifold, or other coupling to the vein-occluding substance injector can carry a compression element such as a clamp, parallel rollers, or a slideable element with the catheter extending transversely between two portions of the slideable element. Actuating the compression element will radially compress the outer catheter. An operator can then hold the clamp in place while the catheter is pulled proximally through the clamp. The clamp thus slides, rolls, or otherwise moves along the tube, while the catheter is compressed to precisely express the volume of the catheter as a function of the distance the catheter is withdrawn proximally from the vein.

Figure 12:
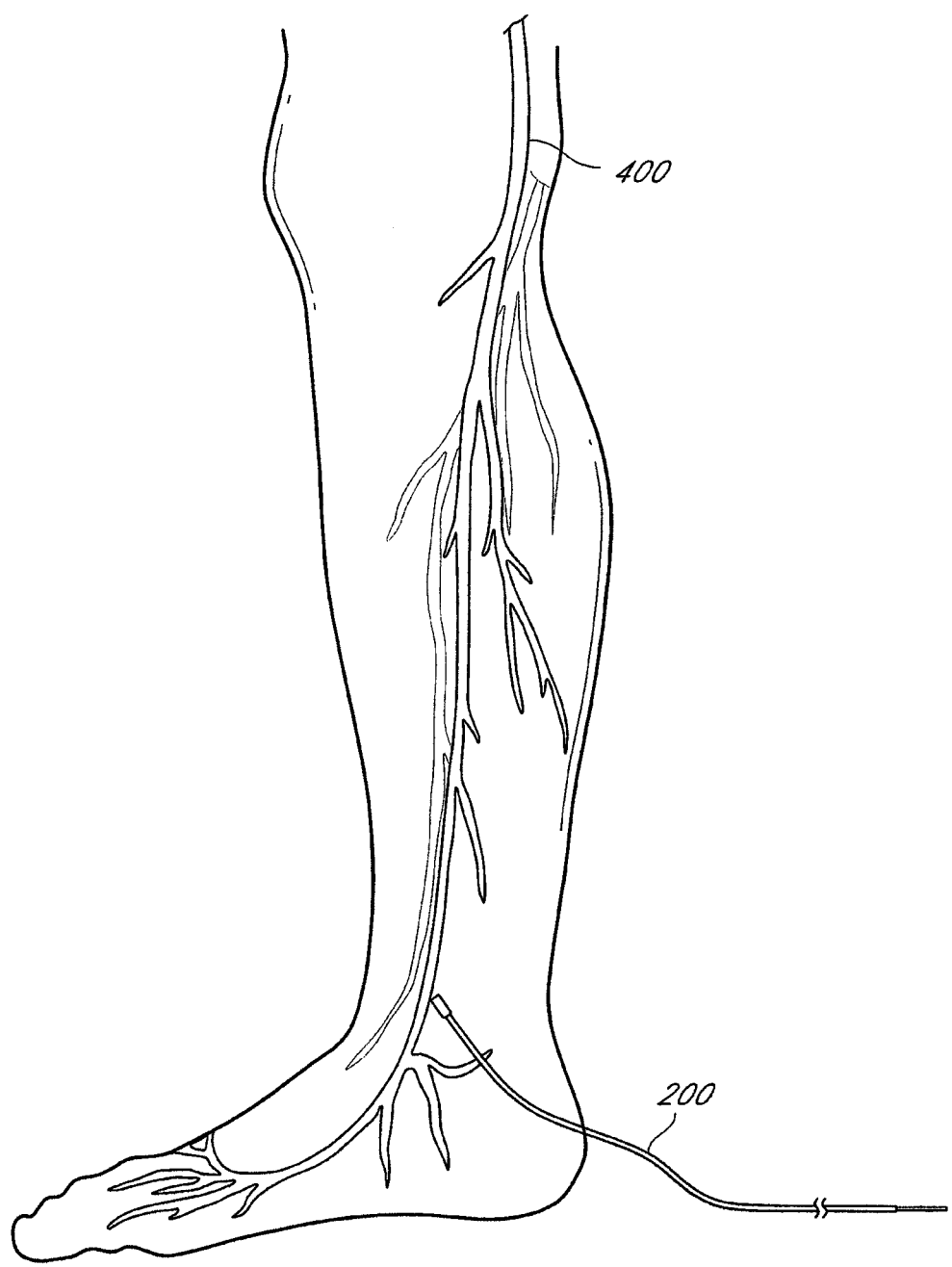
FIGS. 12-16 schematically illustrate a method for occluding a vein, such as the great saphenous vein, according to another embodiment of the invention.
Figure 13:
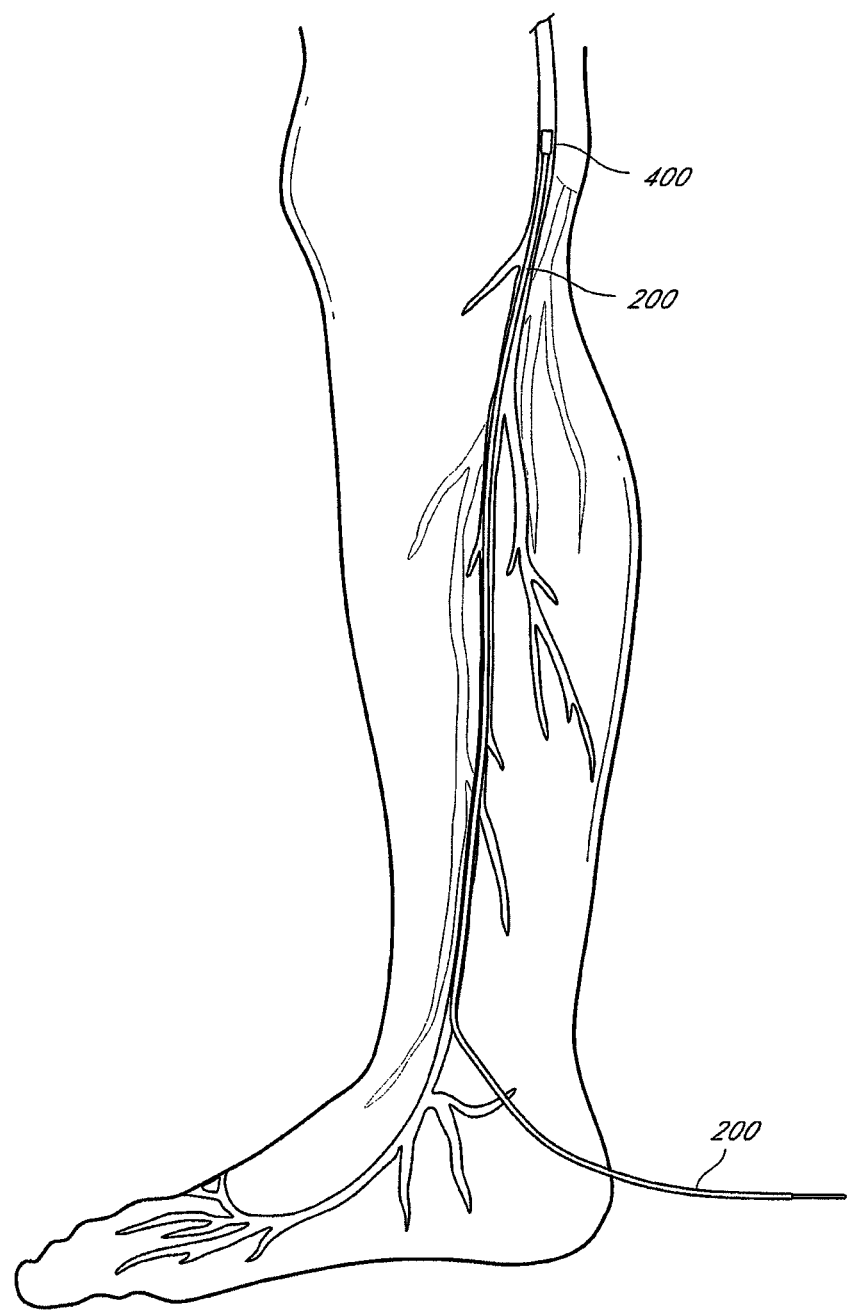
Figure 14:
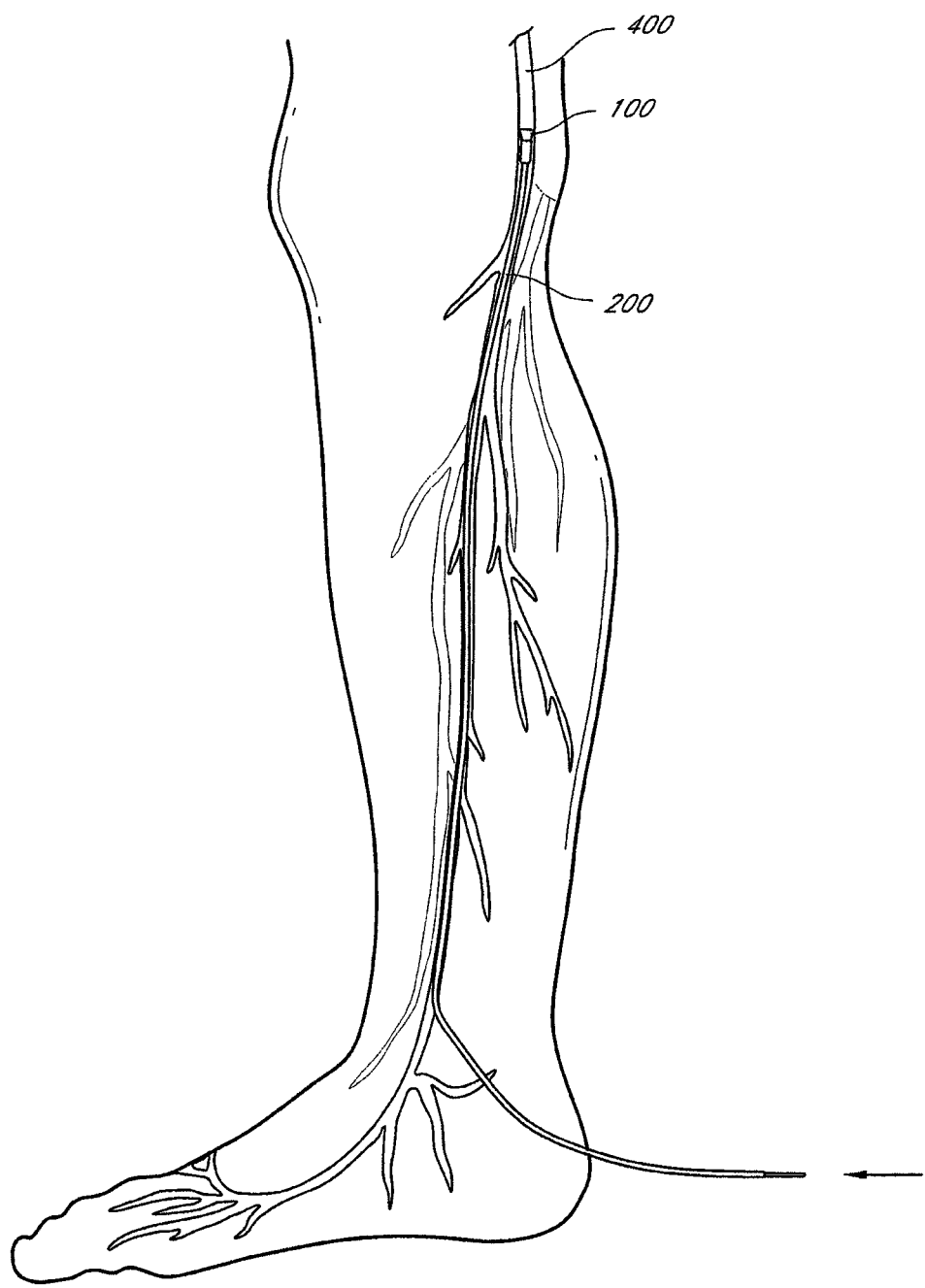
Figure 15:
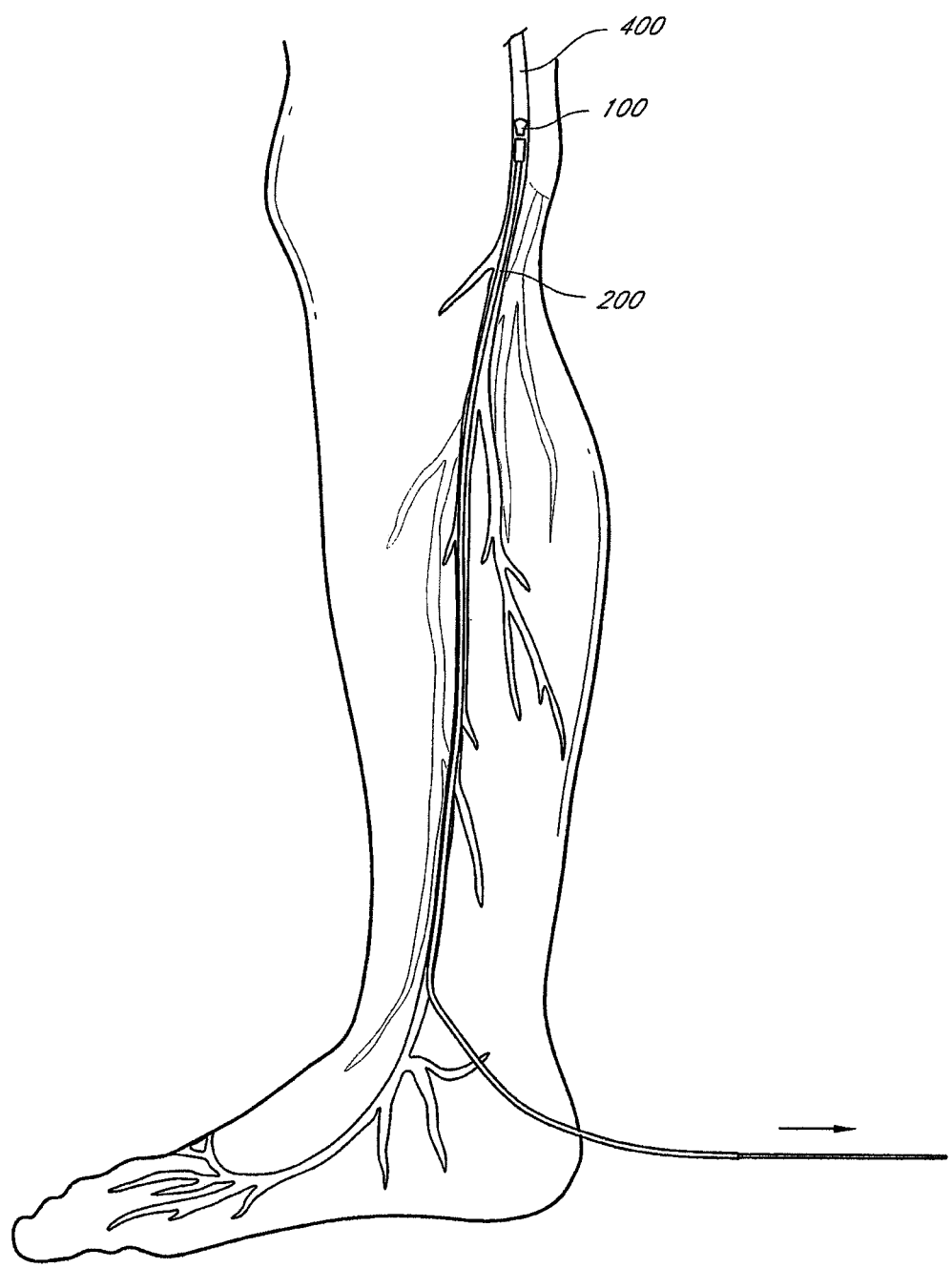

FIGS. 12-16 schematically illustrate a method for occluding a vein, such as the great saphenous vein, according to one embodiment of the invention. Ultrasonographic vein mapping, contrast venography, or other technique, for example, can be used prior to the occlusion procedure to better visualize a patient's particular vascular anatomy in some embodiments. The entry site is prepped and draped in a sterile fashion, and local anesthesia such as Lidocaine can be provided, although may not be required. First, the vascular system, such as a superficial vein in the foot, ankle, or calf, for example, a dorsal digital vein, intercapitular vein, common digital vein, dorsal venous arch, medial marginal vein, lateral marginal vein, plantar cutaneous venous arch, or a vein of the plantar cutaneous venous network is cannulated, such as percutaneously or alternatively through a cut-down procedure. Any of these veins can also be occluded using the systems and methods described herein. Imaging such as ultrasound or fluoroscopy, for example, can be used for access assistance. A guidewire (not shown) can then be inserted into the vessel. A sheath or introducer, such as a needle, can also be placed to facilitate catheter entry into the appropriate vein. Next, a delivery catheter 200, including inner catheter member and outer catheter member, as well as housing an occlusion device such as described above can be inserted into the vessel as shown in FIG. 12 via, for example, the Seldinger technique over a guidewire. The catheter 200 is then advanced distally into the venous system to a desired location, such as within the great saphenous vein (or small saphenous vein or accessory saphenous vein) as shown in FIG. 13. The inner catheter can then be actuated relative to the outer catheter to deploy an occlusion device 100 to its expanded configuration within the desired location within the vein 400. The occlusion device can in some embodiments include components as described, for example, in U.S. Provisional Application No. 61/154,322, filed on Feb. 20, 2009, and herein incorporated by reference in its entirety, including (but not limited to) those having tissue anchors or bars or other features for engaging vessel walls. In some embodiments, the occlusion device can include components as described with respect to FIGS. 36-44. FIG. 14 illustrates the inner catheter being advanced in preparation to deploy an occlusion device 100. Once desired placement is confirmed, the detachment mechanism such as a suture (not shown) is then actuated to release the occlusion device 100 within the vessel. Deployed anchors on the frame portion of the occlusion device 100, can prevent migration of the occlusion device 100 from the desired location within the vein 400. Next, the inner catheter can be withdrawn, as illustrated in FIG. 15.

Figure 16:
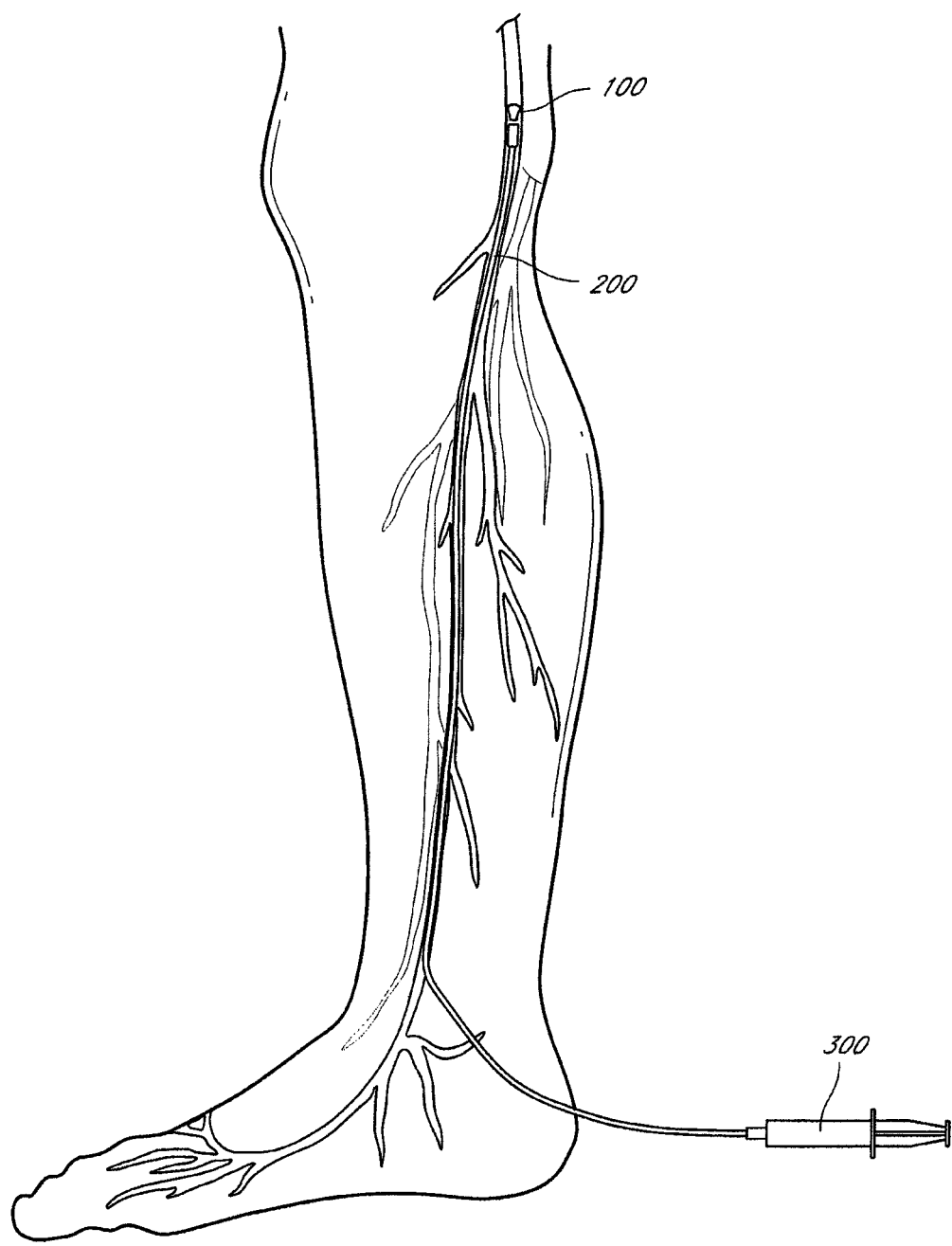

After withdrawal of the inner catheter, a vein-occluding substance such as described above can be injected through the outer catheter into the vein 400 proximal to the deployed occlusion device. As illustrated in FIG. 16, the outer catheter can then be withdrawn while the vein-occluding substance continues to be injected, in order to occlude the vein in a proximal direction relative to the occlusion device. The outer catheter can then be fully withdrawn, and an external compression stocking applied, completing the procedure. Percutaneous closure methods can also be utilized in some embodiments. In some embodiments, 0.01 cc to 1 cc of vein-occluding substance, e.g., a cyanoacrylate compound, can be injected over a distance of 0.5 cm to 5 cm of vein, such as at least about 0.5 cm, 1 cm, 2 cm, 3 cm, 4 cm, or 5 cm of vein to be treated. The injection rate can be relatively constant throughout the procedure in some embodiments, or variable, releasing periodic boluses of vein-occluding substance at specified time and/or distance intervals. Withdrawal through the vein to be treated can take place, for example, over a period of 30 seconds to 5 minutes in some embodiments, or about equal to, or less than about 10, 9, 8, 7, 6, 5, 4, 3, 2, 1 minute, 45 seconds, or 30 seconds in some embodiments.

Figure 17:
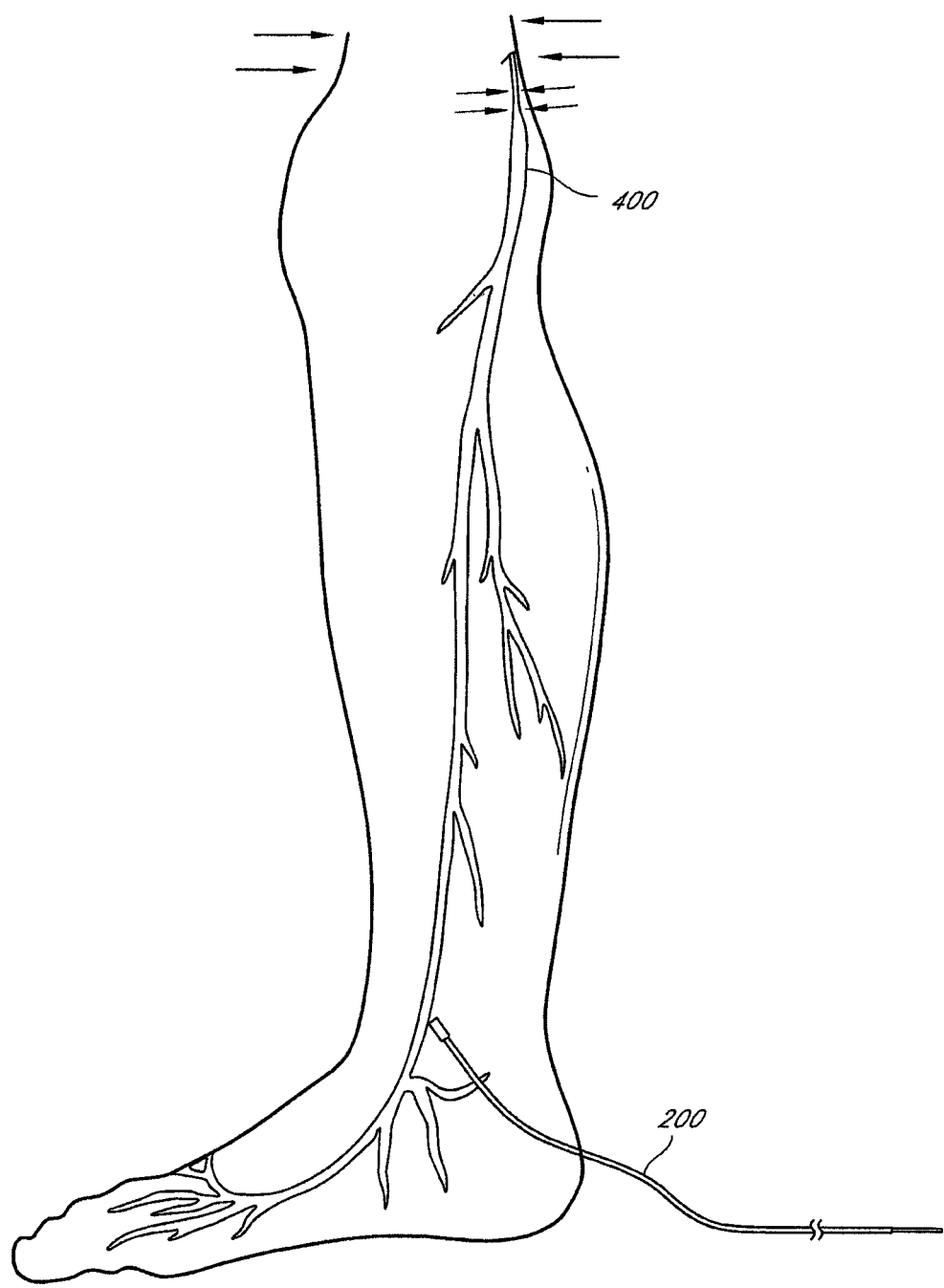
FIGS. 17-21E schematically illustrate methods for occluding a vein, such as the great saphenous vein, according to another embodiment of the invention.
Figure 18:
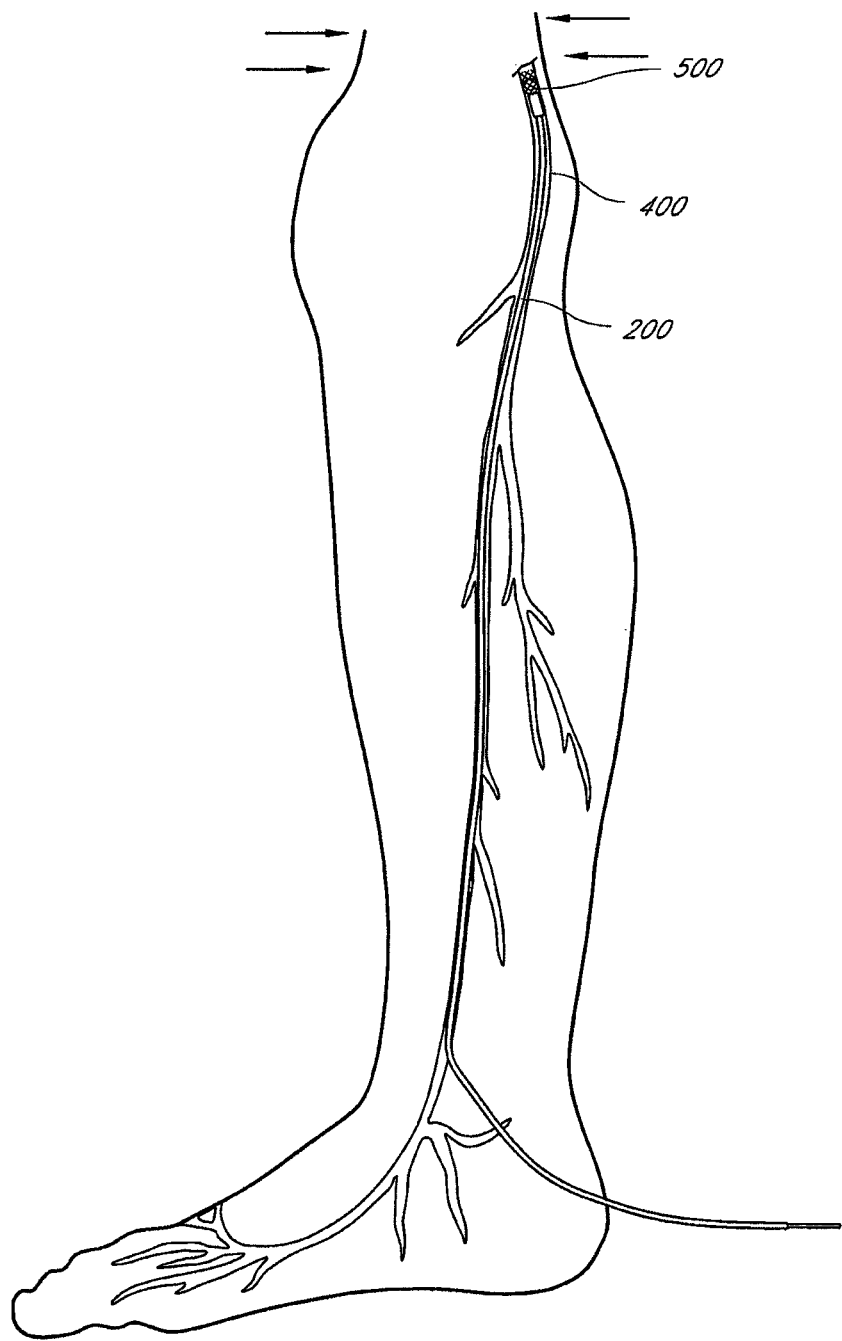

A method of occluding a vein utilizing a vein-occluding substance as an occluding member according to some embodiments will now be described in further detail. First, a catheter can be deployed to a desired location in a tubular structure such as a vein as illustrated and described in connection with FIGS. 12 and 13 above. The vein 400 can then optionally be compressed, either before or after placing the catheter, such as by, for example, external manual compression of the leg or with a tourniquet or other type of compression device at a distal location as shown schematically with arrows in FIG. 17. Next, a vein-occluding substance can be injected at a first location within the vein 400 to serve as an occluder 500, as shown in FIG. 18, to prevent embolization more distally. External compression prior to and at a location just distal to the injection site can advantageously help to prevent migration of the formed in situ occluder 500 prior to polymerization or other fixation process. Compression can also prevent unwanted embolization distally into more central veins, as well as induce retrograde flow of the vein-occluding substance proximally when the vein-occluding substance, upon distal ejection from the catheter, contacts the vein at the point that is collapsed from compression, forcing the vein-occluding substance to flow proximally. In some embodiments, the distance from the exit port on the catheter where the vein-occluding substance is ejected to the area of the vein that is collapsed from compression is no more than about 3 cm, 2.5 cm, 2 cm, 1.5 cm, 1 cm, 0.75 cm, 0.5 cm, 0.25 cm, or less.

The vein-occluding substance serving as an occluder 500 can be, for example, a larger-volume bolus of a vein-occluding substance compared to a volume of vein-occluding substance injected more proximally over a specified period of time and/or length of vein, of which specific ranges are described above. The initial bolus can be at least about 0.1 cc, 0.25 cc, 0.5 cc, 0.75 cc, 1 cc, 1.5 cc, or more in some embodiments, or between about 0.05 mL and about 0.9 mL, between about 0.05 mL and about 0.5 mL, or between about 0.1 mL and about 0.2 mL in other embodiments The initial bolus can be at least about 10%, 25%, 50%, 75%, 100%, 150%, 200%, or more greater than a volume of vein-occluding substance injected more proximally over a similar length of vein.

In addition to, or instead of a large bolus volume of vein-occluding substance as described above, a second vein-occluding substance with different properties than a first vein-occluding substance used to treat the vein more proximally can also be used as an occluder. The second vein occluding substance is deployed first, to form the distal vein block. The first vein occluding substance is then dispensed along the length of the treatment site as the catheter is proximally retracted.

The second vein-occluding substance can be, for example, a glue or other occlusive medium that expands to a greater volume, hardens more rapidly, and/or has a shorter polymerization time relative to the first vein-occluding substance. In some embodiments, the second vein-occluding substance can be partially or completely bioresorbable. If multiple different vein-occluding substances are used, the catheter can be configured to have two or more lumens to accommodate delivery of the different vein-occluding substances. Alternatively the first and second occluding substances can be deployed sequentially via a common lumen.

Figure 19:
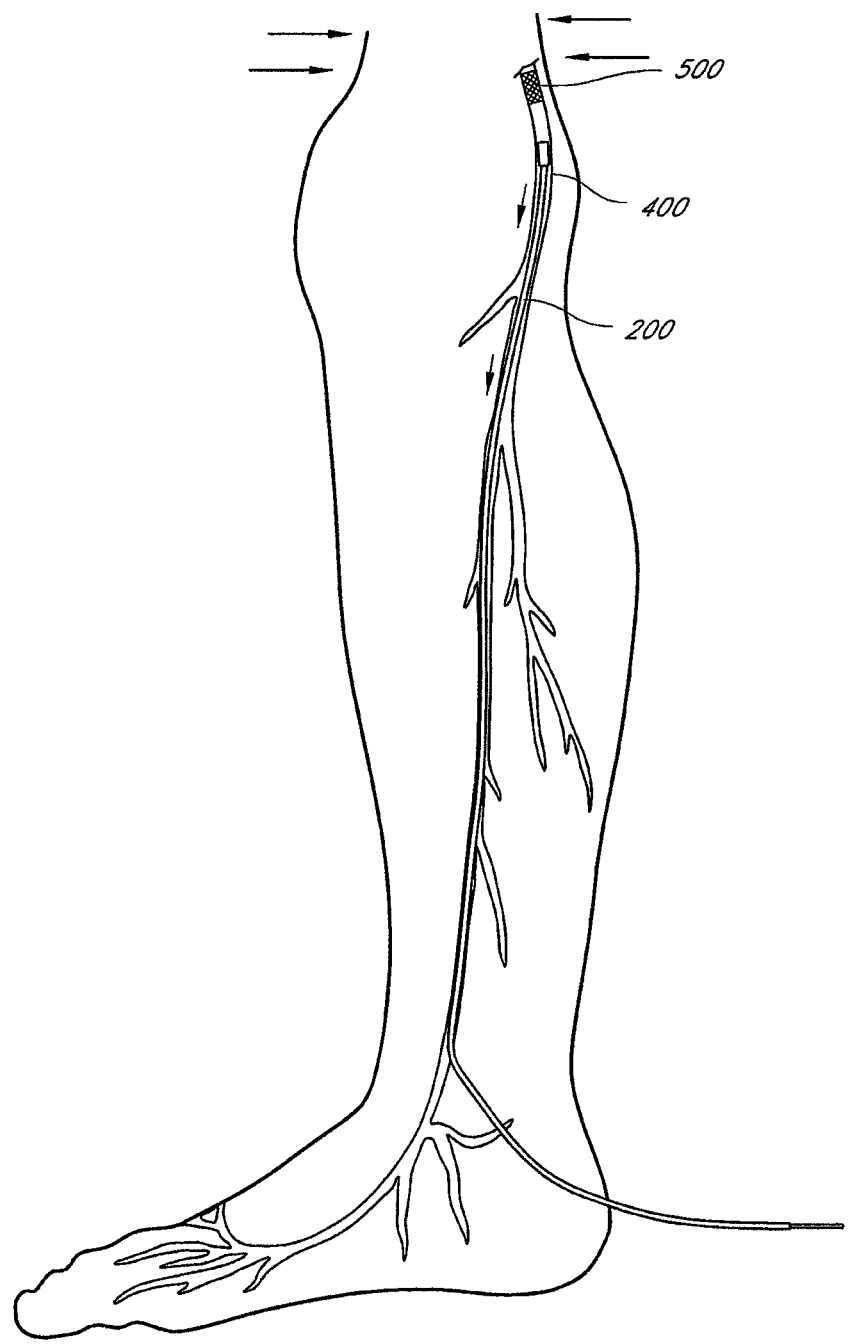
Figure 20:
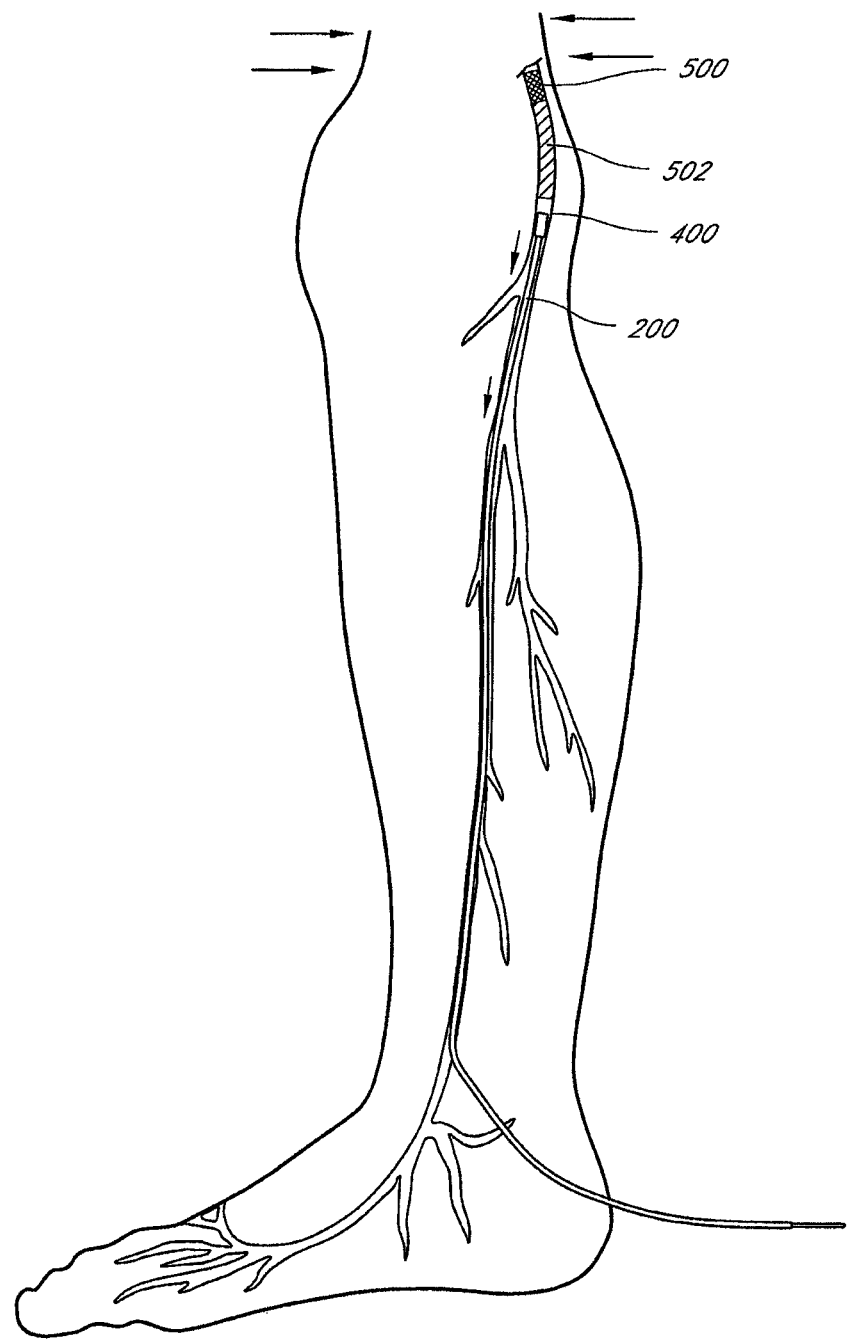
Figure 21:
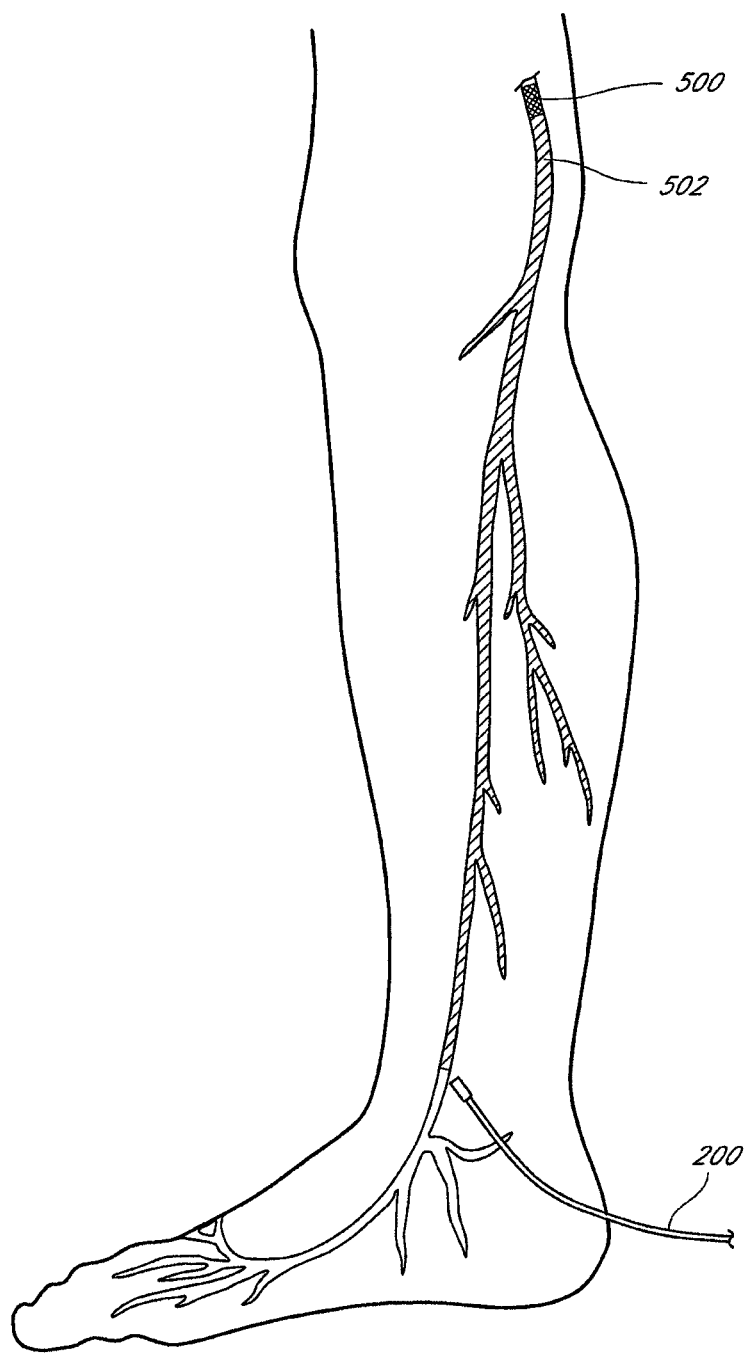

When the vein-occluding substance serving as a distal occluder hardens such that a plug 500 is formed to completely prevent blood flow distally as shown in FIG. 19, the catheter 200 can be withdrawn and the same or a different vein-occluding substance 502 as described above can be injected along the length of the vein segment to be treated to occlude the rest of the vein 400 to be treated while the catheter is withdrawn partially, and fully proximally as shown in FIGS. 20-21, respectively. As illustrated in FIG. 21, in some embodiments, 2, 3, 4, or more veins (that may be in some cases a branch of the first vein) can be treated during the procedure using a single puncture, or with 2, 3, 4, or more punctures.

Thus, in accordance with one implementation of the present invention, a deployment catheter 200 is percutaneously introduced into a vein at an access site, and translumenally distally advanced across a treatment zone within a vein. External compression, such as manual compression, is applied to collapse the vein distally of the deployment catheter and create a first occlusion. A bolus of plug forming media is expressed from the distal end of the catheter against a proximal side of the first occlusion, to form an occlusive plug 500 within the vein. External compression optionally may be removed, or may remain throughout the procedure. The catheter 200 is thereafter proximally retracted while dispensing a vein occluding substance 502 across the treatment zone, either continuously as a long stream, or intermittently at spaced apart intervals, where a second occlusion in the vein can be created, spaced apart from the first occlusion, and then a second bolus of media is introduced against the proximal side of the second occlusion External compression may be applied proximally, anywhere along the length of the vein, to ensure complete filling of the vein with the vein occluding substance 502. In some embodiments, a second, third, or more boluses of plug-forming media are progressively released into the vein more proximally at desired intervals, and external compression can be applied just distal to the point in which the catheter releases the plug forming media as described above. The catheter 200 is thereafter withdrawn, and the access site closed using conventional techniques.

Figure 21A:
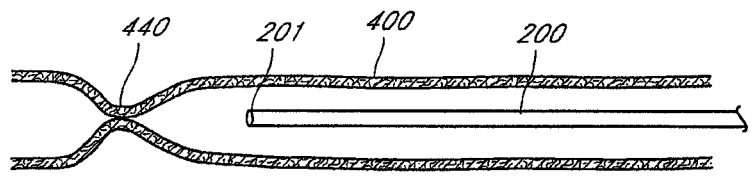
Figure 21B:
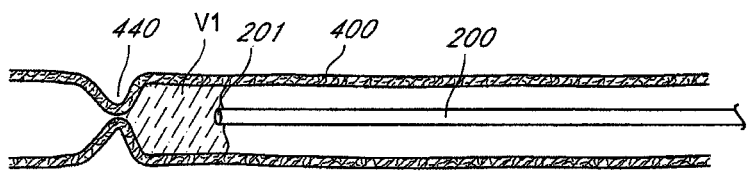
Figure 21C:
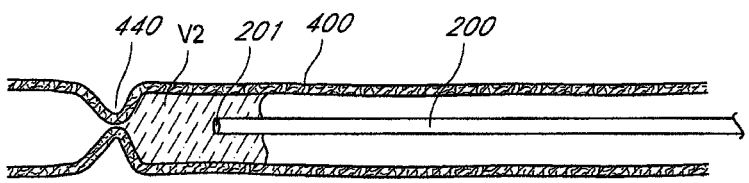
Figure 21D:
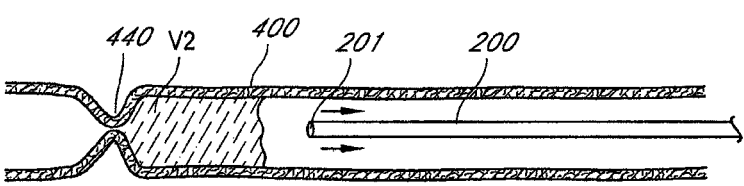
Figure 21E:
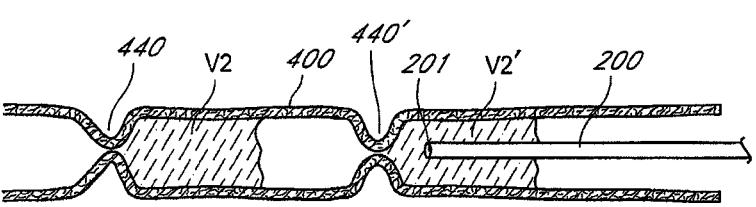

FIG. 21A illustrates a vein 400 that is compressed distally at point 440 to create a first occlusion, such as with external compression. Also shown is catheter 200 with distal end 201. After the creation of an occlusion 440 in a vein, a first volume V1 within the vein 400 can be defined between the distal end 201 of the catheter 200 and the occlusion 440, as illustrated in FIG. 21B. Media having a second volume V2, such as in a bolus, can then be injected from the distal end 201 of the catheter 200 into the vein 400. In some embodiments, the second volume V2 (of the media injected) is at least about 100%, 105%, 110%, 120%, 125%, 130%, 140%, 150%, 175%, 200%, 250%, or more of the first volume V1 (of the vein in between the occlusion and the distal end of the catheter), such that a proximally advancing meniscus of media V2 passes proximally past the distal end 201 of the catheter 200, as illustrated in FIG. 21C. The catheter 200 is then withdrawn proximally, as illustrated in FIG. 21D, and a second more proximal occlusion 440' can be created, such as via external compression. Media can then be injected to create a volume of media V2' greater than the volume within the vein 400 between the distal end 201 of the catheter 200 and the occlusion 440', as illustrated in FIG. 21E. The process can then be repeated for a total of at least 2, 3, 4, 5, 6, 7, 8, 9, 10, or more times depending on the desired clinical result.

In some embodiments, an occlusion in a vein can be created as described herein. A deployment catheter having a distal opening and side wall is provided. The distal end of the deployment catheter can be positioned within the vein at the desired location. Media can then be introduced through the distal opening in a volume sufficient to advance proximally around the catheter between the sidewall of the catheter and the wall of the vein. In some embodiments, the volume sufficient to advance proximally around the catheter between the sidewall of the catheter and the wall of the vein is at least about 0.05 mL, 0.1 mL, 0.2 mL, 0.3 mL, 0.5 mL, 0.7 mL, 0.8 mL, 1 mL, 1.5 mL, 2 mL, 3 mL, or more.

The distal plug 500 may be formed by a bolus of the same material as used for the vein occluding substance 502. Alternatively, the distal plug 500 may be formed from a material that polymerizes more rapidly than vein occluding substance 502, or solidifies through a mechanism other than polymerization to form an occlusive plug. Plug 500 may alternatively be formed by a self-expanding preformed material, such as a foam or woven or non-woven fiber based material, which may be displaced distally from the catheter such as by distally advancing a push wire, or utilizing the pressure of vein occluding substance 502. The self-expanding foam or other plug material 500 may be a bioabsorbable material, so that no long term implant is left behind in the body.

Proximal retraction of the deployment catheter 200 may be accomplished in either a steady, continuous fashion, or in an intermittent, stepped manner. Similarly, extrusion of vein occluding substance 502 may be accomplished in a continuous manner as the catheter 200 is proximally retracted. Alternatively, vein occluding substance 502 may be dispensed in a plurality of bolus ejections along the length of the treatment zone, spaced apart by a predetermined or clinically determined distance. Spacing between adjacent injected volumes of vein occluding substance 502 may be at least about 0.5 cm, at least about 1 cm, at least about 2 cm, and, in some implementations, at least about 4 cm. This procedure minimizes the total volume of injected vein occluding substance 502, while providing a plurality of distinct bonding points along the length of the treatment zone.

Also disclosed herein is a method of obliterating a hollow structure, such as a vein, including the steps of reducing an interior cross-sectional area of the hollow structure near the obliterating site by applying a pressure to an exterior of the hollow structure; and placing a catheter in the hollow structure and advancing it to the obliterating site, where the obliterating site is next to the reduced cross-sectional area. A medical adhesive can then be injected at the obliterating site. The interior cross-sectional area of the medical adhesive at the obliterating site can then be reduced by compressing an exterior of the hollow structure to form an occlusion in the hollow structure. Compression can be achieved, for example, via an imaging probe such as an ultrasound transducer, manual pressure, or a harness. The medical adhesive can then solidify, forming an occlusion in the hollow structure. The method can also include the step of identifying an obliterating site prior to reducing an interior cross-sectional area of the hollow structure. In some embodiments, the catheter is removed from the obliterating site before compression.

With any of the methods and devices described herein, a wide variety of vein-occluding substances can be used. In some embodiments, the substance can include an adhesive such as cyanoacrylate, e.g., 2-octyl cyanoacrylate, and/or a sclerosing agent such as hypertonic saline, sodium tetradecyl sulfate, chromated glycerol, tetracycline, talc, bleomycin, or polydocanol. In some embodiments, a cyanoacrylate can be an aliphatic 2-cyanoacrylate ester such as an alkyl, cycloalkyl, alkenyl or alkoxyalkyl 2-cyanoacrylate ester. The alkyl group may have from 1 to 16 carbon atoms in some embodiments, and can be a C1-C8 alkyl ester or a C1-C4 alkyl ester. Some possible esters include the methyl, ethyl, n-propyl, isopropyl, n-butyl, isobutyl, pentyl, hexyl, cyclohexyl, heptyl, octyl, 2-methoxyethyl and 2-ethoxyethyl esters of cyanoacrylic acid. Other adhesives that can be used include a biological glue such as a bovine serum albumin-gluteraldehyde combination (e.g., BIOGLUE, Cryolife, Atlanta, Ga.), PVA, Biogard, collagen, fibrinogen, fibronectin, vitronectin, laminin, thrombin, gelatin, mixtures thereof, or other biocompatible adhesives. In some embodiments, a foam generated from, for example, one or more of the above components can be used to enhance ablation and closure of the vein. The viscosity and air bubble mixture can also be controlled while taking into account the desired clinical result.

In one embodiment, the chosen adhesive will not produce a significant thermal effect or significant local tissue abnormal effect, but rather produces an initial vessel co-aption/adhesion which will withstand physiological venous pressures within the immediate post-procedure period. Since the adhesive will not produce a significant thermal reaction, no tumescent anesthesia is needed. In some embodiments, the chosen adhesive induces an inflammatory reaction which scars. The inflammatory reaction can be followed by permanent closure of the abnormal greater or less saphenous vein. In some embodiments, the chosen adhesive is hardened after the first few moments (e.g., seconds or minutes) of application and therefore, compression stockings may not be required. With the chosen adhesive, there can be minimal or no danger to surrounding nerves or tissue. While the amount of chosen adhesive delivered to a target site in a vessel will vary depending on the size of the vessel itself, in some embodiments, the amount of adhesive or other vein-occluding substance delivered in a single injection can be between about 0.05 mL and about 0.9 mL, between about 0.05 mL and about 0.5 mL, or between about 0.1 mL and about 0.2 mL in other embodiments. In some embodiments, the amount delivered in a single injection could be more than about 0.4 mL, 0.6 mL, 0.8 mL, 0.9 mL, 1 mL, or more. In some embodiments, the amount delivered in a single injection could be less than about 0.8 mL, 0.6 mL, 0.4 mL, 0.3 mL, 0.2 mL, 0.1 mL, 0.05 mL, or less.

In some embodiments, the cyanoacrylate preparation will contain any additives necessary to impart the desired properties to the preparation as viscosity, color, X-ray opacity, etc. Certain examples of additives such as thickening agents and polymerization inhibitors are discussed further below.

In some embodiments, the chosen adhesive can also be mixed with a thickening agent, including various cyanoacrylate polymers, cyanoacrylate oligmers and biocompatible polymers. The biocompatible polymers can include, for example, PLA, PLLA, PGA, PCL, PDLLA, PLDGA, PMMA, PET, nylon, PE, PP, or PEEK, and in some embodiments, the biocompatible polymers are soluble in a cyanoacrylate monomer. In some embodiments, the thickening agent can comprise glucose, sugar, starch or hydrogel. In some embodiments, the thickening agent can also comprise various particulates, ranging in size between about 0.001 microns to 100 microns. The particulates can be provided in dry solid form and can disperse throughout a liquid adhesive to thicken the adhesive prior to use. In some embodiments, the particulate comprises any of the biocompatible polymers above, such as PLA, PLLA, PGA, PCL, PDLLA, PLDGA, PMMA, PET, nylon, PE, PP, CAB and PEEK, while in other embodiments, the particulate comprises a silica material with or without an acrylic polymer. The thickening agent can assist in providing a suitable viscosity for the adhesive as it flows through the catheter to a target site.

In some embodiments, the chosen adhesive can also be mixed with one or more polymerization inhibitors, which could be, for example, an anionic or a free-radical polymerization inhibitor. Anionic polymerization inhibitors can include soluble acidic gases such as sulfur dioxide, or a biocompatible acid including, but not limited to, acetic acid, sulfuric acid, sulfonic acid, hydrochloric acid, phosphoric acid, carboxylic acid, nitric acid, or combinations thereof. In some embodiments, the acid can be from 0.01% to about 10% by weight, such as between about 0.01% and 1% by weight. Free-radical polymerization inhibitors include hydroquinone, t-butyl catechol, hydroxyanisole, butylated hydroxyanisole and butylated hydroxytoluene. The addition of one or more polymerization inhibitors such as a biocompatible acid helps to change the curing rate of the adhesive to prevent the adhesive from sticking prematurely to the catheter and prevent premature curing of the adhesive prior to binding to the vein wall. In some embodiments, the acid helps to delay the curing and/or polymerization of the adhesive to prevent the glue from sticking to sections of the catheter.

One skilled in the art will appreciate that multiple compositions of adhesive mixtures can be used in accordance with the embodiments described herein. In one embodiment, a composition of adhesive comprises from about 0.01 to about 50.0 weight percent of cyanoacrylate polymer, from about 0.01 to about 50.0 weight percent of a thickening agent selected from the group consisting of cyanoacrylate polymer, cyanoacrylate oligmer and biocompatible polymers, and from about 0.01 to about 10.0 weight percent of a biocompatible acid.

In some embodiments, the adhesive can also include a therapeutic agent such as an anti-inflammatory agent, an anti-infective agent, an anesthetic, a pro-inflammatory agent, a cell proliferative agent, or combinations thereof.

In some embodiments, the medical adhesives, such as the cyanoacrylate adhesives, can have select properties. In some embodiments, the medical adhesives can have a setting time of between about 5 to 60 seconds. The medical adhesives can also have a viscosity of between about 40 to 3000 cp. In some embodiments, the viscosity could be at least about 500 cp, at least about 1,000 cp, at least about 1,500 cp, at least about 2,000 cp, at least about 2,500 cp, or more. In some embodiments, the viscosity could be no more than about 2,000 cp, no more than about 1,500 cp, no more than about 1,000 cp, no more than about 500 cp, no more than about 300 cp, or less. One skilled in the art will appreciate that the type of adhesive is not limited to these particular characteristics, and that other adhesives having different properties may also be applicable.

Additional Embodiments Related to the Vein Closure System

In additional embodiments, a vein closure system is described that does not require capital purchases for a radiofrequency device or laser box. Simple and non-invasive methods of using the vein closure system are provided, and in some embodiments, the methods do not require application of a tumescent anesthesia or wearing compression stockings. The acceptance by and demand from patients of the vein closure system described herein will be much higher over existing devices and techniques.

In some embodiments, the closure system comprises at least two major components. One is a vein closure device which precisely delivers an adhesive to the abnormal saphenous vein under ultrasound guidance. The other component is a unique intravascular adhesive which allows for co-aptation and closure of the abnormal saphenous vein in a flattened, closed position. In other embodiments, the closure system comprises three major components. The first is a vein closure device which precisely delivers an adhesive to the abnormal saphenous vein under ultrasound guidance. The second is a unique intravascular adhesive which allows for co-aptation and closure of the saphenous vein just distal to the Superficial Femoral Vein Junction, such as within about 5 cm, 4 cm, 3 cm, 2 cm, 1 cm, or less in a flattened, closed position. The third is a solution that can have adhesive and/or sclerosing properties which allows for co-aptation and closure of the rest of the saphenous vein to alter the vein such that blood flow is prevented therein.

The Vein Closure Device

In some embodiments, the vein closure device which delivers the vein-occluding substance, e.g., an embolic adhesive, comprises three components. The first component is an outer catheter or introducer sheath that allows for placement under precise ultrasound guidance into the saphenous vein from as low a position as possible in the greater saphenous vein or lesser saphenous vein. The vein closure device is also configured for precise distal tip placement into the vein to be occluded. In some embodiments, the sheath is available in multiple size ranges and includes ID of 3fr-7fr and a length from 25 cm to 100 cm depending on the placement site. In some embodiments, the sheath is echogenic under ultrasound observation and therefore can be precisely placed below the sapheno-femoral junction. The sheath can have multiple graduations, as well as measurement markings that indicate increments along the sheath, such as 0.2, 1, 2, or 5 cm increments. The graduations and markings assist in providing precise, monitored pull-back motions along the saphenous vein. In some embodiments, a dilator is positioned within the introducer sheath to aid in positioning the device at the treatment site. The dilator may have comparatively greater stiffness than the introducer sheath. Upon advancement to the desired treatment site, the dilator may be removed, followed by advancement of the introduction or inner catheter through the introducer sheath. In some embodiments, the dilator is echogenic under ultrasound observation which may aid in precise placement below the sapheno-femoral junction.

The second portion of the vein closure system is an introduction or inner catheter for the vein-occluding substance or adhesive. The inner catheter can be multiple sizes, such as from 3fr-7fr and include lengths of between about 25 cm to 100 cm to match the introduction sheath size ranges. In some embodiments, the inner catheter can be longer than the introduction sheath to allow the inner catheter to extend from a distal end of the introduction sheath. In one embodiment, both the inner catheter and the introducer sheath are made of materials such as PTFE, ePTFE, PFA, FEP, or similar polymeric materials that will provide for negligible (if any) adhesion to the vein-occluding substance. In some embodiments, the inner catheter has an echogenic tip that assists in advancement through the introducer sheath. The inner catheter can be attached to the introducer sheath, such as by luer lock or other locking mechanism. The inner catheter protrudes from the introduction sheath at its distal end approximately 0.5-10 cm. and is visible under ultrasound due to its echogenic tip. The inner catheter is used for precise delivery of a vein-occluding substance into the vein for co-apting and occluding the vein into a flattened configuration. In some embodiments, the outer catheter and/or inner catheter can be coupled to or extend from a syringe designed to dispense a vein-occluding substance.

Also disclosed herein is a medical device that can include one, two, or more echogenic characteristics for enhanced visualization. For example, one or more of the outer catheter, the dilator, and the inner catheter may be echogenic in certain embodiments, providing for improved visualization under ultrasound. Since sound waves are reflected at junctions of differentiated density, the greater the density difference, the brighter the junction appears on an ultrasound visualization monitor. Since ultrasound waves do not pass easily through gases and are mostly reflected, the presence of gas in the path of ultrasound waves provides for improved visualization. In certain embodiments, to provide a high degree of visualization, the introducer sheath, dilator, and/or the catheter may include a high degree of density differentiation by using gas, such as air. This reflection of ultrasound waves provides a means to visualize the location and allow ease of placement of devices within soft tissue.

Most ultrasound visualization of medical devices involves using metals (such as platinum marker bands or metal wire woven extrusions) or the addition of powders (such as barium sulfate) to extrusions to create density differences between the device and the surrounding tissues. Using a gas, rather than a metal or powder, to create the density differences provides several distinct advantages in certain situations. First, gas can be orders of magnitude less expensive than other ultrasound visualization materials of the same given volume. Even relatively inexpensive metals, such as stainless steel, cannot compete with the low cost of a gas, such as air. Second, gas does not need to be processed into a particular shape; it takes the form of whatever void it is filling. Hence it is more pliable and retains much less embodied energy. This improves the ease of manufacture as well as the final flexibility of the catheter. Third, the density disparity between the gas and the object holding and/or the surrounding tissue is typically greater than that of other visualization methods, thereby allowing the device to reflect more ultrasound waves and providing a clearer or brighter image. Improved ultrasound imaging may facilitate more accurate placement of the device to the desired treatment spot, such as within the greater saphenous vein or other vessels as described herein. Ultrasound can also be advantageous in not carrying the radiation concerns inherent in, for example, fluoroscopy. This gas/solid boundary can be created in any number of ways. Some non-limiting examples follow.

In one embodiment, microlumens containing trapped gas may be formed within the sidewall of the catheter. With reference to FIGS. 22A-22D, catheter 600 includes a catheter wall 602, defining a main or central inner lumen 604, and open proximal and distal ends, or a proximal end with at least one side port for accessing the central inner lumen 604. In certain embodiments, a dilator or a second inner catheter (not shown) may pass through the inner lumen 604 of first (outer) catheter 600. In other embodiments, adhesive may flow through the inner lumen 604 of catheter 600. Within the catheter wall 602 are one or more microlumens 606 which run partially or completely along the length of catheter 600. These microlumens 606 may contain air or any other trapped gas to improve ultrasound visibility. The microlumens 606 may be sealed at the distal tip during the tipping process, and the proximal end may be sealed, such as with adhesive when affixing a luer lock or other connector thereto. In other words, the microlumens could have closed proximal as well as distal ends. Alternatively, only the distal ends may be sealed. The proximal ends may then be left open to atmospheric conditions. In other embodiments, gas may be delivered to the proximal end, whereby the gas is allowed to flow distally from the proximal end, down through the microlumens, and back out the proximal end again. Any other mechanism which permits air to be trapped within the microlumens may be employed. For instance, instead of physical sealing, the microlumens may be tapered at the distal and proximal ends such that the opening is small enough to prevent the entry of fluids due to surface tension. As such, in some embodiments the microlumens could be hermetically sealed, or alternatively having openings of a diameter to allow a gas therethrough, but that is insufficient to permit the entry of a liquid. In alternative embodiments, the catheter may include more than one inner lumen. For example, a configuration in which two separate lumens are arranged within the catheter would permit the delivery of two separate components to the delivery site, where mixing would only occur after each of the components is dispensed from the catheter.

Embedding the microlumens 606 within the catheter wall 602 ensures that they do not interfere with the operation of the catheter or hinder its intravascular mobility. Any raised edge or protruding portion on the outer surface of catheter 600 could potentially increase the likelihood of the catheter being caught or even causing injury to the vasculature during advancement to the treatment site, or during retraction therefrom. Similarly, any protrusion into the inner lumen 604 would potentially inhibit the flow of adhesive or the passage of an inner catheter therethrough. Since embedding the microlumens 606 within the wall 602 maintains both a smooth outer surface and a smooth inner surface, these potential problems may advantageously be avoided.

In certain embodiments, the catheter 600 may include one microlumen 606. Other embodiments may include two, three, four, five, six, or more microlumens embedded within the catheter wall 602. According to some embodiments, the microlumens may run parallel or substantially parallel to the main inner lumen 604 and/or the catheter sidewall 602. In other embodiments, the microlumens may be oriented in another configuration. For instance, the microlumens may spiral helically around the catheter 600, or may form a zig-zag pattern along its length. Other configurations are also possible.

Figure 22A:
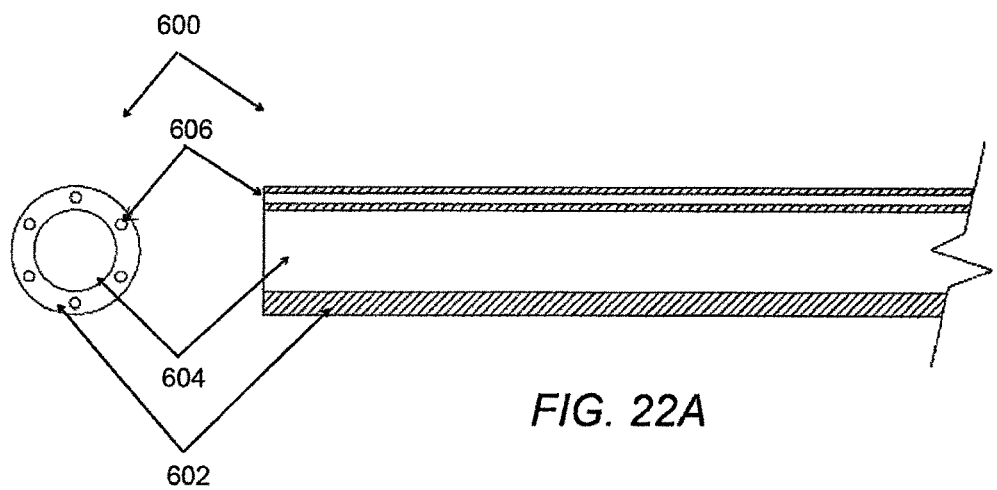
FIGS. 22A-22D illustrate embodiments of an echogenic catheter with embedded microlumens.
Figure 22B:
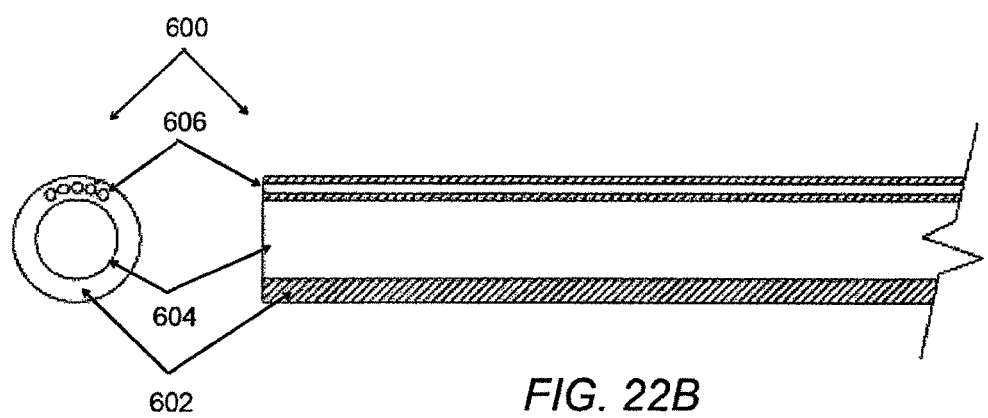

As shown in FIG. 22A, in certain embodiments a plurality of microlumens 606 may be arranged such that they are equally spaced radially within the catheter wall 602. In other embodiments, the microlumens may be arranged in irregularly, or in clusters, as shown in FIG. 22B. The catheter may be formed of any desired material. For instance, the catheter may be formed from a plastic such as polytetrafluorethylene (PTFE), stainless steel, or other material.

Figure 22C:
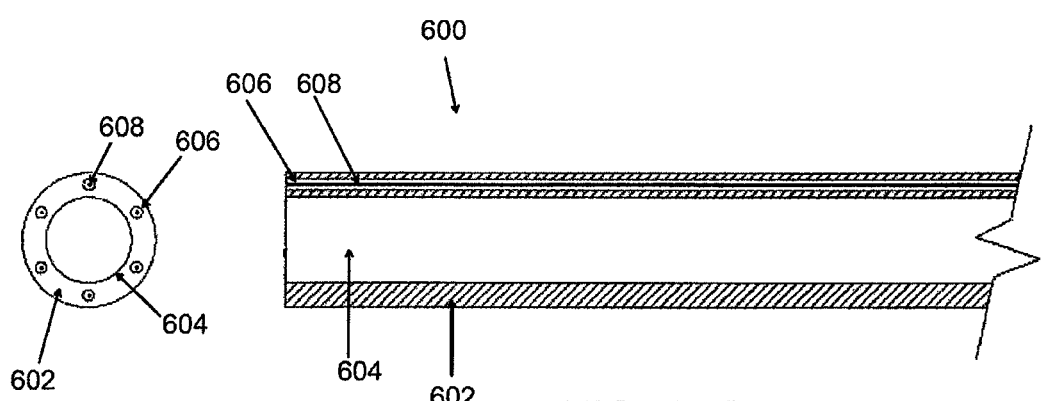

The use of a gas/solid boundary may also be combined with other techniques for improving ultrasound visibility. For instance, as shown in FIG. 22C, a wire 608 that could be made of a metal may be located within each gas-filled microlumen 606. The cross-sectional diameter of the microlumens may vary. For example, in various embodiments, the diameter of the microlumens may be about or less than 50 µm, 100 µm, 150 µm, 200 µm, 250 µm, or more. In some embodiments, the diameter of the microlumens may be about or more than about 250 µm, 200 µm, 150 µm, 100 µm, 50 µm, or less. In certain embodiments, each microlumen 606 includes a thin metal wire 608 located within it, the wire 608 having an outer diameter that about or no more than about 90%, 80%, 70%, 60%, 50%, or less of the diameter of the microlumen. In other embodiments, some but not all of the microlumens 606 include metal wires 608 located within. The metal wires 608 may be placed within previously existing microlumens 606, or alternatively the catheter tubing may be extruded directly over the metal wires 608 to enclose them within the microlumens. The metal wire 608 may extend along the entire length of the microlumen 606. Alternatively, the metal wire 608 may only extend along a portion of the microlumen 606.

In some embodiments, the length of the metal wire 608 varies from one microlumen to the next. For instance, a first microlumen may contain a metal wire 608 of a first length. A second microlumen may contain a metal wire 608 of a second length longer than the first length. A third microlumen may contain another metal wire 608 that is longer than the second, and so forth. In certain embodiments, the lengths of the metal wires may be offset from one another by a uniform amount. For instance, a one metal wire may extend the full length of the catheter, while the next metal wire terminates 1 cm short of the distal tip. Another metal wire may terminate 2 cm short of the distal tip, and so forth. The arrangement of several metal wires of subsequently shorter lengths may advantageously provide a means for determining more precisely the location of the catheter within the body. This configuration may aid in determining the position of the catheter within the body.

Figure 22D:
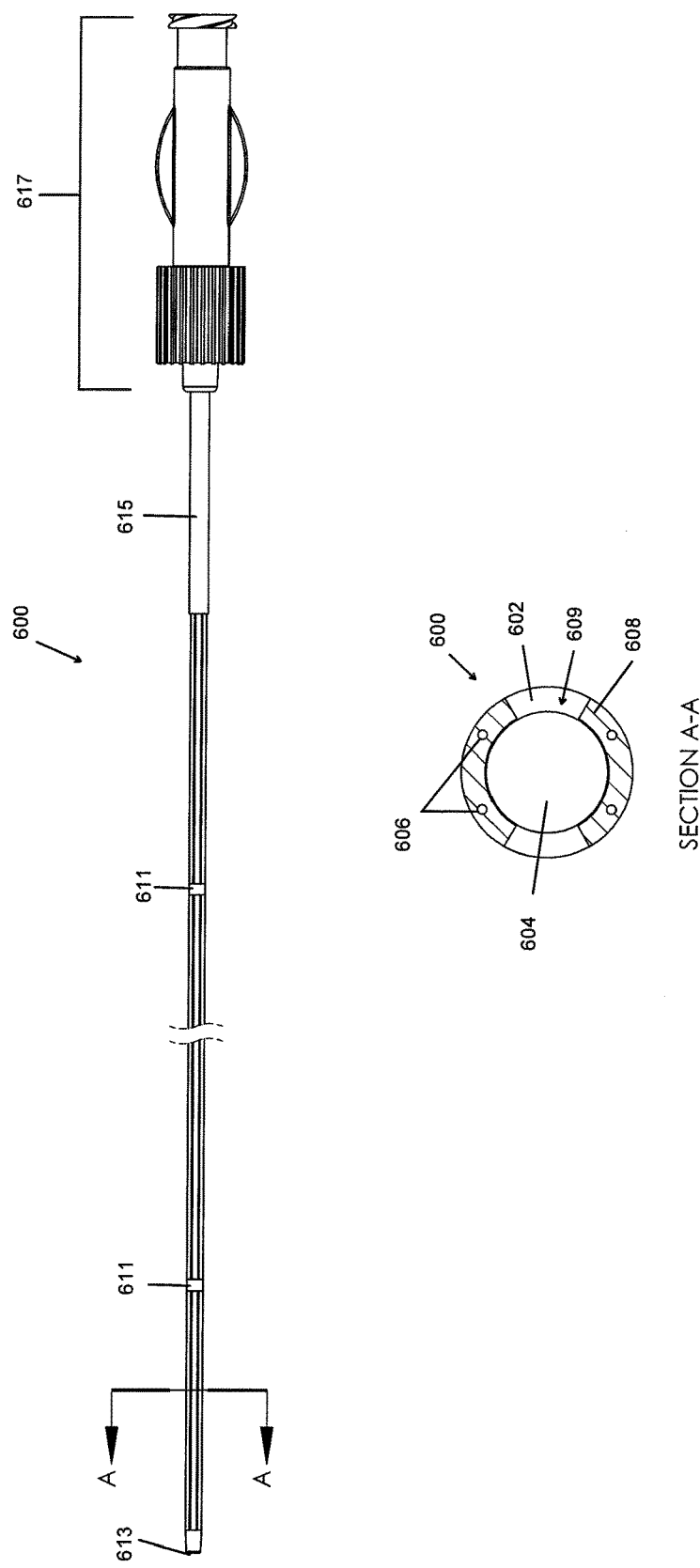

With reference to FIG. 22D, at least a portion of the catheter sidewall 602 may include first see-through (e.g., transparent or translucent) sections 607 and second opaque sections 609 (in the lower cross-section A-A of the view of catheter 600 in the upper part of FIG. 22D). Providing see-through sections 608 may allow the physician to view fluid within the lumen 604. A series of indicia, e.g., laser markings 611 may be disposed at one, two, or more locations along the axial length of the catheter. The opaque section 609 can provide improved visibility of the markings 611. In various embodiments, the opaque sections 608 can comprise, for example titanium dioxide or a material having a desired color. The laser markings 611 can be spaced apart at regular or irregular intervals permitting the user to judge distances. In some embodiments, the laser markings 611 can be spaced at regular intervals, for example every 3 cm, every 5 cm, or more which can be advantageous in determining locations to release a bolus of a substance within a body lumen. In various embodiments, the laser markings 611 can be spaced irregularly. For example, in the illustrated embodiment, the distal-most laser marking 611 is positioned 3 cm from the distal tip 613, and the second laser marking 611 is positioned 85 cm from the distal tip 613, which can be advantageous positioning, for example, at an appropriate starting location for a procedure to coapt a vein such as the saphenous vein.

With continuing reference to FIG. 22D, the catheter 600 may be outfitted with an atraumatic distal tip 613, which includes an opening of the lumen 604. As described above, in various embodiments some or all of the microlumens 606 may also be open at the distal tip 613. In other embodiments, some or all of the microlumens 606 may be sealed at the distal tip 613. The catheter 600 also includes a strain relief 615, which is adjacent to the proximal hub 617. The hub 617 comprises one or more input ports which can include spin locks. In some embodiments, the spin lock can be a Luer lock consistent with ISO prescribed dimensions, for example as described in ISO 594-1 (First Edition 1986-06-15) and ISO 594-2 (Second Edition 1998-09-01), both of which are hereby incorporated by reference in their entireties. Various other configurations for the hub 617 are possible. For example, the input port could be on the proximal end of the hub 617 as shown coaxial with the longitudinal axis of the catheter. In some embodiments, one or more input ports could be longitudinally offset from the longitudinal axis of the catheter, such as at an angle to the sidewall of the hub.

Figure 23:
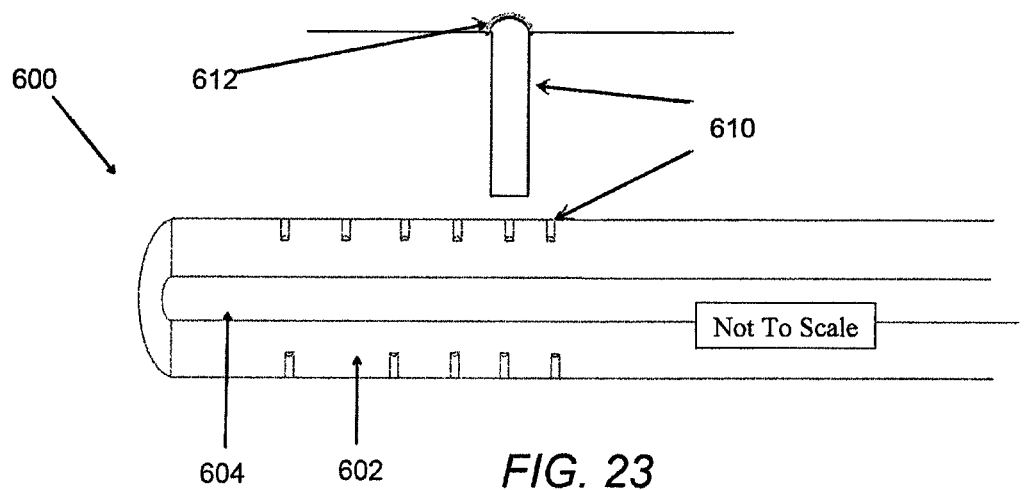
FIG. 23 illustrates an echogenic catheter with microwells.

In another embodiment, a gas/solid boundary may be provided via small holes in a direction either normal or oblique to the longitudinal axis of the catheter. The apertures form microwells that are large enough to hold gas within, but small enough to prevent fluids from entering the hole due to surface tension. As such, a meniscus 612 naturally forms at the boundary of gas and liquid at the surface of the microwell 610. The gas trapped within each microwell provides for increased ultrasound visibility. In exemplary embodiments, the microwells are configured such that gas is retained therein when the catheter is submerged within whole blood. For example, the microwells may be dimensioned so that surface tensions between about $30\times10^{-3}$ N/m and $80\times10^{-3}$ N/m, or about $50\times10^{-3}$ N/m and $64\times10^{3}$ N/m prevent liquids from entering the microwells. With reference to FIG. 23, microwells 610 are drilled into the surface of catheter 600. The microwells may be formed by mechanical drilling, laser drilling, chemical etching, or any other means. The microwells may extend partially through the catheter wall 602. In other embodiments, the microwells may extend completely through the catheter wall 602. The microwells 610 may have a cross-section that is circular, elliptical, rectangular, irregular, or any other shape, so long as the surface tension prohibits any, or substantially any liquid, whether bodily fluids or adhesives, from entering the microwell 610. In some embodiments, the cross-sectional area of the microwells may range from 1 $\mu m^2$ to 1 $mm^2$, from 50 $\mu m^2$ to 750 $\mu m^2$, or from 100 $\mu m^2$ to 500 $\mu m^2$. In certain embodiments, the cross-sectional area of the microwells may be 1 $\mu m^2$, 5 $\mu m^2$, 10 $\mu m^2$, 25 $\mu m^2$, 50 $\mu m^2$, 100 $\mu m^2$, 500 $\mu m^2$ or more. In other embodiments, the cross-sectional area of the microwells may be 500 $\mu m^2$, 100 $\mu m^2$, 50 $\mu m^2$, 25 $\mu m^2$, 10 $\mu m^2$, 1 $\mu m^2$, or less.

The microwells 610 may be arranged radially in a regular pattern. For instance, the microwells 610 may be spaced equally radially around the catheter 600. Alternatively, the microwells 610 may be arranged in clusters or irregularly radially around the catheter 600. In addition to the radial orientation, the longitudinal spacing of the microwells may be varied. For instance, the microwells may be oriented in groups arranged circumferentially and spaced apart longitudinally by equal distances. In this configuration, each ring of microwells surrounds the catheter at a given location, and is spaced apart from the longitudinally adjacent ring of microwells by a particular distance. In certain embodiments, the longitudinal distance between adjacent rings of microwells may vary to provide location identification.

In some embodiments, the microwells may have identical sizes. In other embodiments, the cross-sectional dimensions may vary, as may the depth.

Figure 24:
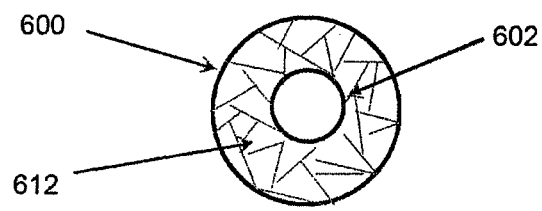
FIG. 24 illustrates an echogenic catheter with enclosed gas pockets.

In still another embodiment, a gas/solid boundary may be formed via enclosed gas pockets, whether random or otherwise, within the wall of the catheter 600. For instance, as shown in FIG. 24, the catheter may be manufactured with closed cell expanded PTFE (ePTFE), which will contain pockets of air 612 within it, the air pockets being isolated and spaced apart from the central lumen of the catheter. Alternatively, open cell ePTFE may be used in conjunction with an enclosing sheath. Methods of manufacturing ePTFE are well known in the art. Due to its natural resistance to adhesion, ePTFE may facilitate the unimpeded flow of adhesive material through the lumen to the treatment site. The use of enclosed air pockets is not limited to ePTFE, however, but rather any suitable expanded plastic or other material that contains enclosed pockets of air may be used, such as an open or closed cell material, including a sponge material. Additionally, in some embodiments differing materials are used as an outer sheath. One way of accomplishing this would be through the manufacture of closed cell ePTFE or open cell ePTFE with an enclosing sheath.

The enclosed gas pockets may be formed within any suitable material within the catheter. For instance, in some embodiments, a polymer containing gas-filled microspheres may be used to manufacture the catheter. In other embodiments, gas or foaming agents may be injected into a polymer, such as polyurethane, to form a polymeric layer with enclosed gas pockets. Chemical foaming agents that could be added to the plastics material include azocarbonomides, dinitrosopentmethelyene-tetramine, benzenephonohydrazine, 4,4 oxybis(benzenephonohydrazine), NN$^1$dimethyl-NN.sup.1dinitrosoterephthalamide, azoisobutyronitrile, sodium bicarbonate, terephthalazide or trihydrazinatrazine. Another way of forming the gas pockets would be by incorporating a liquid into the plastics melt which volatizes during the melt process. Alternatively, solid powdered dry ice (carbon dioxide) could be incorporated into the melt so that the particles of dry ice become gas pockets during the forming process. It could be possible to use other solids which undergo sublimation in this way. The gas pockets could be formed directly as a result of chemical reaction during polymerisation and or alternatively during cross-linking. The gas pockets could be formed mechanically by whipping the plastics in a liquid form, such as in the manner used to form latex foam. Alternatively, small particles of a soluble material could be added to the plastics melt and subsequently dissolved away.

A protective sheath may surround a polymer with enclosed gas pockets to define the catheter, or in other embodiments no such sheath is required.

The gas pockets in some embodiments extend in a continuous or discontinuous region along the length of the device. The gas pockets may have a dimension, such as a width of between 0.1 $\mu$m to 300 $\mu$m, between 1 $\mu$m and 50 $\mu$m, or between 5 $\mu$m and 10 $\mu$m. In some embodiments, the width of the gas pockets are 0.1 $\mu$m, 5 $\mu$m, 10 $\mu$m, 50 $\mu$m, 300 $\mu$m, or more. In other embodiments, the width of the gas pockets are 300 $\mu$m, 50 $\mu$m, 10 $\mu$m, 5 $\mu$m, 0.1 $\mu$m, or less. In certain embodiments, the enclosed gas pockets are distributed uniformly along the length of the device. In other embodiments, the enclosed gas pockets may be patterned, irregularly distributed, or otherwise within the device.

In each of these aforementioned non-limiting examples, the inclusion of gas regions within the catheter provides for multiple gas/solid boundary regions. As discussed above, each of these boundaries allows for improved ultrasound visibility. With greater visibility and heightened resolution, the location of the catheter within the body may be accurately determined. In particular, the use of such an echogenic catheter may advantageously facilitate precise placement below the sapheno-femoral junction for use in the treatment of venous reflux, such as for injection of an adhesive composition at one, two, or more locations within the vein for example.

Glue Gun and Adapter

The third portion of the vein closure system is the glue gun or other adhesive introducing device that attaches to the inner catheter. In some embodiments, the adhesive introducing device is a manual liquid dispenser gun that can dispense an adhesive into a vessel with control and accuracy. One such dispenser gun is disclosed in U.S. Pat. No. 6,260,737 to Gruendeman et al., which is incorporated by reference herein in its entirety. Other embodiments of the glue gun are discussed in more detail below.

Additional embodiments are provided that are directed to a vein-occluding substance dispenser adapter, such as a glue gun, and associated components. In some embodiments, a glue gun is provided that is mateably attachable to a dispensing catheter or syringe by an adapter. The adapter can advantageously convert, for example, a conventional industrial glue gun for medical use, such as described herein while being properly sterilized as well.

Figure 25:
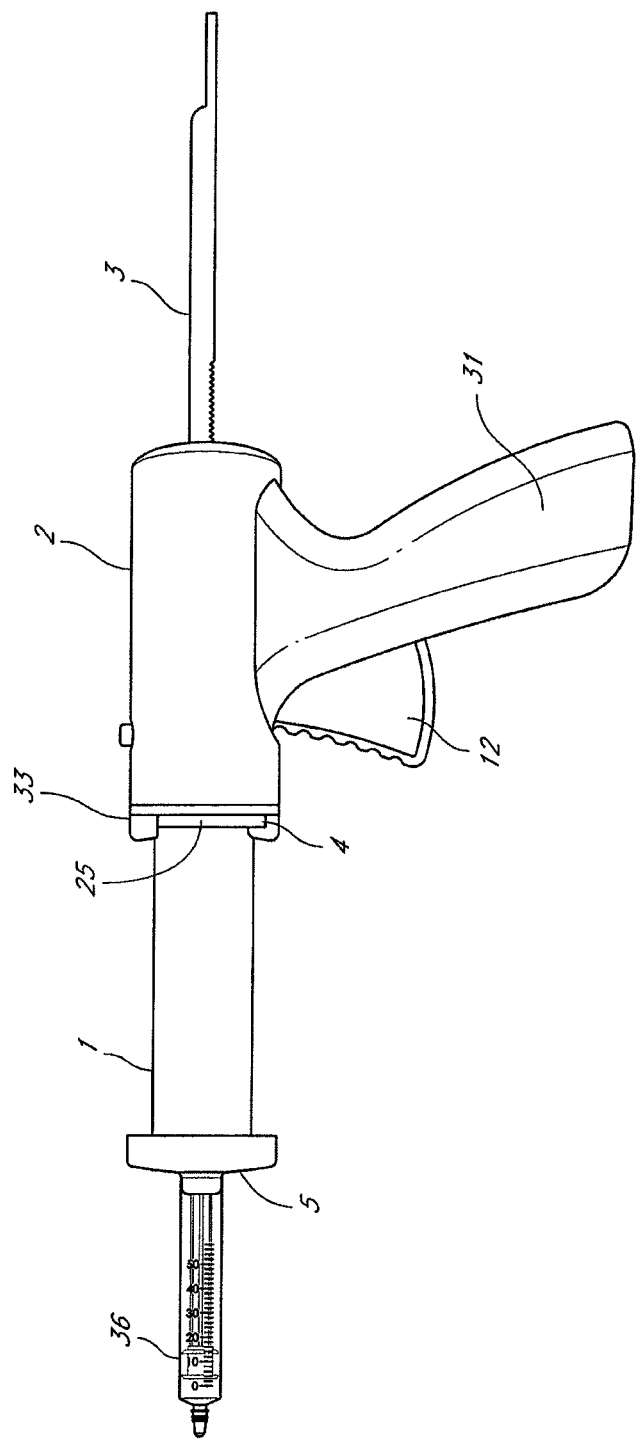
FIGS. 25-35 illustrate various views and components of a vein-occluding dispensing system according to some embodiments of the invention.

FIGS. 25-35 illustrate a glue gun system configured to assist in the dispensation of a vein-occluding substance, according to some embodiments of the invention. FIG. 25 illustrates a side view of a glue gun and adapter system including an adapter 1, a glue gun 2, and a plunger 3 according to one embodiment. The adapter 1 includes an adapter lock end 4 with collars or flanges 25 that allow the adapter 1 to be fixed to the glue gun 2 via a holding segment 33. The adapter 1 further includes a syringe lock end 5 that allows the adapter 1 to be fixed to a syringe 36.

The glue gun 2 includes a handle 31 and a pull trigger 12. The pull trigger 12 is used in connection with internal mechanisms of the glue gun 2 (shown in FIGS. 36 and 37 and described further below) and the plunger 3 to provide controlled dispensation of a vein-occluding substance through syringe 36.

The plunger 3 comprises a solid rail-like segment that extends from outside the body of the glue gun 2 and through the internal body of the glue gun 2. The plunger 3 includes teeth that work in conjunction with a spring pawl mechanism (shown in FIG. 37) to lock the position of the plunger 3 and provide controlled dispensation of glue. The distal end of the plunger 3 makes contact with the proximal end of the syringe 36 such that the plunger 3 is capable of pushing the syringe to dispense a vein-occluding substance such as an adhesive.

Figure 26:
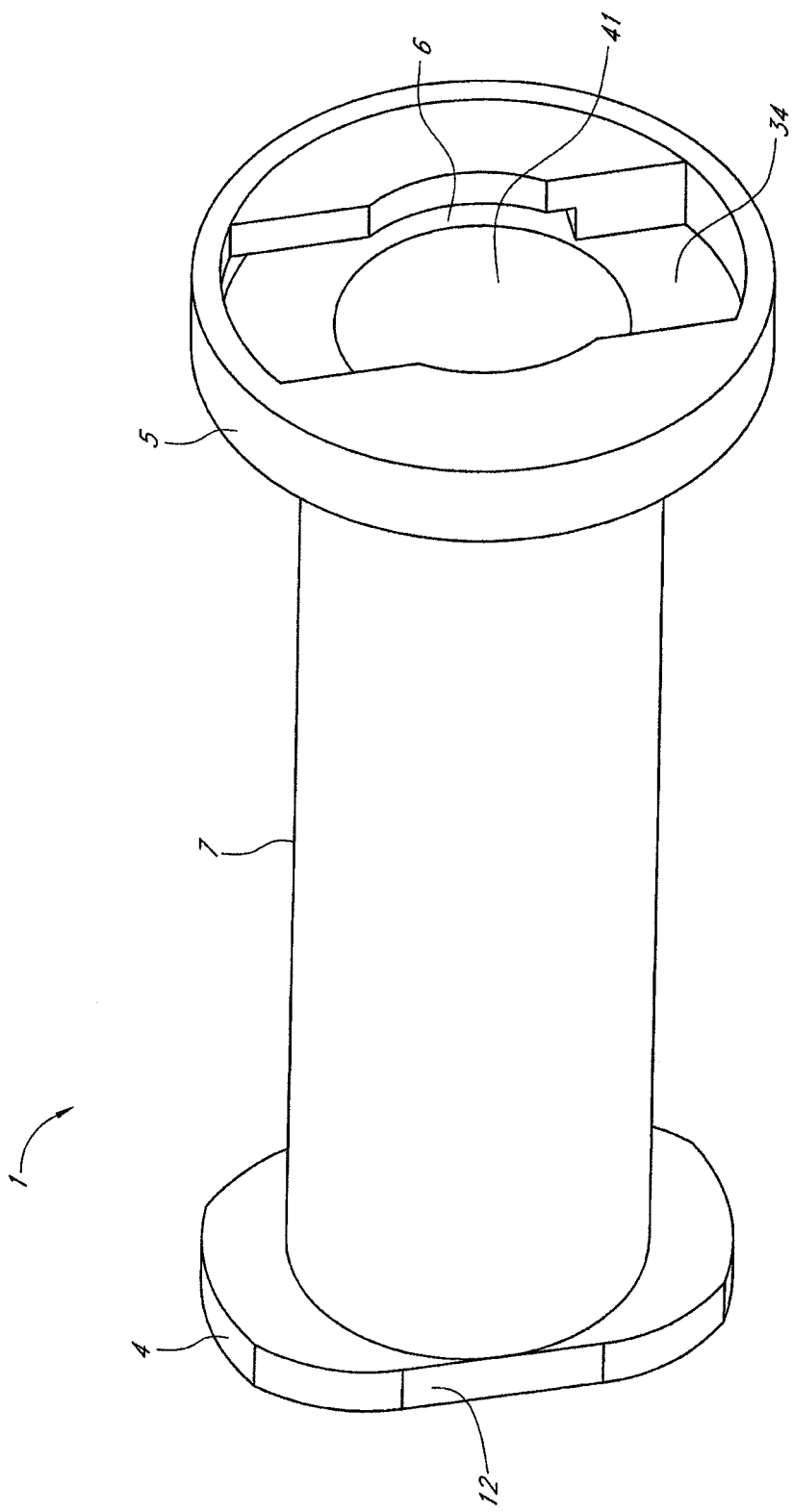

FIG. 26 illustrates a perspective view of the adapter 1 in FIG. 25. The adapter 1 includes an adapter lock end 4, a syringe lock end 5, a holding slot 6 and a hollow body 7.

The adapter lock end 4 includes one or more collars or flanges 25 that are receivable into a holding segment of the dispenser gun upon rotation. The adapter lock end 4 is configured such that upon rotation of the adapter 1, the flanges 25 are received in and secured in the holding segment 33. In addition, the adapter lock end 4 includes an opening or slot (shown in FIG. 28) through which the distal end of the plunger 3 can be inserted.

The syringe lock end 5 includes a holding slot 6 for receiving a syringe 36 and an opening 41 through which the plunger 3 can pass. As shown in FIG. 26, the holding slot 6 is shaped like a barrel-wing. To secure a syringe to the syringe lock end 5, a proximal end of a syringe can be introduced into the holding slot 6. In some embodiments, the proximal end of the syringe can be barrel-wing shaped such that when the syringe is introduced to the syringe lock end 5, the syringe comes into contact with walls 34 of the holding slot 6. The syringe can then be rotated so that it is securely received in the holding slot 6. One skilled in the art will appreciate that the holding slot 6 and the proximal end of the syringe need not be shaped similarly. Nor is it necessary for the holding slot 6 to be barrel-wing shaped; any shape is suitable so long as it can receive a syringe end prior to rotating and securing of the syringe.

The hollow body 7 of the adapter 1 is designed to receive the syringe plunger 3 as it moves transversely substantially along a longitudinal axis of the hollow body 7 during injection. In some embodiments, the length of the hollow body 7 of the adapter is between 2 and 5 inches. The hollow body can be circular, elliptical or any other shape suitable for receiving the plunger 3. The diameter of the hollow body 7 can be, in some embodiments, between 0.5 and 1.1 inches.

Figure 27:
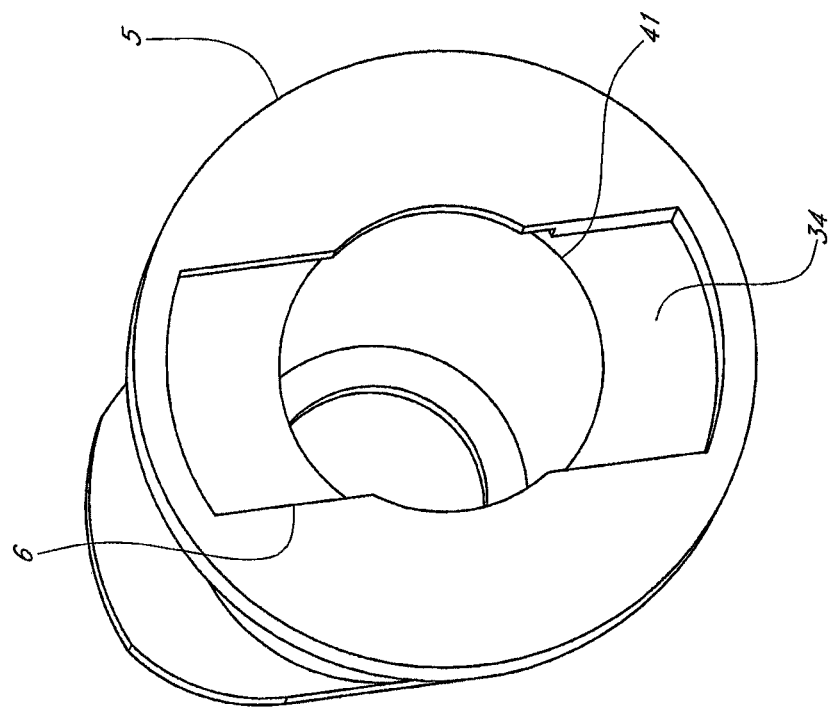

FIG. 27 illustrates a front perspective view of the adapter 1 in FIG. 25, including the opening 41 through which the plunger 3 can be received. Also shown are walls 34 of the syringe lock end 5. The walls 34 are shaped such that upon initial entry of a syringe into the syringe lock end 5, surfaces of the syringe 36 are placed into contact with the walls 34. Upon rotation of the syringe 36, the syringe 36 can be locked into place in the holding slots 6.

Figure 28:
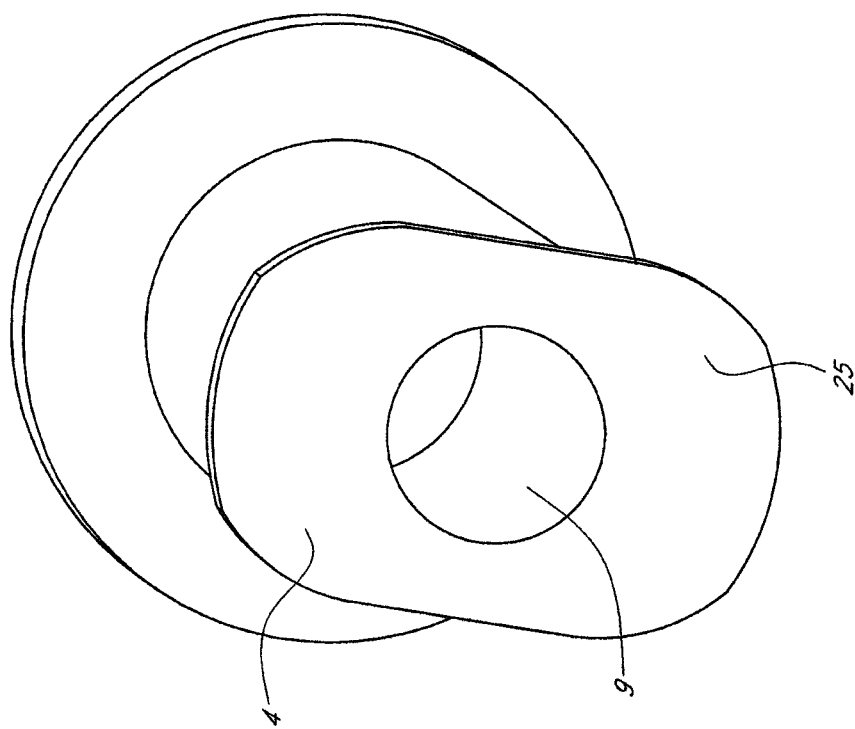

FIG. 28 illustrates a rear perspective view of the adapter 1 in FIG. 25, including the adapter lock end 4 and flanges 25 receivable in the holding segment 33 of dispenser gun 2. Also illustrated is hole or opening 9 through which the plunger 3 can pass during the injection of vein-occluding substance.

Figure 29:
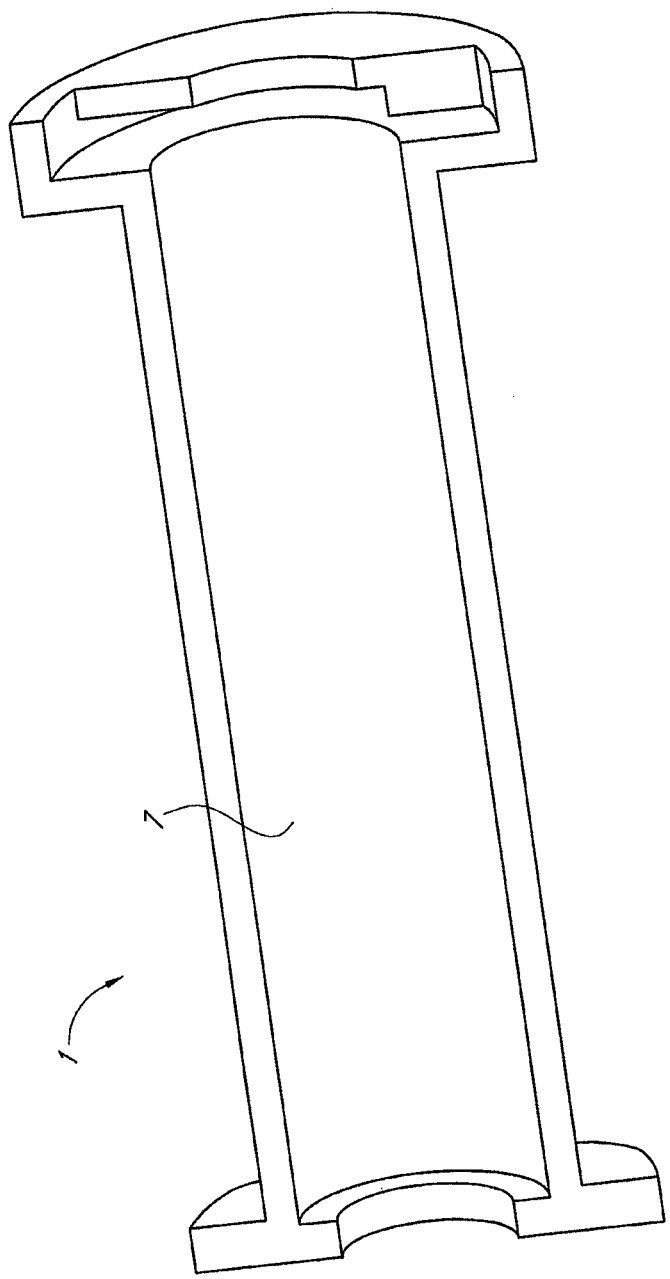

FIG. 29 illustrates a cross-sectional view of the adapter 1 and its hollow body 7. From this view, it is possible to see the adapter 1 as having at least two separate diameters, an inner diameter (formed at the openings to the hollow body 7) and an outer diameter (formed in the hollow body 7 itself). In some embodiments, the inner diameter is between 0.5 and 0.9 inches, while the outer diameter is between 0.7 and 1.1 inches.

Figure 30:
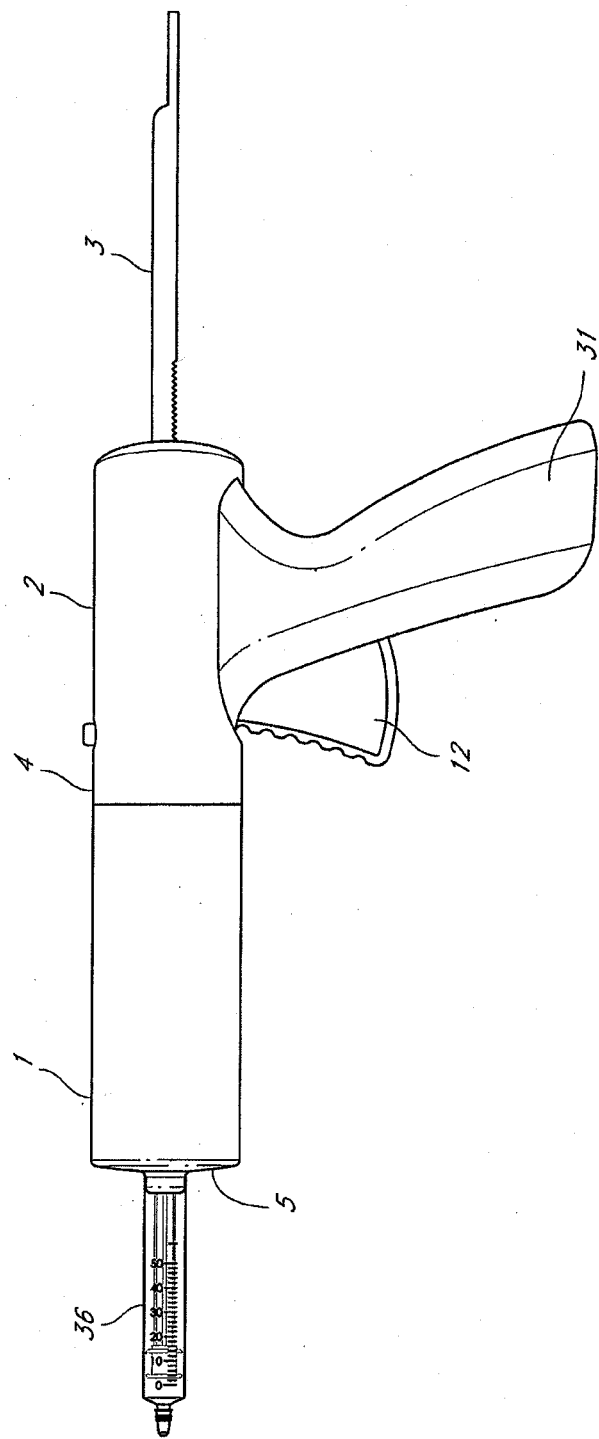

FIG. 30 illustrates a side view of a glue gun system including an adapter 1, a glue gun 2, and a plunger 3 according to another embodiment. The system includes an adapter lock end 4 and a syringe lock end 5 having a syringe 36 attached thereto. In contrast to the system in FIG. 25, the glue gun system in FIG. 30 does not include an adapter lock end 4 having an exposed collar or flange that is placed in a holding segment of the gun 2. Instead, the adapter lock end 4 includes a flange 25 (shown in FIG. 32) that mates with the glue gun 2 and remains unexposed upon final assembly.

Figure 31:
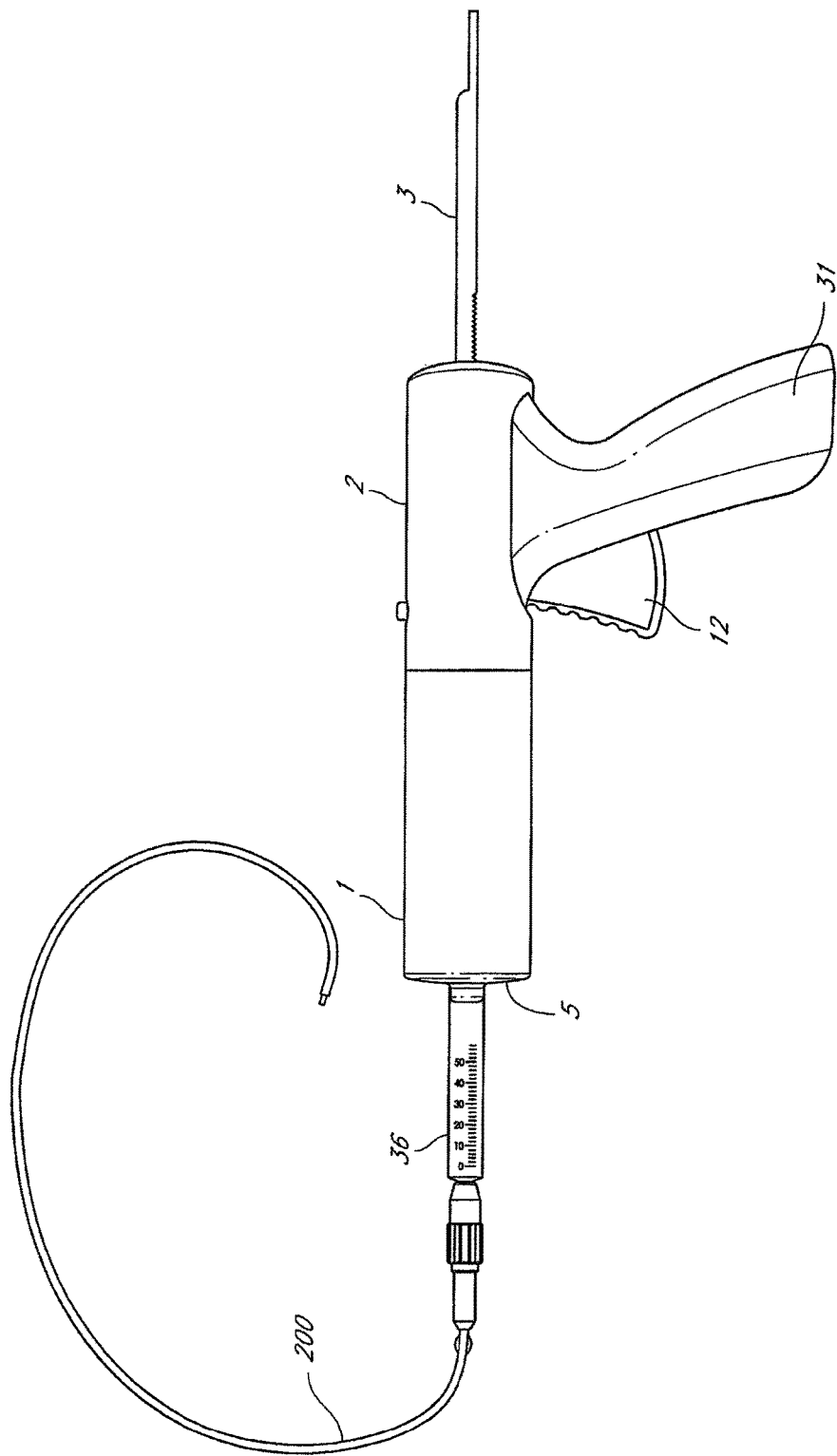

FIG. 31 illustrates a side view of the glue gun and adapter system of FIG. 30 including the adapter 1, the glue gun 2, the plunger 3, and in addition, a delivery catheter 200. In some embodiments, the delivery catheter 200 includes an outer catheter surrounding an inner catheter. The delivery catheter 200 extends from the distal tip of the syringe 36 and is designed to provide access to a target site within a vessel interior.

Figure 32:
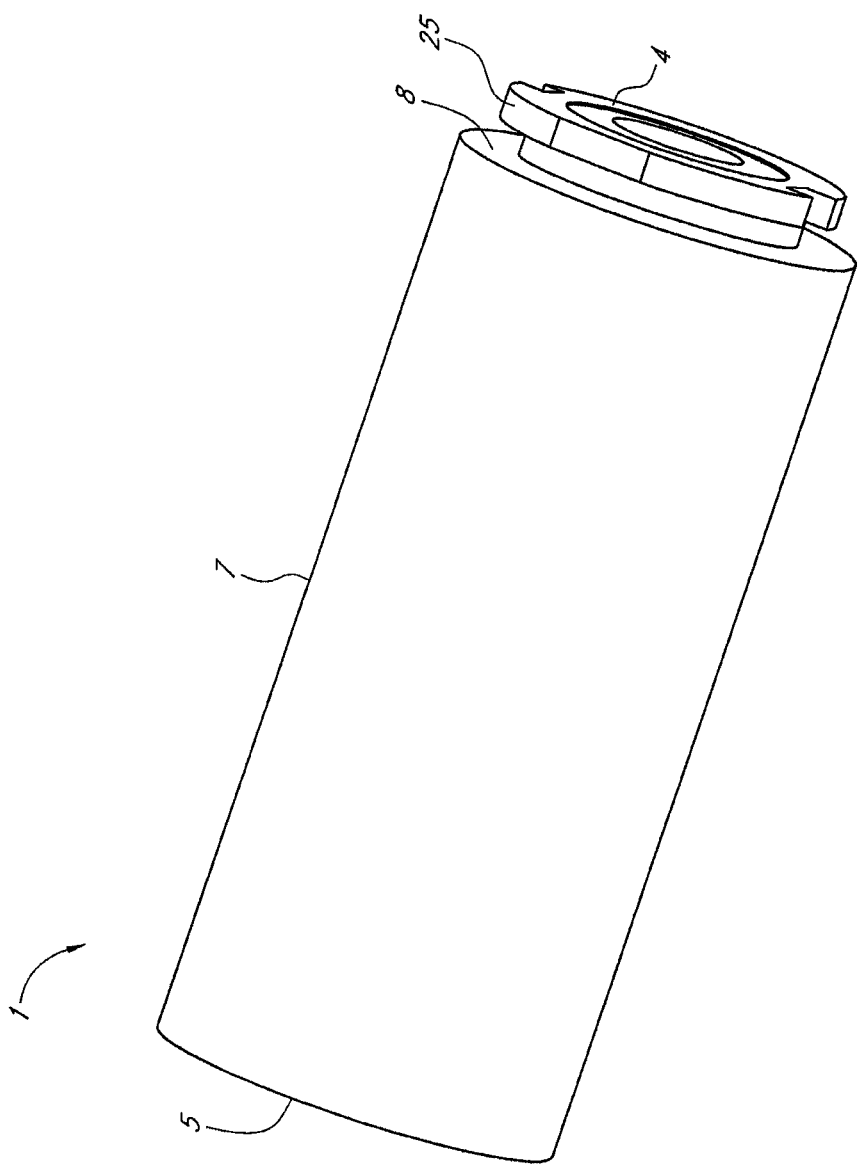

FIG. 32 illustrates a perspective view of the adapter 1 in FIG. 30 having an adapter lock end 4, a syringe lock end 5, a hollow body 7 and a fit-in notch 8 located near the adapter lock end 4. The fit-in notch 8 is capable of receiving a mateable collar or flange located on the glue gun 2 that will lock the adapter 1 to the glue gun 2 upon rotation of the adapter.

Figure 33:
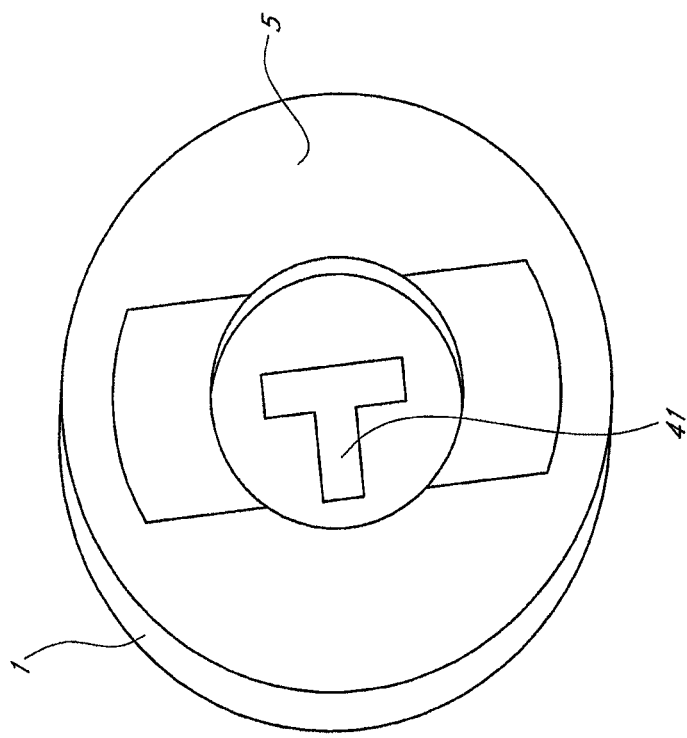

FIG. 33 illustrates a front perspective view of the adapter 1 of FIG. 30, including the syringe lock end 5. An opening 41 located on the syringe lock end 5 is also shown. The opening 41, which is configured to receive a dispenser plunger 3, is T-shaped in some embodiments, although single slit, "I", arcuate, or other shaped openings are also possible. The advantage of the T-shaped opening 41 is that it can provide better guidance for a dispenser plunger 3 that is received through the syringe lock end 5, as the T-shaped opening provides specific paths along the "T" shape for the plunger 3 to move. The T shape can also add strength to the plunger 3, such as in the longitudinal direction, for more efficient dispensing. The T shape also could add stability to the plunger 3 in the transverse direction to increase its buckling strength so that it will be less likely to buckle during the dispensing of high viscosity materials.

Figure 34:
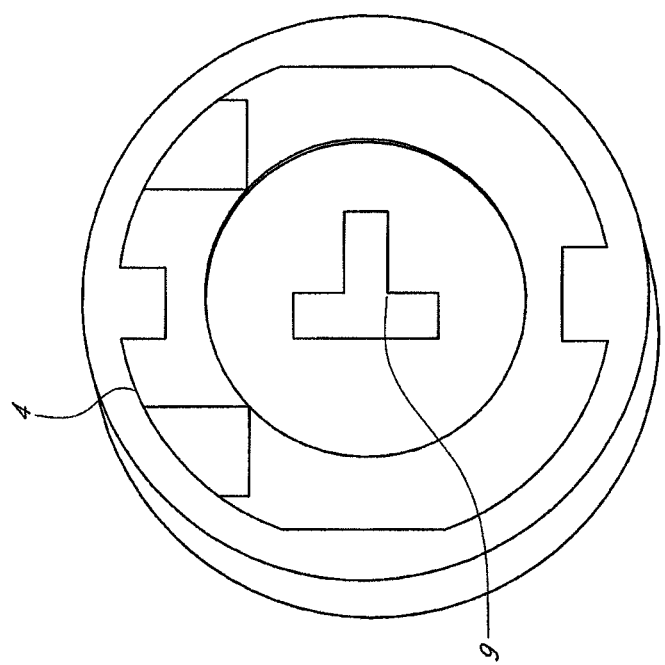

FIG. 34 illustrates a rear perspective view of the adapter 1 of FIG. 30, including the adapter lock end 4. The adapter lock end 4 includes its own T-shaped opening 9, similar to the T-shaped opening 41 in the syringe lock end 41, through which dispenser plunger 3 can pass.

Figure 35:
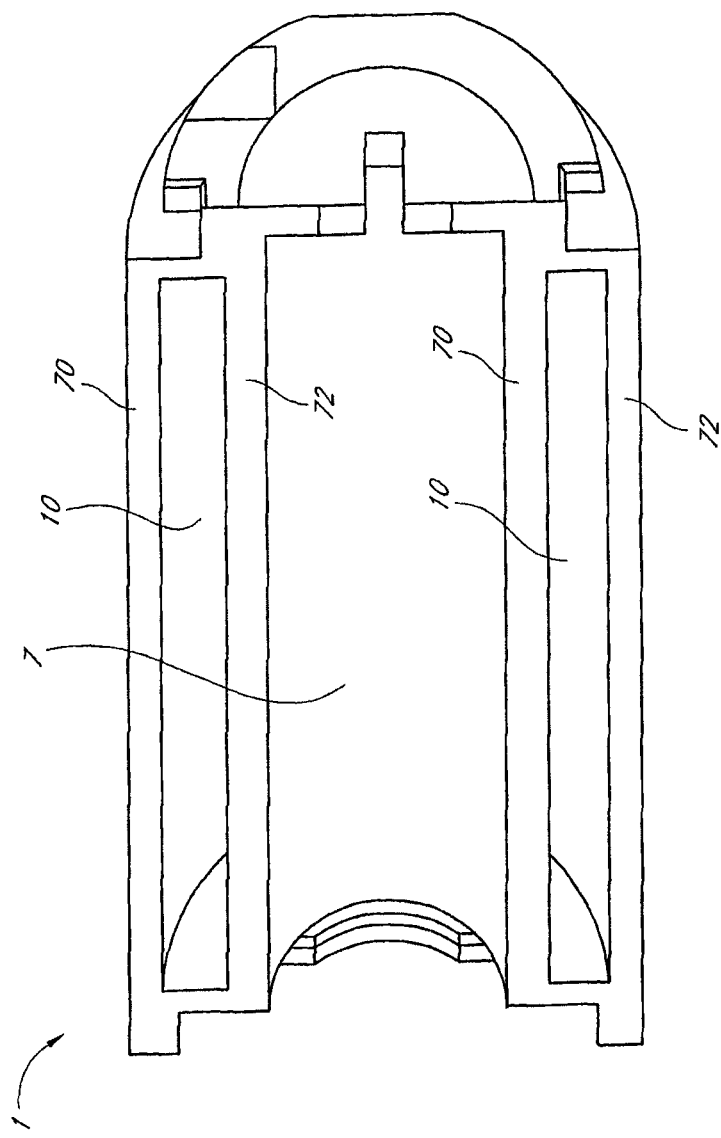

FIG. 35 illustrates a cross-sectional view of the adapter 1 of FIG. 30 and its hollow body 7. The adapter 1 includes a central lumen 7 with open proximal and/or distal ends and designed to allow the syringe plunger 3 to move through during the injection process. The adapter 1 also can optionally include one, two, or more side lumens 10 defined between walls 70 and 72, which can provide the adapter 1 with a reduced weight, which can be beneficial in some circumstances. In some embodiments, the side lumens 10 define a closed free space volume that is at least about 10%, 20%, 30%, 40%, 50%, 60%, 70%, 80%, 90%, or more of the entire enclosed volume between walls 70, 72. By providing an adapter with reduced weight, this allows for improved handling, reduced weight, and cost efficiencies for manufacturing purposes. In other embodiments, the adapter 1 can include regions besides or in addition to the second hollow space 10 that are removed or cut-out of the adapter 1 to provide additional weight reduction.

Figure 36:
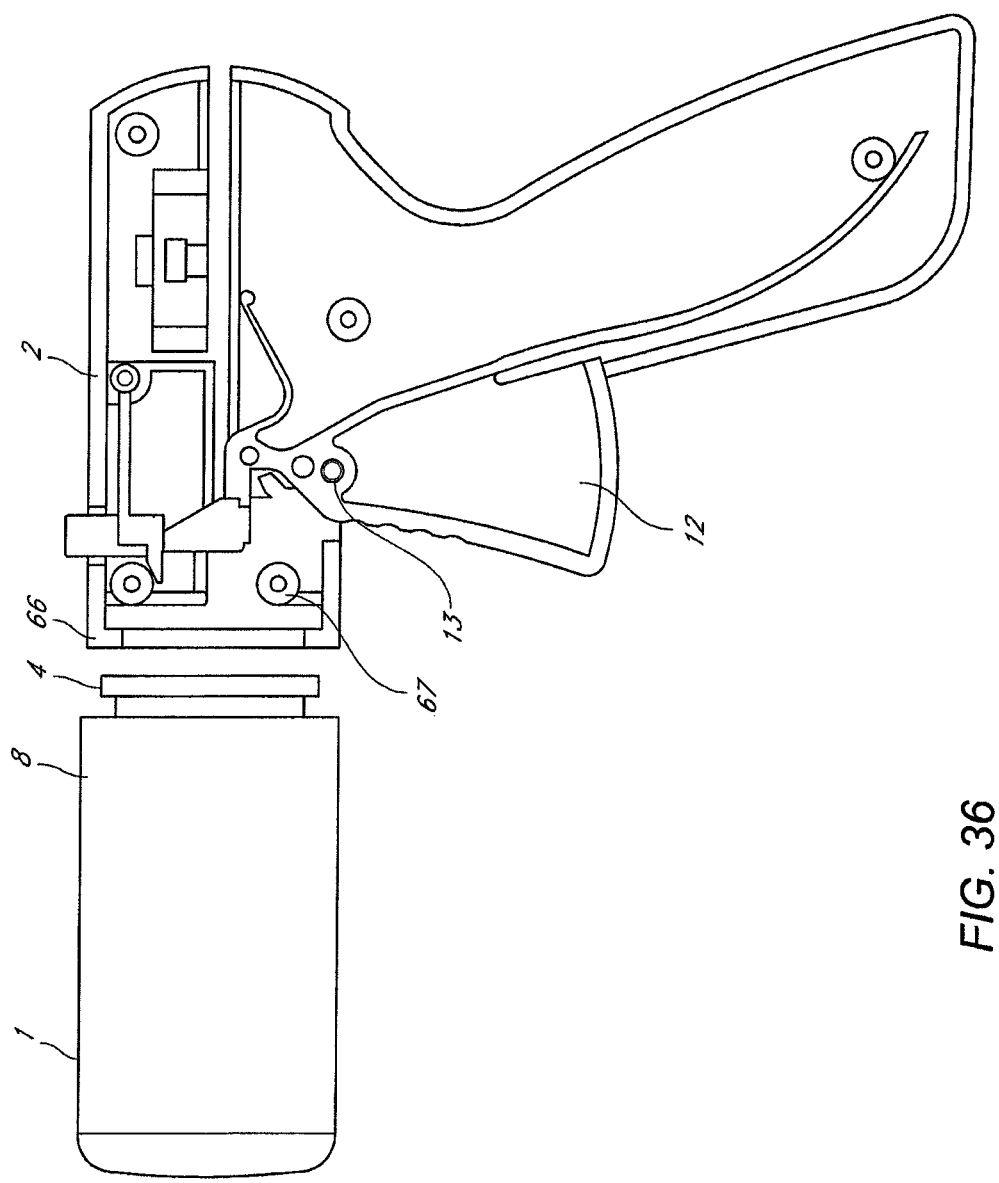
FIGS. 36-37 schematically illustrate a glue gun and adapter assembly.

FIG. 36 illustrates an adapter 1 and glue gun 2 prior to assembly. In some embodiments, the glue gun 2 includes extensions 66 that enclose an open space 67 for receiving the adapter lock end 4 of the adapter 1. While the adapter lock end 4 is placed in the open space 67, the extensions 66 of the glue gun 2 enclose the fit-in notch 8 of the adapter 1, thereby forming a secure connection between the adapter 1 and glue gun 2, as shown in FIG. 37.

Figure 37:
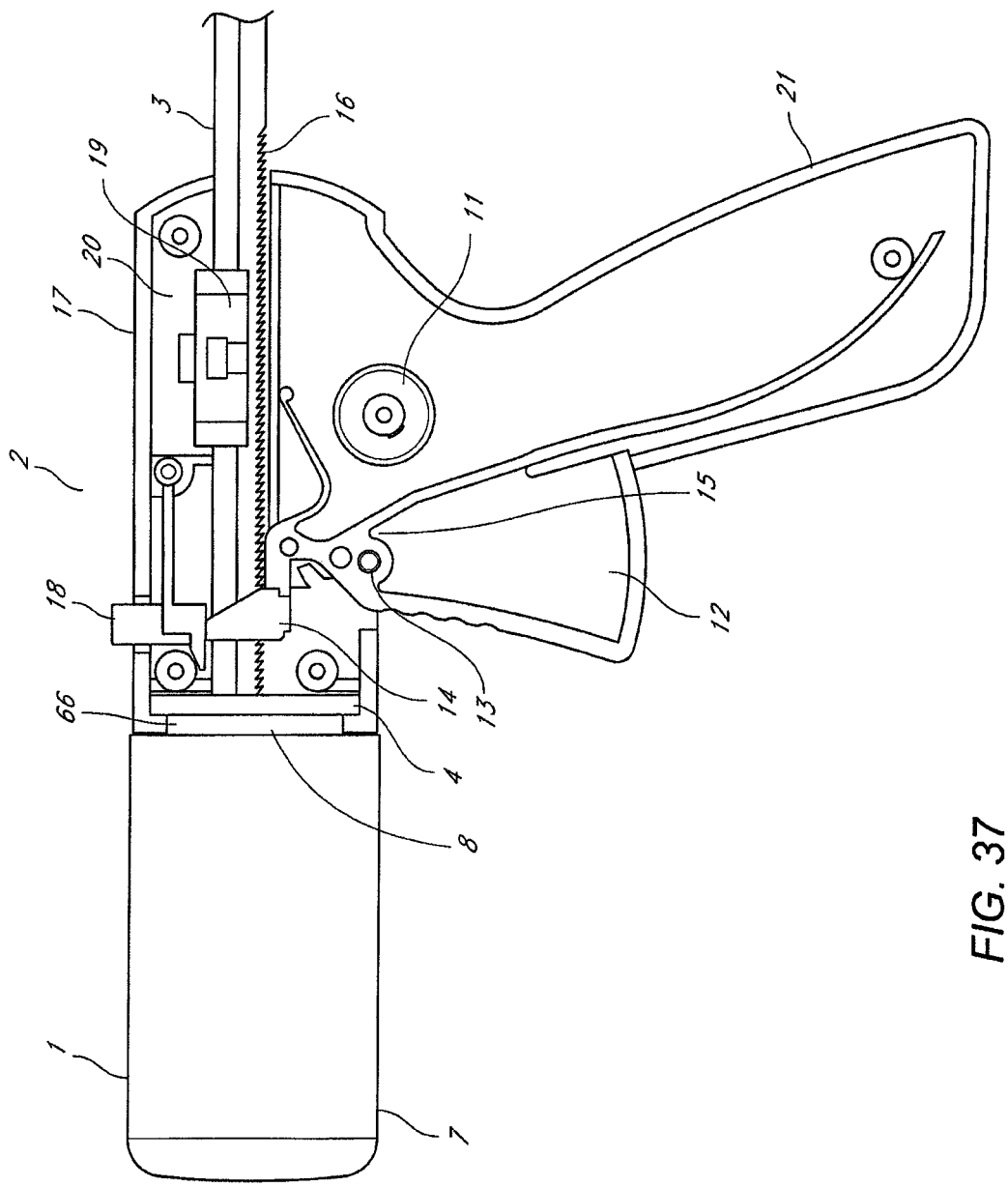

FIG. 37 illustrates the adapter 1 and glue gun 2 of FIG. 36 following assembly. Included in the assembly within the hollow body 17 of the glue gun are plunger 3 with teeth 16, stopper 11, spring mechanism 15 including spring pin 13 and spring pawl 14, plunger release button 18, floating gripper 19, plunger pocket 20 and spring stop 21.

As shown in FIG. 37, the assembly includes a glue gun 2 having a trigger 12 for controlling the dispensation of glue from the gun. The trigger 12 of the glue gun is integrated with the gun body by a spring pin 13, which is part of a spring mechanism 15. The spring mechanism 15 also includes a spring pawl 14 designed to interact with teeth 16 of the plunger 3 to precisely lock the position of the plunger. Movement of the spring pawl 14 is controlled by the trigger 12. Upon pressing or clicking of the trigger, the spring pawl 14 is adjusted to allow one or more teeth 16 of the plunger 3 to move forward through the adapter 1 and press against a syringe (not shown) to dispense a glue or adhesive. To prevent the rearward movement of the plunger 3 after clicking the trigger, a floating gripper 19 is provided that engages with the plunger 3 to stop rearward movement by frictional force. Plunger pocket 20 can allow movement (both forward and backward) of floating gripper 19 in the pocket. During the forward movement of the plunger 3, the floating gripper 19 moves with the plunger 3 (because of the friction between them) assisted by the plunger pocket 20. After the trigger is released and the plunger 3 (with the floating gripper 19) moves backward, the plunger pocket 20 sets the limit for the movement of the plunger 3. The plunger release button 18 allows the disengagement between the plunger 3 and the spring pawl 14. Pushing the plunger release button 18 will move the spring pawl 14 downward and release the plunger 3 from the spring pawl 14. Then the plunger 3 will be free to move in either backward or forward directions.

To limit the effect of the spring mechanism 15 and restrict the forward displacement of the plunger teeth 16, the spring mechanism 15 is accompanied by a stopper 11. The stopper 11 serves as a physical barrier to the movement of the spring mechanism, thereby providing for greater control over dispensation of the glue or adhesive.

Figure 38:
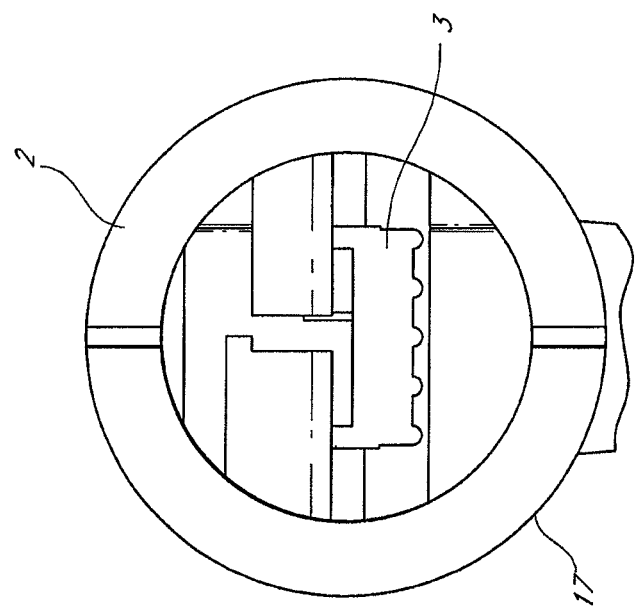
FIG. 38 schematically illustrates a front view of a glue gun, according to one embodiment of the invention.

FIG. 38 is a front view of the glue gun 2 that illustrates the mechanisms within the gun hollow body 17. Among the mechanisms within the gun hollow body 17 includes the plunger 3, which is displaced within the hollow body by the pull of the gun trigger.

The embodiments of the glue gun system described in FIGS. 25-38 are designed to deliver precise amounts of adhesive or similar vein-occluding substance and can be used with the methods described above. By providing greater control over the dispensation of vein-occluding substance, such as by using a spring mechanism 15 including spring pawl 14 and stopper 11, the glue gun system can deliver the vein-occluding substance continuously or in discrete injectable quantities, such as 0.1 ml to 1.0 ml per injection, thereby advantageously reducing the risk of overflow and back-clogging of the delivery system. The amount of vein-occluding substance used can depend on the size of the vein, the compression pressure, and surrounding environment. The glue gun will allow for exact increments of adhesive to be extruded or discharged from a catheter. This will allow a vein to be sealed shut at multiple sites along its length.

Deployable Occlusion Device

Embodiments are now described that relate to components of a venous occlusion system comprising a deployable occlusion device. FIG. 39 schematically illustrates components that can be used in a venous occlusion system, according to one embodiment of the invention. The system can include, for example, a deployable occlusion device 100 for insertion into a desired location within a vein; a catheter 200 which can be a tubular member for delivering the occlusion device 100 as well as serving as a conduit for delivery of one or more substances for closing the vein; and an injector 300 that can be coupled to the catheter 200 and actuating the substance into the vein via the catheter.

FIGS. 40A-40D illustrate various views of one embodiment of a vascular occlusion device 100, according to one embodiment of the invention. Although certain particular embodiments of an occlusion device will be described in detail herein, one of skill in the art will appreciate that any of a variety of occlusion devices can be utilized in the system of the present invention. In some embodiments, the occlusion device can be transformable from a first, reduced cross-sectional configuration for transluminal advance to the deployment site, to a second, radially enlarged or transversely enlarged configuration for occluding the vein. Transformation from the reduced configuration to the enlarged configuration can be accomplished in a generally radially symmetrical fashion, or in an elliptical, or planar fashion, each of which can accomplish the result of achieving localized closure of the tubular structure such as a vein in which the device is deployed. However, in some embodiments, the occlusion device 100 can be a vein-occluding substance, e.g., a bolus of glue, as will be described further below.

Transformation of the occlusion device may be accomplished in any of a variety of ways, such as by releasing a restraint on a frame which is biased in the direction of the enlarged configuration. Alternatively, the occlusion device may be transformed to the enlarged configuration under active force, such as by axial shortening to achieve radial expansion. As a further alternative, occlusion devices for use with the system of the present invention may include detachable inflatable balloons, open cell or closed cell foam, sponge, embolic coil meshes having either a randomized or predetermined pattern, or other structures depending upon the desired clinical performance. The occlusion device may be provided with one or two or more tissue anchors or barbs, for engaging the vessel wall, or other anti-migration surface features such as a roughened or adhesive surface, and/or enhanced surface area for contact with the vessel wall in a manner sufficient to inhibit migration.

Figure 40A:
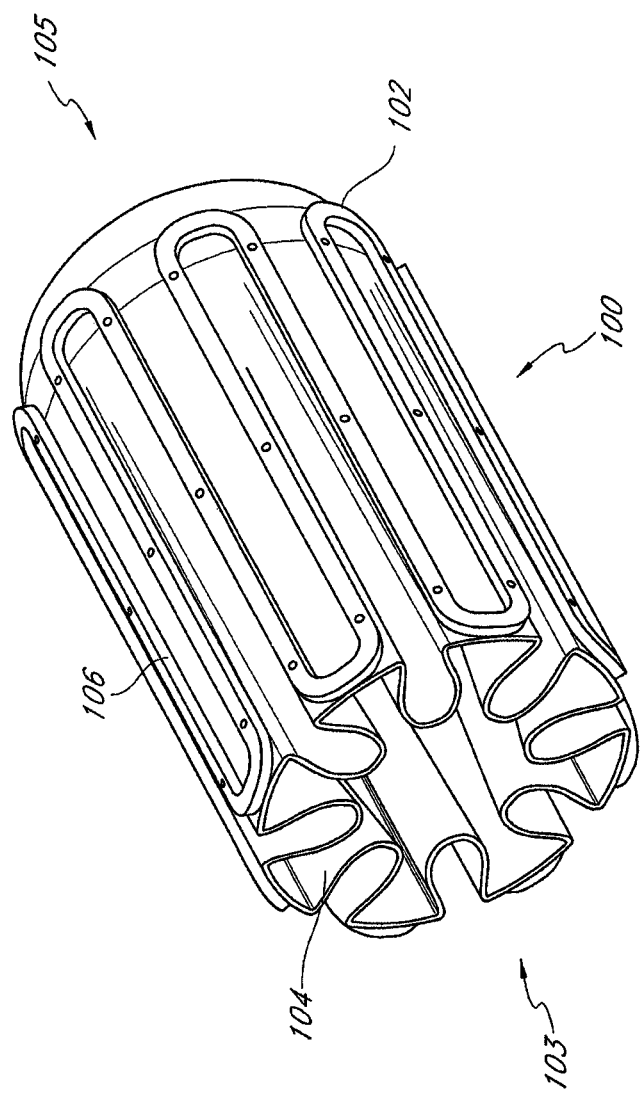
FIGS. 40A-40D illustrate various views of a vascular occlusion device, according to one embodiment of the invention.

FIG. 40A is a perspective view of an occlusion device 100 that includes a frame portion 102 and a barrier portion 106. The occlusion device is shown in a reduced, low crossing profile configuration for delivery, such as within a catheter 200. The frame portion 102 as shown has a proximal end 103 and a distal end 105, and can include at least 2 or 3 or 6 or 8 or more interconnected struts 106 as shown.

The frame 102 may have a wide variety of wall patterns depending on the desired clinical result, or have a continuous sidewall in some embodiments. In the illustrated embodiment, the wall pattern comprises a generally sinusoidal framework including a plurality of proximally facing apexes 112 and distal apexes 110 interconnected by a plurality of struts 114. This can be clearly seen, for example, in FIG. 42B.

The frame portion 102 can be made of a metal, such as stainless steel, or a shape memory material such as, for example, nitinol or elgiloy. However, in some embodiments, the frame portion 102 may be made of a shape memory polymer or biodegradable material, such as, for example, poly(alpha-hydroxy acid) such as poly-L-lactide (PLLA); poly-D-lactide (PDLA), polyglycolide (PGA), polydioxanone, polycaprolactone, polygluconate, polylactic acid-polyethylene oxide copolymers, modified cellulose, collagen, poly(hydroxybutyrate), polyanhydride, polyphosphoester, poly(amino-acids), or related copolymers. In some embodiments, the frame portion 102 can be laser-cut out of a tube. If the frame portion 102 is biodegradable, it can be configured to fully degrade over a period of time depending on the desired clinical result and the properties of the vein-occluding substance (e.g., hardening or polymerization time of a glue), such as, for example, less than about 1 year, 6 months, 3 months, 1 month, 2 weeks, 1 week, 3 days, 1 day, 12 hours, 6 hours, 3 hours, or less.

The barrier portion 104 can be sized, shaped, and attached to the frame 102 in a variety of ways such that when deployed in an expanded configuration in the blood vessel, the occlusion device 100 prevents blood flow through the vessel. In some embodiments, the barrier 104 is coupled to the frame 102 via sutures, adhesives, clips, or other form of attachment. The barrier 104 may be made of any appropriate biocompatible material suitable for occluding a vessel, such as a mesh. In some embodiments, the barrier 104 may be made of nitinol, elgiloy, Dacron®, Gore-Tex®, nylon, TFE, PTFE, ePTFE, peritoneum, subintestinal submucosa or other synthetic or biological membrane. Further materials that can be used for both the frame 102 and barrier 106 portions can be found, for example, in U.S. Patent Pub. No. 2007/0292472 A1 to Paul et al., which is hereby incorporated by reference in its entirety.

Figure 40D:
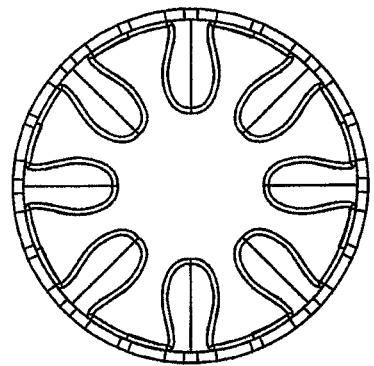
Figure 40B:
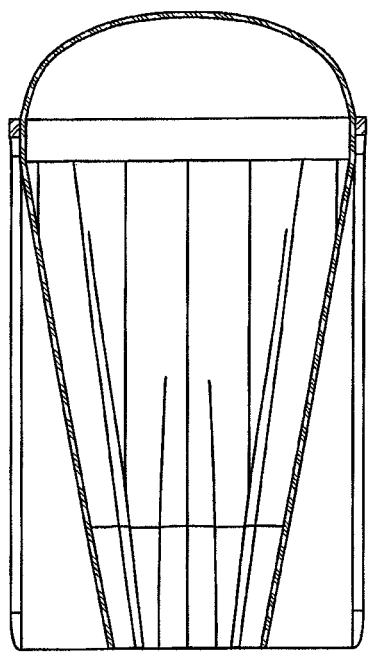
Figure 40C:
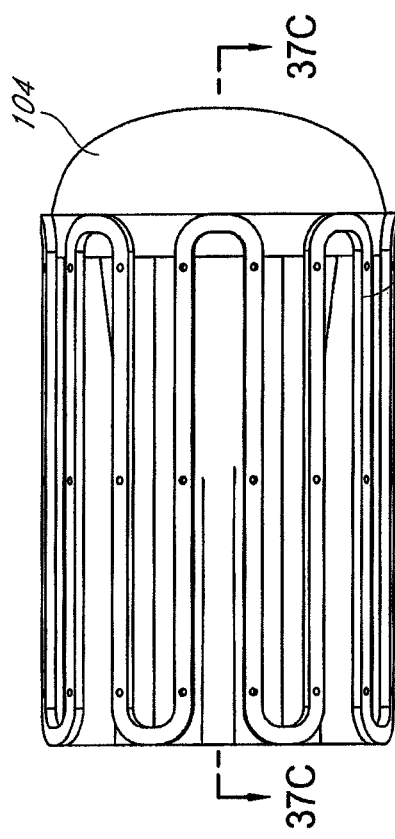
Figure 41A:
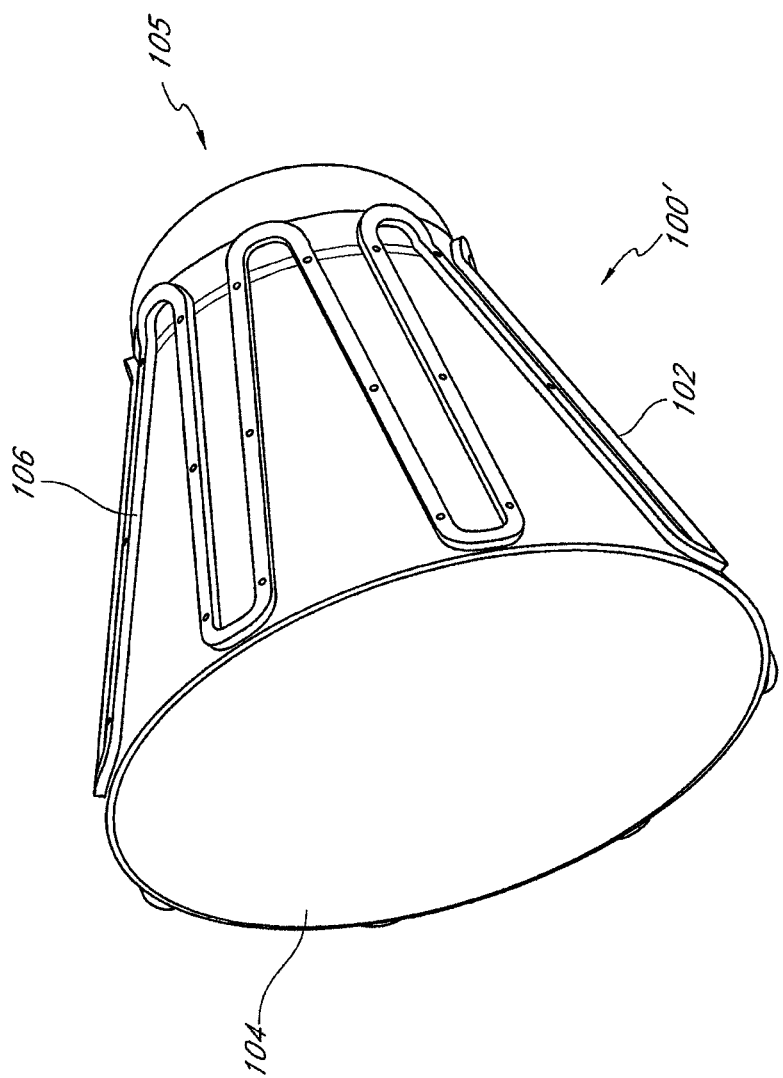
FIGS. 41A-41D illustrate various views of the occlusion device of FIGS. 2A-2D in an expanded configuration.
Figure 41D:
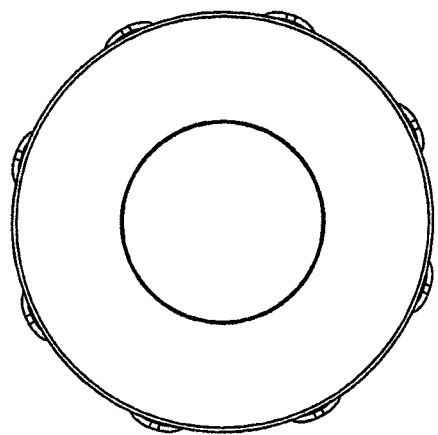
Figure 41C:
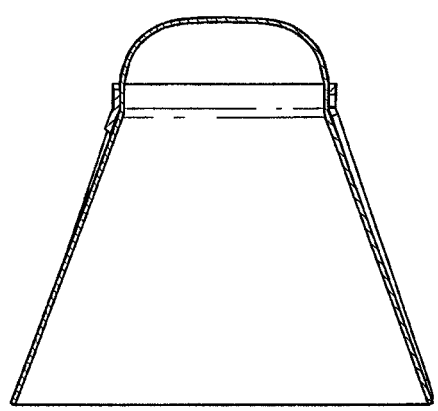
Figure 41B:
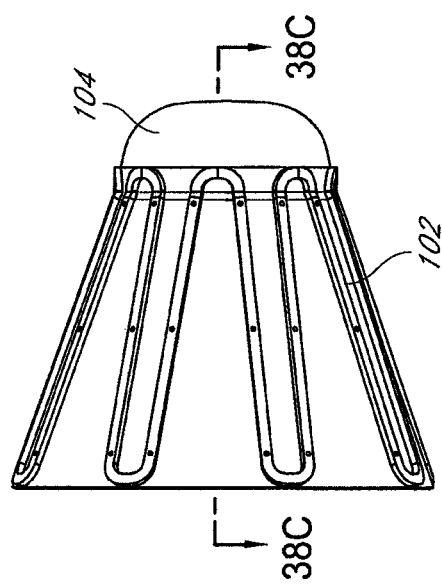

FIG. 40B illustrates a side view of the occluder illustrated in FIG. 40A. FIG. 40C illustrates a section through line A-A of FIG. 40B, showing the barrier 104 as well as frame 102. FIG. 40D is an end view of the device illustrated in FIGS. 40A-40C.

While the above occlusion device 100 is described as having a frame portion 102 and a barrier portion 104, various other occlusion devices to prevent blood flow through the vessel lumen are also within the scope of the invention, such as plugs, sponges, coils, adhesives, prothrombotic agents, and the like.

In the embodiment illustrated in FIG. 40A-40D, the axial length of the frame when in the compressed configuration is generally within the range of from about 5 mm to about 30 mm, or about 10 mm to about 20 mm in some embodiments. The outside diameter of the frame when compressed within the catheter is generally no greater than about 8 French, and preferably no greater than about 4 French in some embodiments. The maximum outside diameter of the occlusion device when in an unconstrained expansion is generally within the range of from about 2 mm to about 16 mm, or about 4 mm to about 12 mm in some embodiments.

FIGS. 41A-41D illustrates the occlusion device 100 of FIGS. 40A-40D in a deployed configuration. As noted above, the occlusion device 100 may be made of a shape memory material to facilitate self-expansion of the device from a reduced to an enlarged configuration. In other embodiments, the device 100 is balloon-expandable. As shown, the diameter of proximal end 103 of the device 100' expands to greater than that of the distal end 105 in order to engage the vessel wall and occlude the vessel. In some embodiments, the diameter of the proximal end 103 expands to at least about 110%, 120%, 130%, 140%, 150%, 200%, or more of its diameter in an undeployed configuration. In some embodiments, the device 100 includes, such as on its proximal end 103, one or more retention structures for retaining the device 100 in the vessel wall. In some embodiments, a plurality of barbs or other anchors are provided, for engaging adjacent tissue to retain the occlusion device 100 in its implanted position and to limit relative movement between the tissue and the occlusion device 100. The anchors are provided on one device 100. The anchors are provided on one or more of the struts 106, or other portion of frame 14. In some embodiments, every strut, every second strut, or every third strut are provided with one or two anchors each, or more. The anchor can be in a form or a barb, spike, or other appropriate configuration for securing the occlusion device 100 to the vessel wall, as illustrated in greater detail in FIG. 43 below.

Figure 42A:
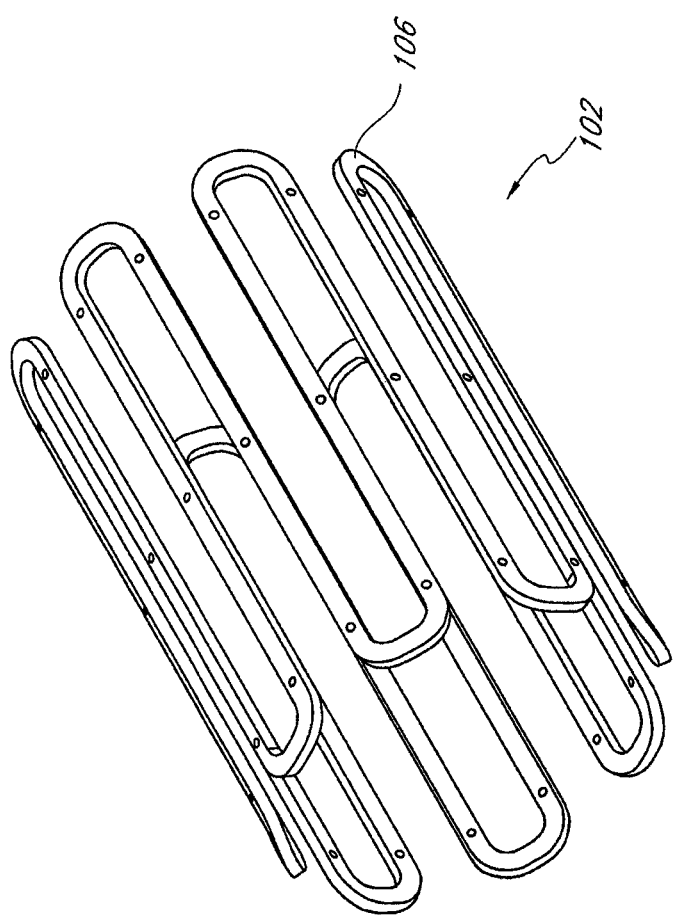
FIGS. 42A-42B illustrate an embodiment of the frame portion of the delivery device described above in connection with FIGS. 2A-3D with the barrier portion omitted for clarity.
Figure 42B:
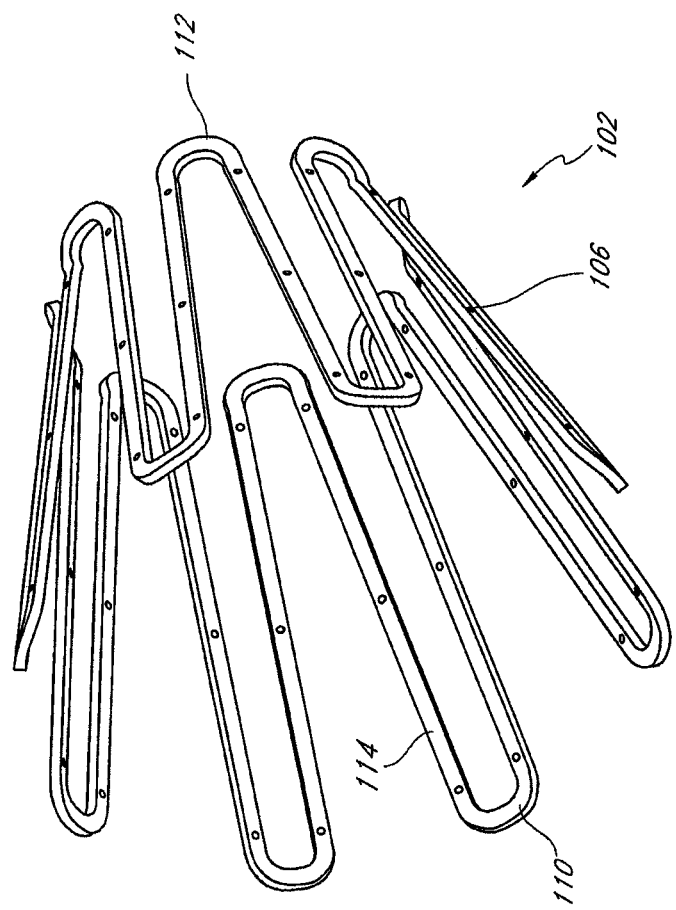

FIGS. 42A-42B illustrate an embodiment of the frame 102 portion of the delivery device described above in connection with FIGS. 2A-3D in its undeployed (FIG. 42A) and deployed (FIG. 42B) configurations with the barrier portion 104 omitted for clarity.

Figure 43:
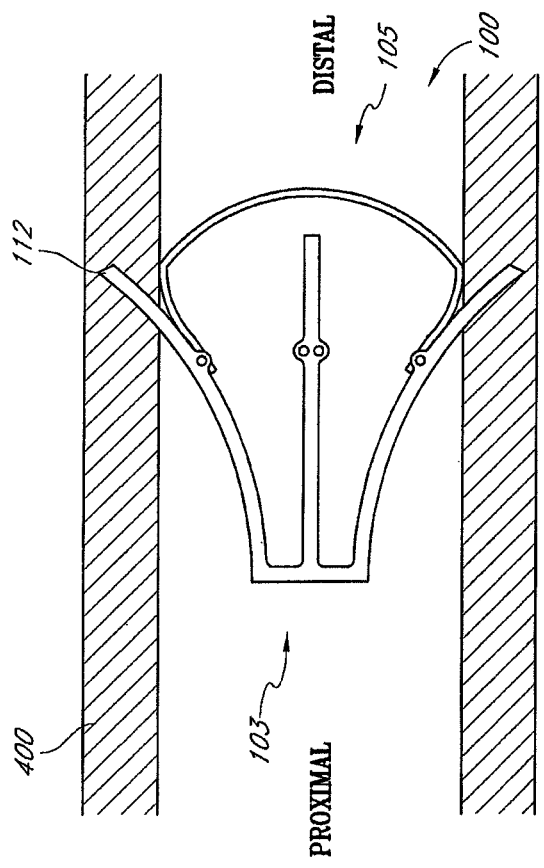
FIG. 43 is a side cross-sectional view of an occlusion device in an expanded configuration and implanted within a vessel, according to one embodiment of the invention.

FIG. 43 is a side cross-sectional view of an occlusion device 100 in an expanded configuration and implanted within vessel 400. As previously described, the occlusion device 100 has a proximal end 103, distal end 105, and one or more anchors 112 to limit relative movement between the occlusion device 100 and the vessel wall 400. The device 100 may have any number of anchors depending on the desired clinical result, such as at least 1, 2, 3, 4, 5, 6, or more anchors.

Figure 44:
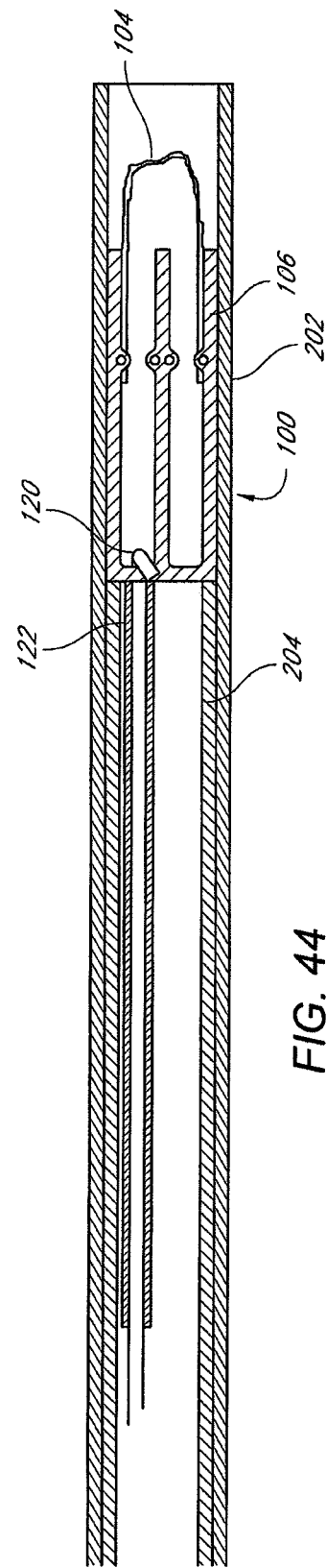
FIG. 44 is a cross-sectional view of an occlusion device in an undeployed configuration within a delivery catheter, according to one embodiment of the invention.

FIG. 44 is a longitudinal cross-sectional view of an occlusion device 100 such as that illustrated in FIG. 43, and in an undeployed configuration within a delivery catheter 200. Delivery catheter 200 includes an inner catheter member 204 and an outer catheter member 202. Occlusion device resides within a lumen of outer catheter member 202. Relative movement of inner catheter member 204 relative to outer catheter member 202, such as retraction of outer catheter member 202 relative to inner catheter member 204 or pushing of inner catheter member 204 distally relative to outer catheter member 202 can facilitate deployment of the occlusion device 100 within the vessel 400. Inner catheter member 204 may comprise a concentric tube, a push wire, or other structure capable of transmitting a deployment activating force.

Occlusion device 100 as shown is releasably attached to a detach mechanism 120 that allows for retraction and repositioning of the occluder member prior to deployment. The detach mechanism 120 can be any of a wide variety of mechanisms to provide releasable detachment, for example, mechanical, chemical, or electrolytic detachment. Some examples of mechanical detach mechanisms include a snare, suture loop, clip and the like. The proximal end of the catheter preferably includes a luer lock or similar mechanism for coupling to a syringe or other injector for inserting a vein-occluding substance into the vein.

In some embodiments, after the occlusion device is deployed, a vein-occluding material such as a sclerosing agent is injected into the vein. The purpose of the vein-occluding material can be to partially or completely destroy the endothelial cells lining the venous lumen, expose the subendothelial collagen fibers within the vein, and ultimately form a fibrous cord. After the lining of the vein is damaged the vein can be forced closed by the use of compression stocking worn by the patients. Over time the damaged vein scars upon itself creating a completely closed vein. Endothelial damage is preferably as complete as possible, because otherwise, thrombus will form and layer endoluminally. The presence of a deployed occlusion device 100 advantageously prevents distal embolization of the vein-occlusion substance distally past the occlusion device 100. Any vein-occluding material can be used depending on the desired clinical result.

A wide variety of vein-occluding substances can be used. In some embodiments, the substance can include an adhesive such as cyanoacrylate, e.g., 2-octyl cyanoacrylate, and/or a sclerosing agent such as hypertonic saline, sodium tetradecyl sulfate, chromated glycerol, tetracycline, talc, bleomycin, or polydocanol. Other adhesives that can be used include a biological glue such as a bovine serum albumin-gluteraldehyde combination (e.g., BIOGLUE, Cryolife, Atlanta, Ga.). In some embodiments, a foam generated from, for example, one or more of the above components can be used to enhance ablation and closure of the vein. The viscosity and air bubble mixture can also be controlled taking into account the desired clinical result. Ultrasound or other imaging modalities such as, for example, fluoroscopy, CT, or MRI can be used to observe and control distribution of the vein-occlusion substance. In some embodiments, foam or other micro-bubbles within the vein-occlusion substance can also serve as ultrasonic contrast. Further examples of agents, methods, and devices for vein closure that can be used as well are described, for example, in U.S. Pat. No. 4,039,665 to Foley, U.S. Pat. No. 5,676,962 to Garrido et al., U.S. Pat. No. 6,572,873 to Osman et al., U.S. Pat. No. 6,726,674 to Leu, U.S. Pat. No. 7,314,466 to Lary et al., and U.S. Patent Pub. No. 2003/0206864 A1 to Mangin, all of which are hereby incorporated by reference in their entireties. In some embodiments, the invention can be practiced using a cyanoacrylate based echogenic adhesive, visible under conventional ultrasound.

Figure 45:
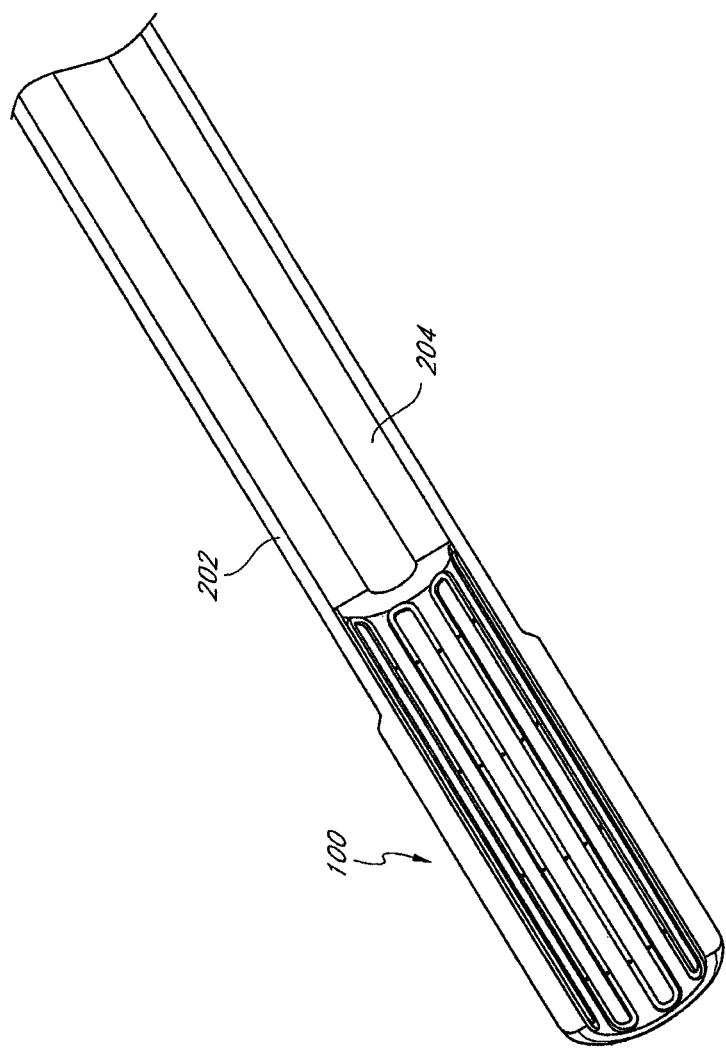
Figure 46:
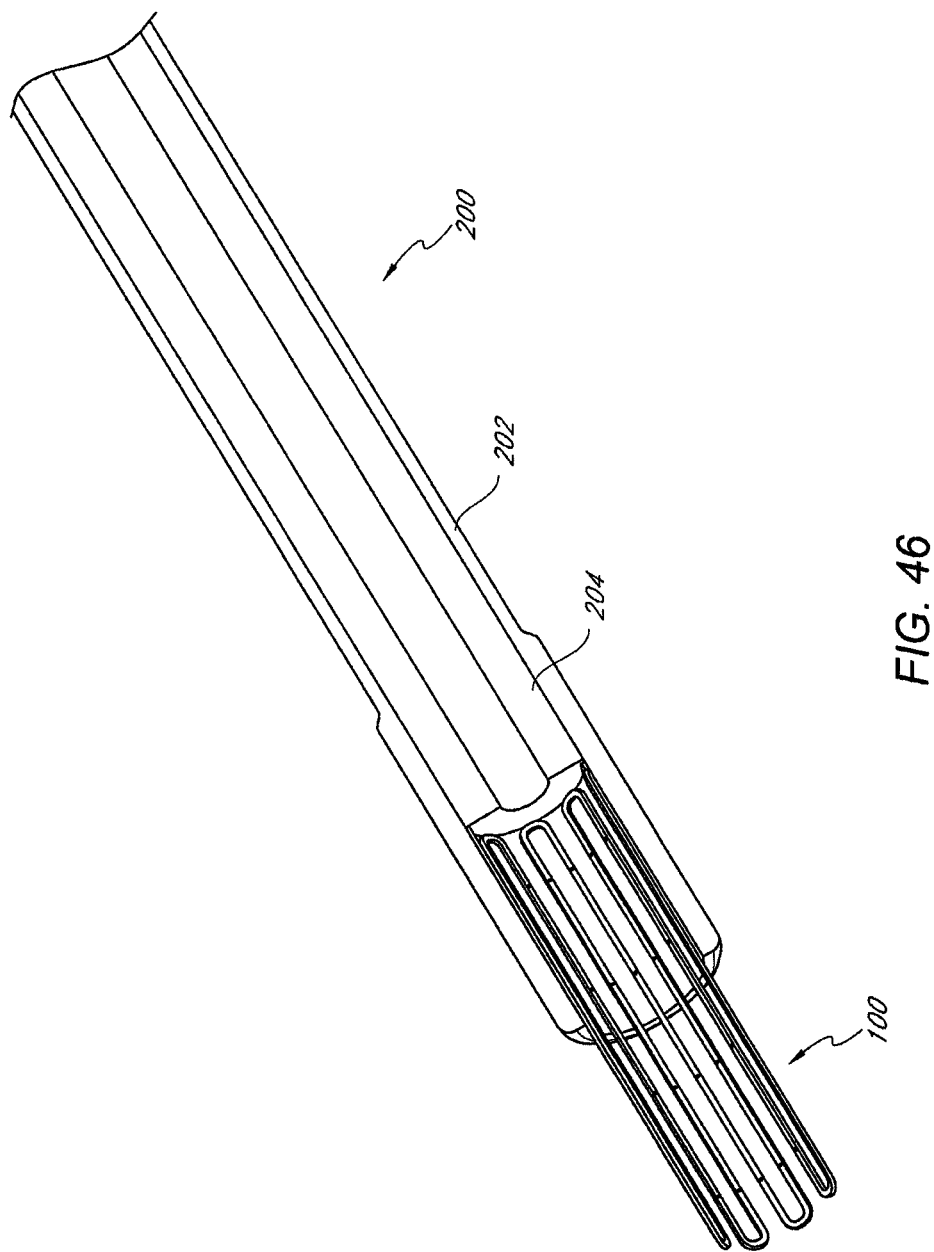

FIGS. 45-47 illustrate a cross-section of occlusion device 100 (with barrier portion 104 not shown for clarity) in varying stages of deployment caused by relative movement of inner catheter 204 relative to outer catheter 202.

Using the systems and methods described herein provides little to no risk of injury to surrounding nerves or tissue, because the length of the treated vessel can be clearly identified without unnecessary overtreatment. This is in contrast to many other procedures which require, for example, that a catheter is placed superior to nerves which may be juxtaposed to the saphenous vein.

The vein closure system allows for a simple treatment for veins, such as abnormal refluxing varicose veins. The vein closure system includes the delivery system and the unique intravascular adhesive. The procedure is less invasive, less painful, more effective and easier to recover from compared to existing treatments.

Although this application has been disclosed in the context of certain embodiments and examples, it will be understood by those skilled in the art that the present application extends beyond the specifically disclosed embodiments to other alternative embodiments and/or uses of the application and obvious modifications and equivalents thereof. Additionally, the skilled artisan will recognize that any of the above-described methods can be carried out using any appropriate apparatus. Further, the disclosure herein of any particular feature in connection with an embodiment can be used in all other disclosed embodiments set forth herein. Thus, it is intended that the scope of the present application herein disclosed should not be limited by the particular disclosed embodiments described above.

What is claimed is:

1. A medical device for use under ultrasound visualization, the medical device comprising:
   an elongate shaft comprising an outer surface and an inner surface defining an inner lumen, the inner lumen having an open proximal end and an open distal end;
   a plurality of microwells embedded within the elongate shaft,
   wherein each microwell of the plurality of microwells is arranged between the inner surface and the outer surface of the elongate shaft and has a longitudinal axis normal or oblique to a longitudinal axis of the elongate shaft, each microwell having a respective uncovered opening on the outer surface of the elongate shaft
   wherein each microwell of the plurality of microwells comprises opposing walls that run parallel to each other, and
   wherein the microwells are configured to contain a gas within to increase the visibility of the medical device under ultrasound imaging.

2. The medical device of claim 1, wherein the elongate shaft comprises one or more see-through portions and one or more opaque portions.

3. The medical device of claim 2, wherein the one or more opaque portions comprise titanium dioxide.

4. The medical device of claim 1, wherein the elongate shaft comprises indicia of length measurements at least partially along the axial length of the elongate shaft.

5. The medical device of claim 4, wherein the indicia comprise laser markings.

6. The medical device of claim 1, wherein a diameter of each microwell of the plurality of microwells is less than about 150 μm.

7. The medical device of claim 1, wherein the plurality of microwells are equally spaced radially around the elongate shaft.

8. The medical device of claim 1, wherein the plurality of microwells are irregularly spaced radially around the elongate shaft.

9. The medical device of claim 1, wherein the elongate shaft is sized and configured to be placed within the saphenous vein.

10. A medical device for use under ultrasound visualization, the medical device comprising:
   an elongate shaft comprising an outer surface and an inner surface defining an inner lumen, the inner lumen having an open proximal end and an open distal end;
   at least one ring of microwells embedded within the elongate shaft, the microwells of each ring being arranged circumferentially about the elongate shaft, each microwell being substantially linear and having a longitudinal axis that is either oblique or normal to a longitudinal axis of the elongate shaft, wherein the microwells are arranged between the inner surface and outer surface of the elongate shaft, wherein each microwell comprises opposing walls that run parallel to each other, and wherein the microwells are configured to contain a gas within to increase the visibility of the medical device under ultrasound imaging.

11. The medical device of claim 10, further comprising a plurality of rings of microwells, wherein each ring comprises a plurality of microwells, and wherein the plurality of rings are spaced apart longitudinally by equal distances.

12. A medical device for use under ultrasound visualization, the medical device comprising:

an elongate shaft comprising an outer surface and an inner surface defining an inner lumen;

one or more microwells within the elongate shaft, each microwell having a respective opening on the outer surface of the elongate shaft, each microwell having a cross-sectional dimension configured such that gas is retained within the microwell but surface tension prevents liquid from entering the microwell, each microwell comprising opposing walls that run parallel to each other, and each microwell having a longitudinal axis that is either normal or oblique to a longitudinal axis of the elongate shaft, wherein the one or more microwells are configured to contain gas to increase the visibility of the medical device under ultrasound imaging.

13. The medical device of claim 12, wherein the longitudinal axis of at least one of the one or more microwells is substantially normal to the longitudinal axis of the elongate shaft.

14. The medical device of claim 12, wherein the longitudinal axis of at least one of the one or more microwells is oblique to the longitudinal axis of the elongate shaft.

15. The medical device of claim 12, wherein the one or more microwells extend partially through the elongate shaft.

16. The medical device of claim 12, wherein the one or more microwells extend fully through the elongate shaft.

17. The medical device of claim 12, wherein the cross-sectional area of each microwell is less than about 150 µm.

18. The medical device of claim 12, wherein the cross-sectional area of each microwell is less than about 100 µm.

19. The medical device of claim 12, wherein the cross-sectional area of each microwell is less than about 50 µm.

* * * * *